US008988620B2

United States Patent
Israel et al.

(10) Patent No.: US 8,988,620 B2
(45) Date of Patent: Mar. 24, 2015

(54) LIQUID CRYSTAL BASED ANALYTE DETECTION

(75) Inventors: Barbara A. Israel, Mount Horeb, WI (US); Nicholas Abbott, Madison, WI (US); Christopher Murphy, Madison, WI (US); Karla Hollister, DeForest, WI (US); Syrus Soltaninassab, Madison, WI (US); Doug Hansmann, Madison, WI (US); Bharat Raj Acharya, Madison, WI (US)

(73) Assignee: Platypus Technologies, LLC, Madison, WI (US)

( * ) Notice: Subject to any disclaimer, the term of this patent is extended or adjusted under 35 U.S.C. 154(b) by 450 days.

(21) Appl. No.: 12/550,733

(22) Filed: Aug. 31, 2009

(65) Prior Publication Data

US 2010/0009344 A1 Jan. 14, 2010

Related U.S. Application Data

(63) Continuation of application No. 10/897,626, filed on Jul. 23, 2004, now abandoned.

(60) Provisional application No. 60/490,122, filed on Jul. 25, 2003, provisional application No. 60/518,706, filed on Nov. 10, 2003, provisional application No. 60/541,516, filed on Feb. 3, 2004.

(51) Int. Cl.
| | |
|---|---|
| *G02F 1/1335* | (2006.01) |
| *C12Q 1/00* | (2006.01) |
| *C12Q 1/70* | (2006.01) |
| *G01N 33/567* | (2006.01) |
| *B82Y 30/00* | (2011.01) |

(Continued)

(52) U.S. Cl.
CPC ............... *B82Y 30/00* (2013.01); *B82Y 15/00* (2013.01); *G01N 33/54373* (2013.01); *G01N 33/56983* (2013.01)
USPC .................................. 349/16; 435/4; 435/7.2

(58) Field of Classification Search
None
See application file for complete search history.

(56) References Cited

U.S. PATENT DOCUMENTS

| 2,639,815 A | 5/1953 | Paluck |
| 3,645,693 A | 2/1972 | Poziomek et al. |

(Continued)

FOREIGN PATENT DOCUMENTS

| EP | 1549953 A2 | 7/2005 |
| GB | 2297549 A | 7/1996 |

(Continued)

OTHER PUBLICATIONS

Souady, et al. Structural Profiling of Individual Glycosphingolipids in a Single Thin-Layer Chromatogram by Multiple Sequential Immunodetection Matched with Direct IR-MALDI-o-TOF Mass Spectrometry. Anal. Chem. 2009, 81, 9481-9492.*

(Continued)

*Primary Examiner* — Zachariah Lucas
*Assistant Examiner* — Stuart W Snyder
(74) *Attorney, Agent, or Firm* — Casimir Jones S.C.

(57) ABSTRACT

The present invention relates to the field of detection of viruses, and in particular to detection of viruses using a liquid crystal assay format. In the present invention, virus binding in a detection region is identified by changes in liquid crystal orientation caused by virus binding independent orientation caused by any topography associated with the detection region.

28 Claims, 13 Drawing Sheets

(51) Int. Cl.
*B82Y 15/00* (2011.01)
*G01N 33/543* (2006.01)
*G01N 33/569* (2006.01)

(56) References Cited

U.S. PATENT DOCUMENTS

| | | | |
|---|---|---|---|
| 3,883,398 A | 5/1975 | Ono | |
| 3,910,763 A | 10/1975 | Poziomek et al. | |
| 4,068,925 A | 1/1978 | Tani et al. | |
| 4,096,086 A | 6/1978 | Kanbe et al. | |
| 4,285,697 A | 8/1981 | Neary et al. | |
| 4,551,264 A | 11/1985 | Eidenschink et al. | |
| 4,597,942 A | 7/1986 | Meathrel et al. | |
| 4,612,873 A | 9/1986 | Eberle | |
| 4,795,253 A | 1/1989 | Sandridge et al. | |
| 4,927,879 A | 5/1990 | Pidgeon | |
| 5,055,408 A | 10/1991 | Higo et al. | |
| 5,059,394 A | 10/1991 | Phillips et al. | |
| 5,063,024 A | 11/1991 | Partanen et al. | |
| 5,073,294 A | 12/1991 | Shannon et al. | |
| 5,132,226 A | 7/1992 | Dreher et al. | |
| 5,141,718 A | 8/1992 | Clark et al. | |
| 5,298,394 A | 3/1994 | Arima et al. | |
| 5,355,215 A | 10/1994 | Schroeder et al. | |
| 5,370,841 A | 12/1994 | McDonnell et al. | |
| 5,474,796 A | 12/1995 | Brennan | |
| 5,484,565 A | 1/1996 | Larsen et al. | |
| 5,599,919 A | 2/1997 | Yen et al. | |
| 5,601,980 A | 2/1997 | Gordon et al. | |
| 5,700,637 A | 12/1997 | Southern | |
| 5,858,659 A | 1/1999 | Sapolsky et al. | |
| 5,908,786 A | 6/1999 | Moreno et al. | |
| 5,925,525 A | 7/1999 | Fodor et al. | |
| 5,985,551 A | 11/1999 | Brennan | |
| 6,001,311 A | 12/1999 | Brennan | |
| 6,017,696 A | 1/2000 | Heller | |
| 6,040,193 A | 3/2000 | Winkler et al. | |
| 6,045,996 A | 4/2000 | Cronin et al. | |
| 6,051,380 A | 4/2000 | Sosnowski et al. | |
| 6,068,818 A | 5/2000 | Ackley et al. | |
| 6,171,780 B1 | 1/2001 | Pham et al. | |
| 6,171,802 B1 | 1/2001 | Woolverton et al. | |
| 6,201,588 B1 | 3/2001 | Walton et al. | |
| 6,242,266 B1 | 6/2001 | Schleifer et al. | |
| 6,277,489 B1 | 8/2001 | Abbott et al. | |
| 6,277,490 B1 | 8/2001 | Ruf | |
| 6,284,197 B1 * | 9/2001 | Abbott et al. | 422/82.05 |
| 6,288,392 B1 | 9/2001 | Abbott et al. | |
| 6,306,659 B1 | 10/2001 | Parce et al. | |
| 6,444,254 B1 | 9/2002 | Chilkoti et al. | |
| 6,468,657 B1 | 10/2002 | Hou et al. | |
| 6,586,257 B1 | 7/2003 | Vuong | |
| 6,586,628 B2 | 7/2003 | Abbott | |
| 6,596,545 B1 | 7/2003 | Wagner et al. | |
| 6,692,699 B2 | 2/2004 | Abbott et al. | |
| 6,780,492 B2 | 8/2004 | Abbott | |
| 6,797,463 B2 | 9/2004 | Abbott et al. | |
| 6,824,837 B2 | 11/2004 | Abbott | |
| 6,844,184 B2 | 1/2005 | Kim et al. | |
| 6,849,321 B2 | 2/2005 | Abbott et al. | |
| 6,852,285 B2 | 2/2005 | Abbott et al. | |
| 6,858,423 B1 | 2/2005 | Abbott et al. | |
| 6,884,357 B2 | 4/2005 | Siddiqi | |
| 7,018,838 B2 * | 3/2006 | Murphy et al. | 435/325 |
| 7,125,592 B2 | 10/2006 | Abbott | |
| 7,135,143 B2 | 11/2006 | Abbott | |
| 7,303,694 B2 | 12/2007 | Abbott | |
| 7,371,563 B2 | 5/2008 | Duffy et al. | |
| 2002/0004216 A1 | 1/2002 | Abbott et al. | |
| 2002/0028451 A1 | 3/2002 | Abbott et al. | |
| 2002/0052002 A1 | 5/2002 | Niehaus et al. | |
| 2002/0055093 A1 | 5/2002 | Abbott et al. | |
| 2002/0117412 A1 | 8/2002 | Rabiner et al. | |
| 2002/0123134 A1 | 9/2002 | Huang et al. | |
| 2002/0142453 A1 | 10/2002 | Abbott et al. | |
| 2002/0164604 A1 | 11/2002 | Abbott et al. | |
| 2002/0172621 A1 | 11/2002 | Barbera-Guillem | |
| 2002/0173033 A1 | 11/2002 | Hammerick et al. | |
| 2003/0032046 A1 | 2/2003 | Duffy et al. | |
| 2003/0049862 A1 | 3/2003 | He et al. | |
| 2003/0071949 A1 | 4/2003 | Abbott | |
| 2003/0099993 A1 | 5/2003 | Abbott et al. | |
| 2003/0124029 A1 | 7/2003 | Webb et al. | |
| 2003/0127396 A1 | 7/2003 | Siddiqi | |
| 2003/0180966 A1 | 9/2003 | Abbott | |
| 2003/0194753 A1 | 10/2003 | Abbott | |
| 2004/0002131 A1 | 1/2004 | Kim et al. | |
| 2004/0009583 A1 | 1/2004 | Bennet et al. | |
| 2004/0038408 A1 | 2/2004 | Abbott et al. | |
| 2004/0091620 A1 | 5/2004 | Abbott | |
| 2004/0142411 A1 | 7/2004 | Kirk et al. | |
| 2004/0161800 A1 | 8/2004 | Abbott et al. | |
| 2004/0224380 A1 | 11/2004 | Chou et al. | |
| 2005/0064395 A1 | 3/2005 | Israel et al. | |
| 2005/0079486 A1 | 4/2005 | Abbott | |
| 2005/0079487 A1 | 4/2005 | Abbott | |
| 2005/0106562 A1 | 5/2005 | Abbott | |
| 2005/0112544 A1 | 5/2005 | Xu et al. | |
| 2005/0158880 A1 | 7/2005 | Ostuni et al. | |
| 2005/0221271 A1 | 10/2005 | Abbott | |
| 2005/0260703 A1 | 11/2005 | Abbott | |
| 2006/0003389 A1 | 1/2006 | Abbott | |
| 2006/0141446 A1 | 6/2006 | Abbott | |
| 2006/0252031 A1 | 11/2006 | Abbott | |
| 2007/0004046 A1 | 1/2007 | Abbott | |
| 2007/0042505 A1 | 2/2007 | Abbott | |
| 2007/0099249 A1 | 5/2007 | Abbott | |
| 2007/0104612 A1 | 5/2007 | Abbott | |
| 2007/0110614 A1 | 5/2007 | Abbott | |
| 2007/0231832 A1 | 10/2007 | Abbott | |
| 2007/0269848 A1 | 11/2007 | Abbott | |
| 2008/0050799 A1 | 2/2008 | Abbott | |
| 2008/0160539 A1 | 7/2008 | Abbott | |
| 2008/0187949 A1 | 8/2008 | Goldbard et al. | |
| 2009/0054262 A1 | 2/2009 | Abbott et al. | |

FOREIGN PATENT DOCUMENTS

| | | |
|---|---|---|
| WO | WO 91/18653 A2 | 12/1991 |
| WO | WO 99/63329 | 6/1999 |
| WO | WO 00/50570 A2 | 8/2000 |
| WO | WO 01/61325 A2 | 2/2001 |
| WO | WO 01/61325 A3 | 2/2001 |
| WO | WO 01/61357 A2 | 2/2001 |
| WO | WO 01/61357 A3 | 2/2001 |
| WO | WO 02/071929 A2 | 9/2002 |
| WO | WO 02/075294 | 9/2002 |
| WO | WO 03/021339 A3 | 9/2002 |
| WO | WO 03/019191 | 3/2003 |
| WO | WO 03/021339 A2 | 3/2003 |
| WO | WO 03/029481 | 4/2003 |
| WO | WO 03/081230 | 10/2003 |
| WO | WO 03/086197 | 10/2003 |
| WO | WO 2004/041061 | 5/2004 |
| WO | WO 2004/044583 | 5/2004 |
| WO | WO 2005/010160 | 2/2005 |
| WO | WO 2005/047863 | 5/2005 |

OTHER PUBLICATIONS

Charych, et al. Direct Colorimetric Detection of a Receptor-Ligand Interaction by a Polymerized Bilayer Assembly. Science; 1993; 261(5121): 585-588.*

Gupta et al, "Optical Amplification of Ligand-Receptor Binding Using Liquid Crystals," Science vol. 279, Mar. 27, 1998 pp. 2077-2080.

Green et al., "Mechanism of the Transformation of a Stiff Polymer Lyotropic Nematic Liquid Crystal to the Cholesteric State by Dopant-Mediated ChiralInformation Transfer", J. Am. Chem. Soc., 1998. 120,9810-9817.

Seung Ryeol Kim et al. Anal. Chem "A Possible Substrate for Biomolecular Assays Based on Liquid Crystals, Analytical 2 Chemistry,"(2000) 72(19);4646-4653.

(56) References Cited

OTHER PUBLICATIONS

Lauer L. et al, "Spot Complaint Neuronal Networks by Structure Optimized Micro-Contact Printing" Biomaterials, Elsevier Science, 2001, vol. 22, pp. 1925-1932.

Kikuchi H E et al, "Culture of Bone-Marrow-Derived Cells in Microfabricated Pit Arrays" Proc SPIE Int Soc Opt Eng; 2001, vol. 4265, pp. 40-49.

Iwuoha E I et al: Reactivities of Organic Phase Biosensors 3: Electrochemical Study of Cytochrome P450 Cam Immobilized in a Methyltriethoysilane SOL-GEL Electroanalysis, VHC Publishers Inc. ( 2000) vol. 12, p. 980.

Skaife, Justin G et al. "Quantitative Interpretation of the Optical Textures of Liquid Crystals Caused by Specific Binding of Immunoglobulins to Surface-Bound Antugens," Langmuir (2000) 16(7):3529-3536.

Skaife, Justin G et al, "Quanitative Characterization of Obliquely Deposited Subtrates of Gold by Atomic Force Microscopy: Influence of Subtrate Topography on Anchoring of Liquid Crystals" Chemistry of Materials, V 11(3) 1999, pp. 612-623.

Vinay K. Gupta et al. "Using Droplets of Nematic Liquid Crystal to Probe the Microscopic and Mesoscopic Structure of Organic Surfaces," Langmuir 15:21 (1999) 7213-7223.

R.R. Shah et al. "Principles for Measurement of Chemical Exposure Based on Recognition-Driven Anchoring Transitions in Liquid Crystals," Science (2001) 393(5533):1296-99.

Kleinfeld D. et al., "Controlled Outgrowth of Dissociated Neurons on Patterned Substrates," J. Neurosci. (1998) 8:4098 120.

Kumar et al. "Patterned Self-Assembled Monolayers and Meso-Scale Phenomena," Langmuir (1994) 10:1498 511.

Xia Y, "Use of Controlled Reactive Spreading of-Liquid Alkanethiol OD the Surface of Gold to Modify the Size of Features Produced by Mierocontact Printing," Whitesides, G., J. Am. Chern. Soc. (1995) 117:327475.

Hickman et al., "Rational pattern design for in vitro cellular networks using surface photochemistry," J. Vac. Sci. Technol. (1994) 12:607 16.

Jerome, Blandine, "Surface effects and anchoring in liquid crystals," Rep. Prog. Phys. (1991) 54:391 451.

Gupta et al. Design of Surfaces for Patterned Alignment of liquid Crystals on Planar and Curved Substrates, Science (1997) 276:1533-1536.

Drawhorn et al, "Anchoring of Nematic Liquid Crystals on Self-Assembled Monolayers Formed from Alkanethiols on Semitransparent Films of Gold," J. Phys. Chem. (1995) 45:16511.

Ladam, Guy et al, "Protein Adsorption onto Auto-Assembled Polyelectrolyte Films," Langmuir (2001) 17(3):878-882.

Wagner et aL "Covalent Immobilization of Native Biomolecules onto Au(111} via N-Hydroxysuccinimide Ester Functionalized Self-Assembled Monolayers for Scanning Probe Microscopy," Biophys. J. (1996) 70:2052 2066.

Tarlov et al.,"UV Photopatterning of Alkanethiolate Monolayers," J. Am. Chem. Soc (1993) 115: 5305.

Kumar et aL, "Patterned Self-Assembled Monolayers and Meso-Scale Phenomena," Acc. Chem. Res. (1995) 28: 219.

Resler D. P et al, "High-efficiency liquid-crystal optical phased-array beam steering," Opt. Lett. (1996) 21, 689.

Stern, Margaret B, "Binary Optics: A VLSI-based microoptics technology," Microelectron. Eng. (1996) 32. 369.

Goto et aL, "Design of an Aberration-Free Spherical Micro Lens with a Diffractive Relief Grating Film on a Refractive Spherical Glass Substrate," Jpn. J. AppL Phys. (1992) 31,1586.

Magiera et aL, "Hybrid Imaging Element—Possibilities of Aberration Correction," Soc. Photo Opt. Instrum. Eng., (1996) 2774, 204.

Bernard, et al. Affinity capture of proteins from solution and their dissociation by contact printing. Nature Biotechnology. 2001; 19(9):866-869.

Woolverton, et al.; "A liquid crystal biosensor for virus detection"; Abstracts of the General Meeting of the American Society for Microbiology, (2002), vol. 102, pp. 110-111, (2 pgs.) Abstract Only.

"Fast, Cheap, and Portable: A New Pathogen Detection Tool"; Biomedical Instrumentation & Technology, Technology Trends (2002), 36(1), pp. 15.

Renault, Jean Philippe, et al.; "Fabricating Microarrays of Functional Proteins Using Affinity Contact Printing"; Agnew. Chem. Int. Ed. (2002), vol. 41, No. 13, pp. 2320-2323.

Espinoza, Luis A. Tercero, et al.; "Orientational Behavior of Thermotropic Liquid Crystals on Surfaces Presenting Electrostatically Bound Vesicular Stomatitis Virus"; Langmuir (2004); vol. 20, pp. 2375-2385.

Tingey, Matthew L., et al.; "Imaging of Affinity Microcontact Printed Proteins by Using Liquid Crystals"; Langmuir (2004); vol. 20, pp. 6818-6826.

\* cited by examiner

Figure 2
Anti-E Rabbit Polyclonal Antibodies
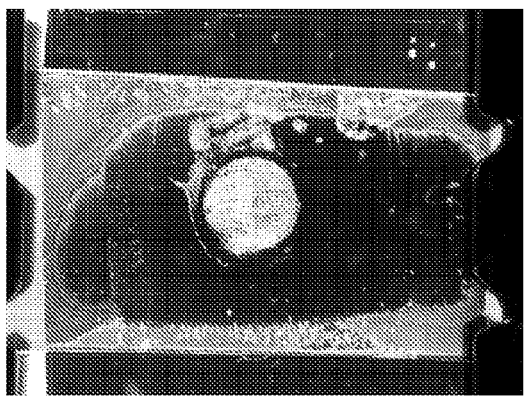
- Rabbit Serum
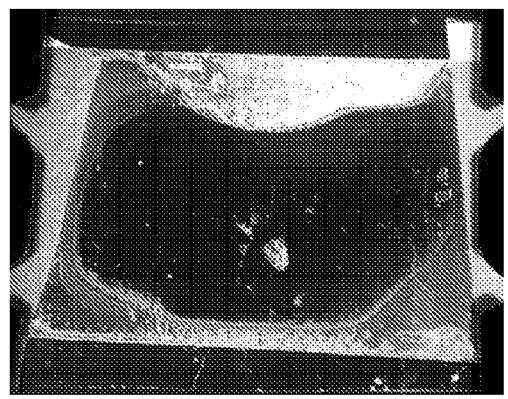
+ Horse Serum
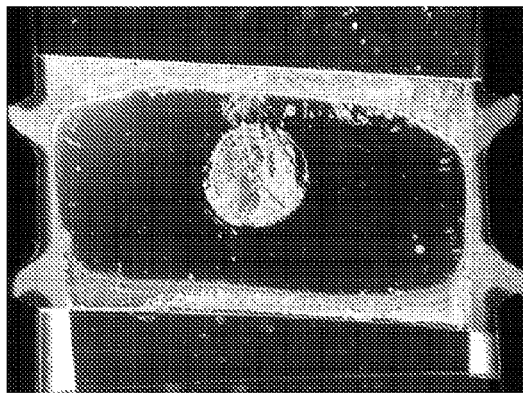
- Horse Serum
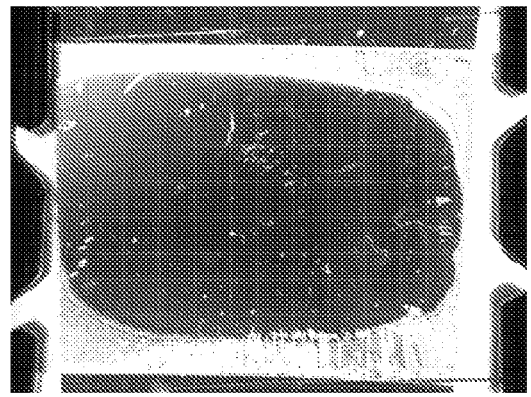

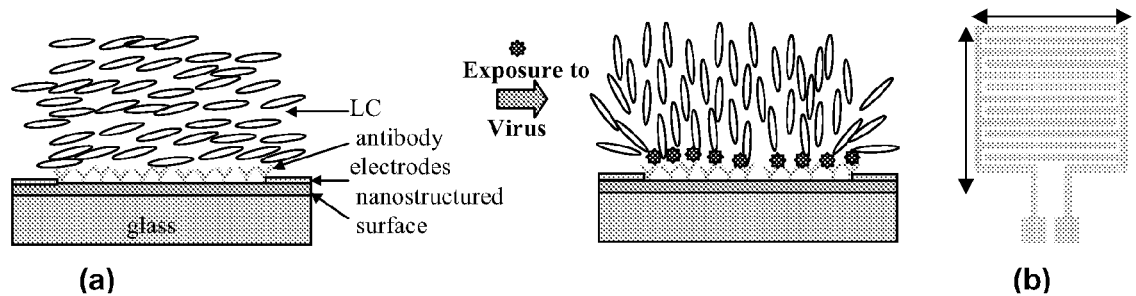

Figure 3. (a) The schematic cross-sectional view depicting the principle of detection of virus particle using LCs. The liquid crystal molecules supported on a nanostructured surface coated with antibody assume a planar orientation. Upon binding the virus particles on to the surface the molecules align perpendicular to the surface inducing a change in the capacitance between two electrodes. (b) Schematics of interdigitated electrodes. The size of the arrows is on the order of 500 μm.

Figure 6. (a) Schematic of hyperbolic electrodes (b) the potential distribution in the plane of electrodes obtained by solving Laplace equation in 3D (c) the gradient of $E^2$ in a plane at $z = 4$ μm above the electrode plane and (d) on a $y = 0$ plane.

Figure 7. (a) A schematic of dielectrophoretic setup. (b) A 2 mm thick sheet of PDMS with a hole at the center confines the sample on the *active* region.

Elution buffer    BSA 200ng/mL    F1 5ng/mL    F1 10ng/mL    F1 50ng/mL    F1 200ng/mL BSA        F1 200ng        F1 40ng        F1 8ng Figure 15
Anti-biotin antibody (100ug/ml) immobilized substrates after exposed to:
  
    PBS buffer      Biotin labeled liposome    unlabeled liposome
Anti-biotin antibody (20ug/ml) immobilized substrates after exposed to:
 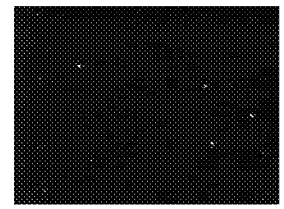 
    PBS buffer      Biotin labeled liposome    unlabeled liposome

LIQUID CRYSTAL BASED ANALYTE DETECTION

CROSS REFERENCE TO RELATED APPLICATIONS

This application is a continuation of U.S. application Ser. No. 10/897,626, filed Jul. 23, 2004, which claims the benefit of U.S. Provisional Application 60/490,122, filed Jul. 25, 2003; U.S. Provisional Application 60/518,706, filed Nov. 10, 2003; and U.S. Provisional Application 60/541,516, filed Feb. 3, 2004, all of which are herein incorporated by reference in their entirety.

GOVERNMENT SUPPORT

This invention was made with government support under SBIR Grant No. 5R43AI4960602 awarded by the National Institutes of Health/NIAID. The Government has certain rights in the invention.

FIELD OF THE INVENTION

The present invention relates to the field of detection of analytes, and in particular to detection of viruses, cells, bacteria, lipid-membrane containing organisms, proteins, nucleic acids, carbohydrates and other biomolecules, organic molecules and inorganic molecules using a liquid crystal assay format.

BACKGROUND OF THE INVENTION

The detection of pathogen, protein, and nucleic acid targets in biological samples forms the basis of the multi-billion dollar in vitro diagnostic industry. Detection of protein and nucleic acid targets can be divided into diagnostic and research based markets. The diagnostic market includes the detection and identification of pathogens such as viruses and bacteria, the identification of various genetic markers, and the identification of markers associated with the presence of tumors. The research market includes the genomics and proteomics industries, which require analytical, drug discovery, and high-throughput screening technologies.

Initial viral diagnostics consisted of the crude, albeit sensitive and non-specific techniques of direct inoculation of sample material into suckling mice, embryonated eggs, or living cells. Diagnostic methods have since evolved to the sensitive, specific, but time consuming serological techniques of neutralization, ELISA and fluorescent antibody assays and subsequently to the current highly sensitive, instrumentation-dependent techniques of nucleic acid amplification and luminescent bead-based assays. This evolution in approach to virus detection and identification has been driven by advances in biology (cell culture, immunology), followed by advances in biochemistry (immunochemistry, molecular biology, dye chemistry). More recent progress comes from advances in instrumentation sciences (optics, electronics, robotics, miniaturization, microfluidics, etc.) and by the subsequent interfacing of microelectronics with biology to develop the first generation of biosensors.

There are many ways to detect the presence of a virus in a sample. Methods with the highest sensitivity (real-time PCR, tissue culture, electron microcopy) also involve the highest complexity and/or cost, require sophisticated equipment and facilities and require highly trained personnel. Methods with less sensitivity (IFA, ELISA, dipstick methods), in practice, suffer from cross-reactivity problems, involve more hands-on time and/or are less adaptable to rapidly screening large numbers of samples. There is a great need for multiplexing in situations such as arbovirus surveillance, bio-threat monitoring, and for rapid agent identification during a disease outbreak of unknown origin. In practice, nucleic acid techniques and bead-based techniques currently can multiplex approximately 6-20 different targets.

Though there are many techniques available to detect and identify viruses, there is need for improvement. Among the desired attributes are: lower cost, less reliance on biological systems, less reliance on use of labile, expensive reagents, less complexity in execution, decreased hands-on time required for processing the sample and execution of the assay, minimal technical proficiency for running assays and interpreting results, miniaturization and portability of equipment, automation, and an increase in multiplexing capability.

SUMMARY OF THE INVENTION

The present invention relates to the field of detection of analytes, and in particular to detection of viruses, cells, bacteria, lipid-membrane containing organisms, proteins, nucleic acids, carbohydrates and other biomolecules, organic molecules and inorganic molecules using a liquid crystal assay format. Accordingly, the present invention provides methods for detecting viruses comprising: a) providing: i) a sample suspected of containing of a virus; ii) a detection device comprising a substrate comprising at least one detection region having a first virus recognition moiety immobilized thereon; and iii) mesogens; b) contacting said detection region with said sample; and c) contacting said substrate with said mesogens, wherein the presence of said virus is indicated by a change in said mesogens over said detection regions and wherein said change is independent of the presence of an additional homeotropic director on said detection region. The present invention is not limited to the detection of any particular change in the mesogens forming the liquid crystal. Indeed, a variety of changes may be detected, including, but not limited to a change in color, a change in texture, a change in tilt, and homeotropic orientation.

The present invention is not limited to the detection of any particular type of virus. Indeed, the detection of a variety of viruses is contemplated, including, but not limited to viruses in the following families: Adenoviridae, Arenaviridae, Astroviridae, Birnaviridae, Bunyaviridae, Caliciviridae, Circoviridae, Coronaviridae, Filoviridae, Flaviviridae, Hepadnaviridae, Herpesviridae, Iridoviridae, Filoviridae, Orthomyxoviridae, Papovaviridae, Paramyxoviridae, Parvoviridae, Picornaviridae, Poxyiridae, Reoviridae, Retroviridae, Rhabdoviridae, Togaviridae, Badnavirus, Bromoviridae, Comoviridae, Geminiviridae, Partitiviridae, Potyviridae, Sequiviridae, and Tombusviridae. In some embodiments, the virus is a Japanese Encephalitis Virus group virus. In other embodiments, the Japanese Encephalitis Virus group virus is selected from the group consisting of West Nile Virus and St. Louis Encephalitis Virus. In still further embodiments, the virus is an enveloped virus.

The present invention is not limited to the use of any particular substrate. Indeed, the use of a variety of substrates is contemplated, including, but not limited to metal films, glass, silicon, diamond and polymeric materials. The present invention is not limited to the use of any particular polymeric materials. Indeed, the use of a variety of polymeric materials is contemplated, including, but not limited to those selected from the group consisting of polyurethane, PDMS, polyimide, polystyrene, polycarbonate and polyisocyanoacrylate. The present invention is not limited to the use of any particular mesogen. Indeed, the use of a variety of mesogens is contemplated, including, but not limited to those selected from the group consisting of 4-cyano-4'-pentylbiphenyl, N-(4-methoxybenzylidene)-4-butlyaniline and combinations thereof. The present invention is not limited to the use of any particular virus recognition moiety. Indeed, the use of a variety of virus recognition moieties is contemplated, including, but not limited to antigen binding proteins and nucleic acids. In some embodiments, the antigen binding protein is an immunoglobulin.

In some embodiments, the substrate comprises a plurality of detection regions. In some embodiments, the plurality of detection regions have the same virus recognition moiety bound thereto. In other embodiments, the plurality of detection regions have different virus recognition moieties bound thereto. In some embodiments, the detection device further comprises a second substrate arranged opposite said first substrate to form a cell.

In still further embodiments, the change in the mesogens is detected by viewing said detection device between cross polar lenses. In some embodiments, the detection region does not homeotropically orient mesogens in the absence of virus. In some embodiments, homeotropic ordering is observed within 48 hours of the application of said sample to said detection region.

The present invention is not limited to the analysis of any particular type of sample. Indeed, the analysis of a variety of samples is contemplated, including, but not limited to biological fluids, tissue homogenates, feces, vesicular fluids, swabs of orifices or tissues, and media in which virus has been cultured or prepared. The present invention is not limited to the analysis of any particular type of biological fluid. Indeed, the present invention contemplates the analysis of a variety of biological fluids, including, but not limited to cerebral-spinal fluid, urine, serum, plasma, nasal secretions, sputum, semen and saliva.

In some embodiments, the present invention provides devices for the detection of a virus comprising a first substrate comprising at least one detection region having a first virus recognition moiety specific for said virus immobilized thereon, wherein said detection region does not homeotropically orient an added mesogen in the absence of said virus. In some embodiments, the first substrate comprises a plurality of detection regions. The present invention is not limited to the use of any particular substrate. Indeed, the use of a variety of substrates is contemplated, including, but not limited to metal films, glass, silicon, diamond and polymeric materials. The present invention is not limited to the use of any particular polymeric materials. Indeed, the use of a variety of polymeric materials is contemplated, including, but not limited to those selected from the group consisting of polyurethane, PDMS, polyimide, polystyrene, polycarbonate and polyisocyanoacrylate.

The present invention is not limited to the use of any particular virus recognition moiety. Indeed, the use of a variety of virus recognition moieties is contemplated, including, but not limited to antigen binding proteins and nucleic acids. In some embodiments, the antigen binding protein is an immunoglobulin. In some embodiments, the substrate comprises a plurality of detection regions. In some embodiments, the plurality of detection regions have the same virus recognition moiety bound thereto. In other embodiments, the plurality of detection regions have different virus recognition moieties bound thereto. In some embodiments, the detection device further comprises a second substrate arranged opposite said first substrate to form a cell. In still further embodiments, the plurality of detection regions are arranged in an array. In some embodiments, the substrates further comprise at least one control region comprising immobilized virus. In other embodiments, the device comprises a second substrate oriented opposite said first substrate to form a cell for containing mesogens. In still other embodiments, the devices comprise cross polar lenses oriented on either side of said first substrate and said substrate. In some embodiments, the substrate comprises microchannels in said first substrate, wherein said microchannels deliver sample to said detection region.

In still further embodiments, the present invention provides a kit comprising: a) a device for the detection of a virus comprising a first substrate comprising at least one detection region having a first virus recognition moiety specific for said virus immobilized thereon, wherein said detection region does not homeotropically orient an added mesogen in the absence of said virus; and b) instructions for detection of said virus. In some embodiments, the kit further comprises a vial containing mesogens. In other embodiments, the kit further comprises a vial containing a virus for use as a positive control.

In still further embodiments, the present invention provides methods comprising: a) providing a functionalized detection substrate treated to align mesogens, a stamp substrate displaying at least one ligand, a biological test sample suspected of containing a binding partner for the ligand, and mesogens; b) contacting the test sample with the stamp substrate under conditions such that the binding partner can bind the ligand; c) contacting the detection substrate with the stamp substrate under conditions such that the binding partner to the ligand is transferred to the detection substrate; d) detecting the presence of the binding partner to the ligand on the detection substrate by applying the mesogens to the substrate. The present invention is not limited to use with any particular biological sample. Indeed, the use of a variety of biological samples is contemplated, including, but not limited to, those selected from the group consisting of whole blood, serum, cerebral spinal fluid, nasopharyngeal aspirate, and nasal secretions. In some embodiments, the alignment of the mesogens by the detection substrate is disrupted by the presence of the binding partner to the ligand. In some preferred embodiments, the alignment is homeotropic. In further embodiments, the mesogens are not homeotropically aligned over areas of the detection substrate wherein the binding partner of the ligand is present. In still other embodiments, the detection substrate is used to form an optical cell. In some embodiments, the detecting is performed by analysis of the detection substrate with cross-polars. In further embodiments, areas of the detection substrate with homeotropically aligned mesogens appear dark. In other embodiments, areas of the detection substrate with substantially non-homeotropically aligned mesogens appear bright. The present invention is not limited to the use of any particular type of ligand. Indeed, the use of a variety of ligands is contemplated. In some embodiments, the ligand is an antigenic substance from a pathogenic organism. In some embodiments, the antigenic substance is a protein. In further embodiments, the protein is an envelope protein of a virus. In some preferred embodiments, the envelope protein is protein E from West Nile Virus. The present invention is not limited to the detection of any particular type of binding partner. Indeed, the detection of a variety of binding partners is contemplated. In some embodiments, the binding partner is an antibody. The present invention is not limited to the use of any particular number of ligands on a particular substrate. In some embodiments, the stamp substrate comprises two or more ligands in an array. In some preferred embodiments, the ligand is bound by binding partners from a plurality of species or genera. The present invention is not limited to the use of any particular mesogen. Indeed, the use of a variety of mesogens is contemplated. In some preferred embodiments, the mesogen is 5CB. The present invention is not limited to the use of any particular type of material to make the stamp substrate. Indeed, the use of a variety of materials is contemplated. In some preferred embodiments, the stamp substrate comprises PDMS. The present invention is not limited to the use of any particular type of detection substrate. Indeed, the use of a variety of test substrates is contemplated. In some preferred embodiments, the detection substrate comprises obliquely deposited gold.

In still further embodiments, the present invention provides kits comprising: a) a stamp substrate displaying at least one ligand; b) a functionalized detection substrate that orients mesogens; and c) instructions for using the substrates for detecting a binding partner of the ligand. In some embodiments, the kits further comprise a container of mesogens. The present invention is not limited to the use of any particular mesogen. Indeed, the use of a variety of mesogens is contemplated. In some preferred embodiments, the mesogen is 5CB. The present invention is not limited to the use of any particular type of material to make the stamp substrate. Indeed, the use of a variety of materials is contemplated. In some preferred embodiments, the stamp substrate comprises PDMS. The present invention is not limited to the use of any particular type of detection substrate. Indeed, the use of a variety of test substrates is contemplated. In some preferred embodiments, the detection substrate comprises obliquely deposited gold. The present invention is not limited to the use of any particular type of ligand. Indeed, the use of a variety of ligands is contemplated. In some embodiments, the ligand is an antigenic substance from a pathogenic organism. In some embodiments, the antigenic substance is a protein. In further embodiments, the protein is an envelope protein of a virus. In some preferred embodiments, the envelope protein is protein E from West Nile Virus. In some embodiments, the kits further comprise a container containing a control binding partner. The present invention is not limited to any particular binding partner. Indeed, a variety of binding partners are contemplated. In some embodiments, the binding partner is a ligand. In some embodiments, the kits further comprise an additional substrate for forming an optical cell. In still other embodiments, the kits comprise polarized lenses.

In still further embodiments, the present invention provides systems for detecting an analyte comprising: a) a first substrate displaying a recognition moiety, wherein the recognition moiety interacts with the analyte; b) a second substrate comprising a surface configured to receive the analyte interacting with the recognition moiety; and c) a liquid crystal overlaying the second substrate. In some embodiments, the first substrate is selected from the group consisting of a stamp, a bead, and column media. In some embodiments, the stamp comprises PDMS. In some embodiments, the bead is a magnetic bead. In some embodiments, the column is immunoaffinity column media. In some embodiments, the recognition moiety is selected from the group consisting of a protein, polypeptide, peptide, nucleic acid, carbohydrate, lipid, organic molecule and inorganic molecule. In some embodiments, the liquid crystal comprises mesogens selected from the group consisting of E7, MLC, 5CB (4-n-pentyl-4'-cyanobiphenyl), 8CB (4-cyano-4'octylbiphenyl), BL093, TL 216, ZLI 5800, MLC 6613, and MBBA ((p-methoxybenzylidene)-p-butylaniline). In some embodiments, the second substrate comprises a functionalized surface. In some embodiments, the functionalized surface comprises a polyimide. In some embodiments, the polyimide is rubbed. In some embodiments, the polyimide is selected from the group consisting of Nissan 7210, Nissan 3510, Nissan 410, Nissan 3140, Nissan 5291, and Japan Synthetic Rubber JALS 146-R19. In some embodiments, the polyimide homeotropically orients the liquid crystal. In some embodiments, the polyimide is selected from the group consisting of Nissan 7511L and SE 1211.

In further embodiments, the present invention provides methods of detecting an analyte comprising: a) providing a first substrate displaying a recognition moiety, a second substrate, mesogens, and a sample suspected of containing an analyte; b) contacting the first substrate displaying a recognition moiety with the sample suspected of containing an analyte so that the analyte interacts with the recognition moiety; c) transferring the analyte interacting with the recognition moiety to the second substrate; and d) contacting the second substrate with the mesogens to detect the presence of the analyte on the second substrate. In some embodiments, the recognition moiety is selected from the group consisting of a protein, polypeptide, peptide, nucleic acid, carbohydrate, lipid, organic molecule and inorganic molecule. In some embodiments, the analyte is selected from the group consisting of a protein, polypeptide, peptide, nucleic acid, organic molecule, inorganic molecule, virus, liposome, bacteria, fungus, and cell. In some embodiments, the first substrate is selected from the group consisting of a stamp, a bead, and column media. In some embodiments, the second substrate is selected from the group consisting of silicon, glass, polymer, diamond, and metal. In some embodiments, the second substrate comprises a surface functionalized with a polyimide. In some embodiments, the polyimide is rubbed. In some embodiments, the polyimide is selected from the group consisting of Nissan 7210, Nissan 3510, Nissan 410, Nissan 3140, Nissan 5291, and Japan Synthetic Rubber JALS 146-R19. In some embodiments, the polyimide homeotropically orients the liquid crystal. In some embodiments, the polyimide is selected from the group consisting of Nissan 7511L and SE 1211. In some embodiments, the presence of analyte is indicated by a non-ordered liquid crystal that appears white or bright when viewed through cross polar lenses and areas where analyte is not bound remain ordered and appear dark when viewed through cross polar lenses. In some embodiments, the presence of an analyte is indicated by a disordered liquid crystal that appears white or bright when viewed through cross polar lenses and areas where no analyte is bound maintain homeotropic orientation and appear dark. In some embodiments, the mesogens are selected from the group consisting of E7, MLC, 5CB (4-n-pentyl-4'-cyanobiphenyl), 8CB (4-cyano-4'octylbiphenyl), BL093, TL 216, ZLI 5800, MLC 6613, and MBBA ((p-methoxybenzylidene)-p-butylaniline). In some embodiments, the presence of an analyte on the second substrate is indicated by a difference in the orientation of the mesogens. In some embodiments, the difference in the orientation of the mesogens is detected by a method selected from the group consisting of visual detection, optical detection, spectroscopy, light transmission, and electrical detection. In some embodiments, the transferring step further comprises the step of eluting the analyte from the first substrate. In some embodiments, the methods further comprise the step of contacting the analyte-recognition moiety complex with a secondary binding agent. In some embodiments, the secondary binding agent is selected from the group consisting of an antigen binding protein, and enzyme, avidin, and biotin. In some embodiments, the presence of the secondary binding agent enhances the detection of the analyte after transfer to the second substrate. In some embodiments, the secondary binding agent is complexed with a lipid. In some embodiments, the secondary binding agent is displayed on a liposome.

In still further embodiments, the present invention provides kits comprising a) a first substrate displaying a recognition moiety, wherein the recognition moiety interacts with an analyte; b) a second substrate comprising a surface configured to receive the analyte interacting with the recognition moiety; c) a vial containing mesogens; and d) instructions for detecting the analyte. In some embodiments, the first substrate is selected from the group consisting of a stamp, a bead, and column media. In some embodiments, the stamp comprises PDMS. In some embodiments, the bead is a magnetic bead. In some embodiments, the column is an immunoaffinity column. In some embodiments, the recognition moiety is selected from the group consisting of a protein, polypeptide, peptide, nucleic acid, carbohydrate, lipid, organic molecule and inorganic molecule. In some embodiments, the mesogens are selected from the group consisting of E7, MLC, 5CB (4-n-pentyl-4'-cyanobiphenyl), 8CB (4-cyano-4'octylbiphenyl), BL093, TL 216, ZLI 5800, MLC 6613, and MBBA ((p-methoxybenzylidene)-p-butylaniline). In some embodiments, the second substrate comprises a functionalized surface. In some embodiments, the functionalized surface comprises a polyimide. In some embodiments, the polyimide is rubbed. In some embodiments, the polyimide is selected from the group consisting of Nissan 7210, Nissan 3510, Nissan 410, Nissan 3140, Nissan 5291, and Japan Synthetic Rubber JALS146-R19. In some embodiments, the polyimide homeotropically orients the liquid crystal. In some embodiments, the polyimide is selected from the group consisting of Nissan 7511L and SE 1211. In some embodiments, the kits further comprise a second vial comprising a secondary binding agent. In some embodiments, the secondary binding agent is selected from the group consisting of an antigen binding protein, an enzyme, avidin and biotin.

In still further embodiments, the present invention provides methods for detecting analytes comprising: a) providing: i) a sample suspected of containing of an analyte; ii) a detection device comprising a substrate comprising at least one electrode and at least one detection region; iii) mesogens; b) applying an electrical potential to the at least one electrode to transport the analyte to the substrate; and, c) contacting the substrate with the mesogens, wherein the presence of the analyte is indicated by a difference in alignment of the mesogens over the at least one detection region. In some embodiments, the electrical potential is an alternating current. In some embodiments, the transport occurs via dielectrophoresis. In some embodiments, the difference in the alignment of the mesogens is selected from the group consisting of a change in color, a change in texture, a change in tilt, and homeotropic orientation. In some embodiments, the difference in alignment of the mesogens is detected by a method selected from the group consisting of visual detection, optical detection, spectroscopy, light transmission, and electrical detection. In some embodiments, the analyte is selected from the group consisting of a protein, peptide, polypeptide, nucleic acid, organic molecule, inorganic molecule, virus, bacteria, liposome, cell, and fungus. In some embodiments, the substrate is selected from the group consisting of metal films, glass, silicon, diamond and polymeric materials. In some embodiments, the polymeric materials are selected from the group consisting of polyurethane, PDMS, polyimide, polystyrene, polycarbonate and polyisocyanoacrylate. In some embodiments, the mesogen is selected from the group consisting of E7, MLC, 5CB (4-n-pentyl-4'-cyanobiphenyl), 8CB (4-cyano-4'octylbiphenyl), BL093, TL 216, ZLI 5800, MLC 6613, and MBBA ((p-methoxybenzylidene)-p-butylaniline) and combinations thereof. In some embodiments, the detection region comprises a recognition moiety. In some embodiments, the recognition moiety is selected from the group consisting of an peptide, polypeptide, protein, nucleic acid, carbohydrate, organic molecule, and inorganic molecule. In some embodiments, the protein is an antigen binding protein. In some embodiments, the substrate comprises a plurality of detection regions. In some embodiments, the plurality of detection regions display the same recognition moiety. In some embodiments, the plurality of detection regions display different recognition moieties. In some embodiments, the detection device further comprises a second substrate arranged opposite the first substrate to form a cell. In some embodiments, the change in the mesogens is detected by viewing the detection device between cross polar lenses. In some embodiments, the sample is selected from the group consisting of biological fluids, tissue homogenates, feces, vesicular fluids, swabs of orifices or tissues, and media in which virus has been cultured or prepared. In some embodiments, the biological fluid is selected from the group consisting of cerebral-spinal fluid, urine, serum, plasma, nasal secretions, sputum, semen and saliva. In some embodiments, the methods further comprise the step of detecting analyte binding by measuring the impedance of the detection device, wherein a change in capacitance is indicative of analyte binding. In some embodiments, the impedance is capacitance or resistance. In some embodiments, the measuring is in real-time.

In still further embodiments, the present invention provides devices for detecting an analyte comprising a first substrate comprising at least one electrode and at least one detection region, wherein the at least one electrode is configured to provide an electrical potential to attract an analyte to the substrate and to determine the presence of the analyte by measuring electrical properties of the device, and a second substrate oriented opposite of the first substrate, wherein the first substrate and the second substrate form a chamber for containing a liquid crystal. In some embodiments, the electrical property is impedance. In some embodiments, the impedance is capacitance or resistance. In some embodiments, the impedance is capacitance. In some embodiments, the substrate is selected from the group consisting of metal films, glass, silicon, diamond and polymeric materials. In some embodiments, the polymeric materials are selected from the group consisting of polyurethane, PDMS, polyimide, polystyrene, polycarbonate and polyisocyanoacrylate. In some embodiments, the devices further comprise mesogens, wherein the mesogens are selected from the group consisting of E7, MLC, 5CB (4-n-pentyl-4'-cyanobiphenyl), 8CB (4-cyano-4'octylbiphenyl), BL093, TL 216, ZLI 5800, MLC 6613, and MBBA ((p-methoxybenzylidene)-p-butylaniline) and combinations thereof. In some embodiments, the detection region comprises a recognition moiety. In some embodiments, the recognition moiety is selected from the group consisting of a peptide, polypeptide, protein, nucleic acid, carbohydrate, organic molecule, and inorganic molecule. In some embodiments, the protein is an antigen binding protein. In some embodiments, the first substrate comprises a plurality of detection regions. In some embodiments, the plurality of detection regions display the same recognition moiety. In some embodiments, the plurality of detection regions display different recognition moieties. In some embodiments, the at least one electrode is selected from the group consisting of interdigitated, hyperbolic, triangular and rectangular electrodes. In some embodiments, the first substrate comprises at least two electrodes.

In still further embodiments, the present invention provides systems for detection of an analyte comprising the detection device described above and a readout device, the readout device comprising an opening configured to receive the detection device and an electrical circuit that contacts the at least one electrode when the detection device is in contact with the readout device. In some embodiments, the readout device interfaces with a computer processor. In some embodiments, the readout device comprises an electronic display. In some embodiments, the readout device comprises an LCD display. In some embodiments, the electric circuit is an oscillator circuit. In some embodiments, the oscillator circuit comprises a microprocessor. In some embodiments, the readout device comprises a microprocessor configured to measure electrical capacitance. In some embodiments, the readout device comprises a power source.

In still other embodiments, the present invention provides methods of detecting an analyte comprising: a) providing a sample suspected of containing an analyte, a substrate having a surface comprising polyimide, and mesogens; b) contacting the surface comprising polyimide with the sample suspected of containing an analyte; c) contacting the surface comprising polyimide with the mesogens, wherein the presence of the analyte is indicated by difference in the orientation of the mesogens. In some embodiments, the analyte non-specifically interacts with the surface comprising polyimide. In some embodiments, the surface comprising polyimide displays a recognition moiety. In some embodiments, the recognition moiety is selected from the group consisting of a protein, polypeptide, peptide, nucleic acid, carbohydrate, lipid, organic molecule and inorganic molecule. In some embodiments, the mesogens are selected from the group consisting of E7, MLC, 5CB (4-n-pentyl-4'-cyanobiphenyl), 8CB (4-cyano-4'octylbiphenyl), BL093, TL 216, ZLI 5800, MLC 6613, and MBBA ((p-methoxybenzylidene)-p-butylaniline). In some embodiments, the polyimide is rubbed. In some embodiments, the polyimide is selected from the group consisting of Nissan 7210, Nissan 3510, Nissan 410, Nissan 3140, Nissan 5291, and Japan Synthetic Rubber JALS146-R19. In some embodiments, the polyimide homeotropically orients the mesogens. In some embodiments, the polyimide is selected from the group consisting of Nissan 7511L and SE 1211. In some embodiments, the presence of analyte is indicated by a disordered liquid crystal that appears white or bright when viewed through cross polar lenses and areas where analyte is not bound remain ordered and appear dark when viewed through cross polar lenses. In some embodiments, the presence of an analyte is indicated by a disordered liquid crystal that appears white or bright when viewed through cross polar lenses and areas where no analyte is bound maintain homeotropic orientation and appear dark. In some embodiments, the homeotropic orientation of the liquid crystal is detected by a method selected from the group consisting of visual detection, optical detection, spectroscopy, light transmission, and electrical detection.

In some embodiments, the present invention provides methods of detecting binding interaction between a ligand and its binding partner comprising: a) providing a ligand and a binding partner, wherein at least one of the ligand molecule and the binding partner molecule are complexed with a lipid, and mesogens; b) contacting the ligand molecule and the binding partner molecule under conditions such that the ligand molecule and the binding partner molecule interact to form a ligand-binding partner complex; and c) detecting the ligand-binding partner complex by contacting the complex with mesogens. In some embodiments, the mesogens are homeotropically oriented by the complex. In some embodiments, the binding partner is recognition moiety. In some embodiments, the ligand is an analyte a sample. In some embodiments, the detecting step further comprises contacting the complex to a substrate prior to contacting with the mesogens. In some embodiments, the homeotropic alignment of the mesogens is detected by a method selected from the group consisting of visual detection, optical detection, spectroscopy, light transmission, and electrical detection. In some embodiments, the analyte is selected from the group consisting of a protein, peptide, polypeptide, nucleic acid, organic molecule, inorganic molecule, virus, bacteria, liposome, cell, and fungus. In some embodiments, the substrate is selected from the group consisting of metal films, glass, silicon, diamond and polymeric materials. In some embodiments, the polymeric materials are selected from the group consisting of polyurethane, PDMS, polyimide, polystyrene, polycarbonate and polyisocyanoacrylate. In some embodiments, the mesogen is selected from the group consisting of E7, MLC, 5CB (4-n-pentyl-4'-cyanobiphenyl), 8CB (4-cyano-4'octylbiphenyl), BL093, TL 216, ZLI 5800, MLC 6613, and MBBA ((p-methoxybenzylidene)-p-butylaniline) and combinations thereof. In some embodiments, the substrate comprises a detection region comprising a recognition moiety. In some embodiments, the recognition moiety is selected from the group consisting of a peptide, polypeptide, protein, nucleic acid, carbohydrate, organic molecule, and inorganic molecule. In some embodiments, the protein is an antigen binding protein. In some embodiments, the substrate comprises a plurality of detection regions. In some embodiments, the plurality of detection regions display the same recognition moiety. In some embodiments, the plurality of detection regions display different recognition moieties. In some embodiments, the ligand id biotin and the recognition moiety is avidin. In some embodiments, the at least one of the ligand molecule and the binding partner molecule complexed with a lipid is a secondary binding agent.

In some embodiments, the present invention provides kits for detecting an analyte comprising: a) a recognition moiety complexed with a lipid; b) a vial containing mesogens; and c) instructions for detecting the analyte. In some embodiments, the kits further comprise a substrate. In some embodiments, the recognition moiety is selected from the group consisting of a protein, polypeptide, peptide, nucleic acid, carbohydrate, organic molecule and inorganic molecule. In some embodiments, the substrate is selected from the group consisting of silicon, glass, polymer, diamond, and metal. In some embodiments, the substrate does not orient the liquid crystal. In some embodiments, the mesogens are selected from the group consisting of E7, MLC, 5CB (4-n-pentyl-4'-cyanobiphenyl), 8CB (4-cyano-4'octylbiphenyl), BL093, TL 216, ZLI 5800, MLC 6613, and MBBA ((p-methoxybenzylidene)-p-butylaniline).

In some embodiments, the present invention provides systems for detecting an analyte comprising: a) a recognition moiety complexed with a lipid; and b) a liquid crystal. In some embodiments, the systems further comprise a substrate. In some embodiments, the recognition moiety is selected from the group consisting of a protein, polypeptide, peptide, nucleic acid, carbohydrate, organic molecule and inorganic molecule. In some embodiments, the substrate is selected from the group consisting of silicon, glass, polymer, diamond, and metal. In some embodiments, the substrate does not orient the liquid crystal. In some embodiments, the mesogens are selected from the group consisting of E7, MLC, 5CB (4-n-pentyl-4'-cyanobiphenyl), 8CB (4-cyano-4'octylbiphenyl), BL093, TL 216, ZLI 5800, MLC 6613, and MBBA ((p-methoxybenzylidene)-p-butylaniline).

DESCRIPTION OF THE FIGURES

FIG. 2 provides photographs of transfers assays for the presence of West Nile Virus antibodies in positive horse and rabbit serum along with negative controls.

FIGS. 3a and 3b provide a schematic depiction of a device and preferred electrodes of the present invention.

FIG. 15 presents images of experiments in which labeled liposomes are used to report ligand binding.

DEFINITIONS

Figure 1:
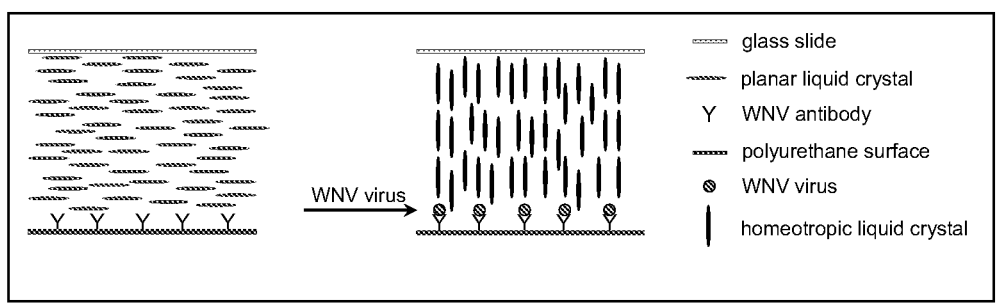
FIG. 1 provides a schematic view of an assay device of the present invention demonstrating homeotropic orientation of a liquid crystal directed by bound virus.
Figure 4:
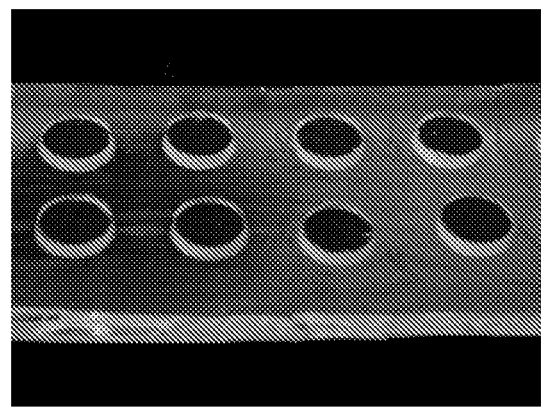
FIG. 4 is an image of a PDMS stamp of the present invention.

As used herein, the term "recognition moiety" refers to a composition of matter that interacts with an analyte of interest in either a covalent or noncovalent manner.

As used herein, the term "virus recognition moiety" refers to any composition of matter that binds specifically to a virus. Examples of "virus recognition moieties" include, but are not limited to antigen binding proteins and nucleic acid aptamers.

The term "substrate" refers to a composition that serves as a base for another composition such as recognition moiety. Examples of substrates include, but are not limited to, silicon surfaces, glass surfaces, glass beads, magnetic beads, agarose beads, etc.

As used herein, the term "ligand" refers to any molecule that binds to or can be bound by another molecule. A ligand is any ion, molecule, molecular group, or other substance that binds to another entity to form a larger complex. Examples of ligands include, but are not limited to, peptides, carbohydrates, nucleic acids, antibodies, or any molecules that bind to receptors.

As used herein, the term "homeotropic director" refers to a topographical feature (e.g., a nanostructure or homeotropic orienting polyimide) of a substrate that homeotropically orients a liquid crystal.

As used herein, the term "pathogen" refers to disease causing organisms, microorganisms, or agents including, but not limited to, viruses, bacteria, parasites (including, but not limited to, organisms within the phyla Protozoa, Platyhelminthes, Aschelminithes, Acanthocephala, and Arthropoda), fungi, and prions.

As used herein, the term "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. "Gram negative" and "gram positive" refer to staining patterns obtained with the Gram-staining process which is well known in the art (See e.g., Finegold and Martin, Diagnostic Microbiology, 6th Ed. (1982), CV Mosby St. Louis, pp 13-15).

As used herein, the term "lipid membrane" refers to, in its broadest sense, a thin sheet or layer comprising lipid molecules. It is intended that the term encompass all "biomembranes" (i.e., any organic membrane including, but not limited to, plasma membranes, nuclear membranes, organelle membranes, and synthetic membranes). Typically, membranes are composed of lipids, proteins, glycolipids, steroids, sterol and/or other components. As used herein, the term "membrane fragment" refers to any portion or piece of a membrane.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the phrase "lipid-based materials" refers to any material that contains lipids.

As used herein, the term "liposome" refers to artificially produced spherical lipid complexes that can be induced to segregate out of aqueous media.

As used herein, the term "secondary binding agent" refer to a molecule or collection of molecules that binds to one of an analyte-recognition moiety complex. It is contemplated that secondary binding agents are useful for amplifying the signal resulting from analyte-recognition moiety binding.

As used herein, the term "column media" refers to media used to fill a chromatography column, such as cationic exchange media, anionic exchange media, and immunoaffinity column media.

As used herein, the term "detection region" refers to a discreet area on substrate that is designated for detection of an analyte (e.g., a virus of interest) in a sample.

As used herein, the term "immobilization" refers to the attachment or entrapment, either chemically or otherwise, of a material to another entity (e.g., a solid support) in a manner that restricts the movement of the material.

As used herein, the terms "material" and "materials" refer to, in their broadest sense, any composition of matter.

As used herein the term "antigen binding protein" refers to a glycoprotein evoked in an animal by an immunogen (antigen) and to proteins derived from such glycoprotein (e.g., single chain antibodies and F(ab')2, Fab' and Fab fragments). An antibody demonstrates specificity to the immunogen, or, more specifically, to one or more epitopes contained in the immunogen. Native antibody comprises at least two light polypeptide chains and at least two heavy polypeptide chains. Each of the heavy and light polypeptide chains contains at the amino terminal portion of the polypeptide chain a variable region (i.e., VH and VL respectively), which contains a binding domain that interacts with antigen. Each of the heavy and light polypeptide chains also comprises a constant region of the polypeptide chains (generally the carboxy terminal portion) which may mediate the binding of the immunoglobulin to host tissues or factors influencing various cells of the immune system, some phagocytic cells and the first component (C1q) of the classical complement system. The constant region of the light chains is referred to as the "CL region," and the constant region of the heavy chain is referred to as the "CH region." The constant region of the heavy chain comprises a CH1 region, a CH2 region, and a CH3 region. A portion of the heavy chain between the CH1 and CH2 regions is referred to as the hinge region (i.e., the "H region"). The constant region of the heavy chain of the cell surface form of an antibody further comprises a spacer-transmembranal region (M1) and a cytoplasmic region (M2) of the membrane carboxy terminus. The secreted form of an antibody generally lacks the M1 and M2 regions.

As used herein, the term "selective binding" refers to the binding of one material to another in a manner dependent upon the presence of a particular molecular structure (i.e., specific binding). For example, an immunoglobulin will selectively bind an antigen that contains the chemical structures complementary to the ligand binding site(s) of the immunoglobulin. This is in contrast to "non-selective binding," whereby interactions are arbitrary and not based on structural compatibilities of the molecules.

As used herein, the term "polymerization" encompasses any process that results in the conversion of small molecular monomers into larger molecules consisting of repeated units. Typically, polymerization involves chemical crosslinking of monomers to one another.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope (i.e., the specific biochemical unit capable of causing an immune response).

As used herein, the terms "home testing" and "point of care testing" refer to testing that occurs outside of a laboratory environment. Such testing can occur indoors or outdoors at, for example, a private residence, a place of business, public or private land, in a vehicle, as well as at the patient's bedside.

As used herein, the term "virus" refers to minute infectious agents, which with certain exceptions, are not observable by light microscopy, lack independent metabolism, and are able to replicate only within a living host cell. The individual particles (i.e., virions) consist of nucleic acid and a protein shell or coat; some virions also have a lipid containing membrane. The term "virus" encompasses all types of viruses, including animal, plant, phage, and other viruses.

As used herein, term "nanostructures" refers to microscopic structures, typically measured on a nanometer scale. Such structures include various three-dimensional assemblies, including, but not limited to, liposomes, films, multi-layers, braided, lamellar, helical, tubular, and fiber-like shapes, and combinations thereof. Such structures can, in some embodiments, exist as solvated polymers in aggregate forms such as rods and coils. Such structures can also be formed from inorganic materials, such as prepared by the physical deposition of a gold film onto the surface of a solid, proteins immobilized on surfaces that have been mechanically rubbed, and polymeric materials that have been molded or imprinted with topography by using a silicon template prepared by electron beam lithography.

As used herein, the terms "self-assembling monomers" and "lipid monomers" refer to molecules that spontaneously associate to form molecular assemblies. In one sense, this can refer to surfactant molecules that associate to form surfactant molecular assemblies. The term "self-assembling monomers" includes single molecules (e.g., a single lipid molecule) and small molecular assemblies (e.g., polymerized lipids), whereby the individual small molecular assemblies can be further aggregated (e.g., assembled and polymerized) into larger molecular assemblies.

As used herein, the term "linker" or "spacer molecule" refers to material that links one entity to another. In one sense, a molecule or molecular group can be a linker that is covalent attached two or more other molecules (e.g., linking a ligand to a self-assembling monomer).

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., C—C). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (i.e., a chemical group derived from ammonia by replacement of one or more of its hydrogen atoms by hydrocarbon groups), a thiol group (i.e., sulfur analogs of alcohols), and an aldehyde group (i.e., the chemical group —CHO joined directly onto another carbon atom), respectively, and another atom or molecule.

As used herein, the term "covalent bond" refers to the linkage of two atoms by the sharing of two electrons, one contributed by each of the atoms.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "substrate" refers to a solid object or surface upon which another material is layered or attached. Solid supports include, but are not limited to, glass, metals, gels, and filter paper, among others.

As used herein, the terms "array" and "patterned array" refer to an arrangement of elements (i.e., entities) into a material or device. For example, combining several types of ligand binding molecules (e.g., antibodies or nucleic acids) into an analyte-detecting device, would constitute an array.

As used herein, the term "in situ" refers to processes, events, objects, or information that are present or take place within the context of their natural environment.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

As used herein, the term "liquid crystal" refers to a thermodynamic stable phase characterized by anisotropy of properties without the existence of a three-dimensional crystal lattice, generally lying in the temperature range between the solid and isotropic liquid phase.

As used herein, the term "mesogen" refers compounds that form liquid crystals, and in particular rigid rodlike or dislike molecules that are components of liquid crystalline materials.

As used herein, "thermotropic liquid crystal" refers to liquid crystals that result from the melting of mesogenic solids due to an increase in temperature. Both pure substances and mixtures form thermotropic liquid crystals.

"Lyotropic," as used herein, refers to molecules that form phases with orientational and/or positional order in a solvent. Lyotropic liquid crystals can be formed using amphiphilic molecules (e.g., sodium laurate, phosphatidylethanolamine, lecithin). The solvent can be water.

As used herein, the term "heterogenous surface" refers to a surface that orients liquid crystals in at least two separate planes or directions, such as across a gradient.

As used herein, "nematic" refers to liquid crystals in which the long axes of the molecules remain substantially parallel, but the positions of the centers of mass are randomly distributed. Nematic liquid crystals can be substantially oriented by a nearby surface.

"Chiral nematic," as used herein refers to liquid crystals in which the mesogens are optically active. Instead of the director being held locally constant as is the case for nematics, the director rotates in a helical fashion throughout the sample. Chiral nematic crystals show a strong optical activity that is much higher than can be explained on the bases of the rotatory power of the individual mesogens. When light equal in wavelength to the pitch of the director impinges on the liquid crystal, the director acts like a diffraction grating, reflecting most and sometimes all of the light incident on it. If white light is incident on such a material, only one color of light is reflected and it is circularly polarized. This phenomenon is known as selective reflection and is responsible for the iridescent colors produced by chiral nematic crystals.

"Smectic," as used herein refers to liquid crystals which are distinguished from "nematics" by the presence of a greater degree of positional order in addition to orientational order; the molecules spend more time in planes and layers than they do between these planes and layers. "Polar smectic" layers occur when the mesogens have permanent dipole moments. In the smectic A2 phase, for example, successive layers show anti ferroelectric order, with the direction of the permanent dipole alternating from layer to layer. If the molecule contains a permanent dipole moment transverse to the long molecular axis, then the chiral smectic phase is ferroelectric. A device utilizing this phase can be intrinsically bistable.

"Frustrated phases," as used herein, refers to another class of phases formed by chiral molecules. These phases are not chiral, however, twist is introduced into the phase by an array of grain boundaries. A cubic lattice of defects (where the director is not defined) exist in a complicated, orientationally ordered twisted structure. The distance between these defects is hundreds of nanometers, so these phases reflect light just as crystals reflect x-rays.

"Discotic phases" are formed from molecules that are disc shaped rather than elongated. Usually these molecules have aromatic cores and six lateral substituents. If the molecules are chiral or a chiral dopant is added to a discotic liquid crystal, a chiral nematic discotic phase can form.

DESCRIPTION OF THE INVENTION

The present invention relates to the field of detection of analytes, and in particular to detection of viruses, cells, bacteria, lipid-membrane containing organisms, proteins, nucleic acids, carbohydrates and other biomolecules, organic molecules and inorganic molecules using a liquid crystal assay format. Liquid crystal-based assay systems (LC assays) are described in U.S. Pat. No. 6,284,197; WO 01/61357; WO 01/61325; WO 99/63329; Gupta et al., Science 279:2077-2080 (1998); Seung-Ryeol Kim, Rahul R. Shah, and Nicholas L. Abbott; Orientations of Liquid Crystals on Mechanically Rubbed Films of Bovine Serum Albumin: A Possible Substrate for Biomolecular Assays Based on Liquid Crystals, Analytical Chemistry; 2000; 72(19); 4646-4653; Justin J. Skaife and Nicholas L. Abbott; Quantitative Interpretation of the Optical Textures of Liquid Crystals Caused by Specific Binding of Immunoglobulins to Surface-Bound Antigens, Langmuir; 2000; 16(7); 3529-3536; Vinay K. Gupta and Nicholas L. Abbott; Using proplets of Nematic Liquid Crystal To Probe the Microscopic and Mesoscopic Structure of Organic Surfaces, Langmuir; 1999; 15(21); 7213-7223; all of which are incorporated herein by reference.

The present invention provides systems, devices, and methods for both direct and indirect detection of analytes. The indirect detection systems utilize a first substrate comprising a recognition moiety that interacts with an analyte of interest, preferably specifically. After the first substrate is exposed to a sample suspected of containing an analyte, analyte interacting with the recognition moieties displayed on the first substrate are transferred to the second substrate. In preferred embodiments, the analyte interacts with the second substrate in a non-specific manner. In further preferred embodiments, the second substrate comprises a detection region that orients mesogens in liquid crystal. The second substrate is then contacted with a liquid crystal. A disordered liquid crystal is indicative of the presence of an analyte in the detection region.

WO 01/61357 describes the detection of viruses using liquid crystal based assays. These assays utilize a patterned detection region on a substrate that organizes mesogens in a homeotropic orientation. The assays are designed so that binding of a virus to the detection regions disrupts the homeotropic orientation.

Surprisingly, it has now been discovered that viral particles and other particles or organisms and cells having lipid membranes bound to a surface can homeotropically orient mesogens independent of any underlying topography pattern on the substrate. Thus, assay devices can be developed and manufactured without the time consuming and expensive stop of optimizing and fabricating nanostructured surfaces. Homeotropic alignment is observed in the present assays if the lipid membrane containing entity is either specifically or non-specifically bound to a substrate surface. The assays of the present invention can utilize a variety of recognition moieties to detect a wide variety of entities with lipid membranes in a wide variety of samples. Furthermore, the assays operate independent of temperature constraints. Thus, the assays of the present invention can be used to detect virtually any entity that comprises a lipid membrane that is accessible to mesogens in a liquid crystal.

In addition to entities with lipids membranes, which are listed below, the devices, systems and methods of the present invention are useful for detecting a variety of analytes, including, but not limited to, the following analytes: biomolecules including polypeptides (e.g., proteins), toxins, polynucleotides (e.g., RNA and DNA), carbohydrates, viruses, mycoplasmas, fungi, bacteria, and protozoa, especially Class A agents such as Variola major (smallpox), *Bacillus anthracis* (anthrax), *Yersinia pestis* (plague), *Clostridium botulinum* (botulism), *Francisella tularensis* (tularemia), Arenaviruses (Arenaviridae), Ebola hemorrhagic fever virus, Marburg hemorrhagic fever, Lassa fever virus, Junin and related viruses (Argentinian hemorrhagic fever virus, Bolivian hemorrhagic fever virus, Brazilian hemorrhagic fever virus, Venezuelan hemorrhagic fever virus), Dengue hemorrhagic fever virus, and toxins such as botulinum and Trichothecene (T2) mycotoxins; Class B agents such as *Coxiella burnetti* (Q fever), *Brucella* sp. (brucellosis), *Burkholderia mallei* (glanders), *Salmonella* sp., *Shigella dysenteria, Escherichia coli* strain O 157:H7, *Cryptosporidium parvum*, Alphaviruses (Togaviridae family) such as Venezuelan equine encephalitis virus, Eastern equine encephalitis virus, Western equine encephalitis virus, and toxins such as ricin toxin, epsilin toxin from *Clostridium* perfigens, and *Staphylococcus* enterotoxin B; and Class C agents such as mutlidrug resistant tuberculosis, Nipah virus, Hantaviruses, Tick-borne hemorrhagic fever viruses, Tick-borne encephalitis viruses, and Yellow fever virus. Other analytes include, but are not limited to, acids, bases, organic ions, inorganic ions, pharmaceuticals, herbicides, pesticides, chemical warfare agents, and noxious gases. These agents can be present as components in mixtures of structurally unrelated compounds, racemic mixtures of stereoisomers, non-racemic mixtures of stereoisomers, mixtures of diastereomers, mixtures of positional isomers or as pure compounds. The detection of these analytes, and specific substrates and recognition moieties for such detection, is described in more detail in co-pending application Ser. Nos. 10/227,974, 10/443,419, and 60/585,275; all of which are incorporated herein by reference in their entirety.

Accordingly, the present invention provides improved substrates and devices for the detection of analytes. For convenience, the description of the present invention is divided into the following sections: I. Recognition Moieties; II. Substrates; III. Functionalization of Substrates; IV. Mesogens; V. Direct Detection of Entities with Lipid Membranes; VI. Non-specific Detection Following Specific Capture; VII. Detection with Lipid Tags VIII. Kits.

I. Recognition Moieties

A variety of recognition moieties find use in the present invention. In preferred embodiments, the recognition moieties are immobilized on detection regions of the substrate (described in more detail below). In some embodiments of the present invention, a "recognition moiety" attached to or associated with the substrate is utilized to bind to or otherwise interact with another molecule or molecules (e.g., analytes). For example, in some embodiments, recognition moieties are attached to either ω-functionalized spacer arms or ω-functionalized SAM components which are in turn attached to or associated with the substrate. Furthermore, a recognition moiety can be presented by a polymer surface (e.g., a rubbed polymer surface).

In some preferred embodiments, the recognition moiety comprises an organic functional group. In presently preferred embodiments, the organic functional group is a member selected from the group consisting of amines, carboxylic acids, drugs, chelating agents, crown ethers, cyclodextrins or a combination thereof. In another preferred embodiment, the recognition moiety is a biomolecule. In still further preferred embodiments, the biomolecule is a protein, antigen binding protein, peptide, nucleic acid (e.g., single nucleotides or nucleosides, oligonucleotides, polynucleotides and single- and higher-stranded nucleic acids) or a combination thereof. In a presently preferred embodiment, the recognition moiety is biotin. In some embodiments, the recognition moieties are antigen binding proteins. Examples of antigen binding proteins finding use in the present invention include, but are not limited to, immunoglobulins, single chain antibodies, chimeric antibodies, polyclonal antibodies, monoclonal antibodies, and F(ab')2, Fab' and Fab fragments.

Various procedures known in the art may be used for the production of polyclonal antibodies. For the production of antibody, various host animals, including but not limited to rabbits, mice, rats, sheep, goats, etc., can be immunized by injection with the peptide corresponding to an epitope. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., *in Monoclonal Antibodies and Cancer Therapy*, Alan R. Liss, Inc., pp. 77-96 [1985]).

In addition, it is contemplated that techniques described for the production of single chain antibodies (U.S. Pat. No. 4,946,778; herein incorporated by reference) will find use in producing specific single chain antibodies that serve as recognition moieties. Furthermore, it is contemplated that any technique suitable for producing antibody fragments will find use in generating antibody fragments that are useful recognition moieties. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent. In still further embodiments, the recognition moiety comprises a phage displaying an antigen binding protein.

In some embodiments where the recognition moiety is a polynucleotide or polypeptide, a plurality of recognition moieties are arrayed on the substrates using photo activated chemistry, microcontact printing, and ink-jet printing. In particularly preferred embodiments, photolithography is utilized (See e.g., U.S. Pat. Nos. 6,045,996; 5,925,525; and 5,858,659; each of which is herein incorporated by reference). Using a series of photolithographic masks to define substrate exposure sites, followed by specific chemical synthesis steps, the process constructs high-density arrays of oligonucleotides, with each probe in a predefined position in the array. Multiple probe arrays are synthesized simultaneously on, for example, a large glass wafer. The wafers are then diced, and individual probe arrays are packaged in injection-molded plastic cartridges, which protect them from the environment and serve as chambers for hybridization.

In other embodiments, nucleic acid recognition moieties are electronically captured on a suitable substrate (See e.g., U.S. Pat. Nos. 6,017,696; 6,068,818; and 6,051,380; each of which are herein incorporated by reference). Through the use of microelectronics, this technology enables the active movement and concentration of charged molecules to and from designated test sites on its semiconductor microchip. DNA capture probes unique to a given target are electronically placed at, or "addressed" to, specific sites on the microchip. Since DNA has a strong negative charge, it can be electronically moved to an area of positive charge.

In still further embodiments, recognition moieties are arrayed on a suitable substrate by utilizing differences in surface tension (See e.g., U.S. Pat. Nos. 6,001,311; 5,985,551; and 5,474,796; each of which is herein incorporated by reference). This technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

In still further embodiments, recognition moieties are spotted onto a suitable substrate. Such spotting can be done by hand with a capillary tube or micropipette, or by an automated spotting apparatus such as those available from Affymetrix and Gilson (See e.g., U.S. Pat. Nos. 5,601,980; 6,242,266; 6,040,193; and 5,700,637; each of which is incorporated herein by reference).

When the recognition moiety is an amine, in preferred embodiments, the recognition moiety will interact with a structure on the analyte which reacts by binding to the amine (e.g., carbonyl groups, alkylhalo groups). In another preferred embodiment, the amine is protonated by an acidic moiety on the analyte of interest (e.g., carboxylic acid, sulfonic acid).

In certain preferred embodiments, when the recognition moiety is a carboxylic acid, the recognition moiety will interact with the analyte by complexation (e.g., metal ions). In still other preferred embodiments, the carboxylic acid will protonate a basic group on the analyte (e.g. amine).

In another preferred embodiment, the recognition moiety is a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In a preferred embodiment, the drug moieties are compounds that are being screened for their ability to interact with an analyte of choice. As such, drug moieties that are useful in practicing the instant invention include drugs from a broad range of drug classes having a variety of pharmacological activities.

Classes of useful agents include, for example, non-steroidal anti-inflammatory drugs (NSAIDS). The MAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniranune, triprolidine); antitussive drugs (e.g., dextromethorphan, codeine, carmiphen and carbetapentane); antipruritic drugs (e.g., methidilizine and trimeprizine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyraminde, quinidine, encamide); P-adrenergic blocker drugs (e.g., metoprolol, acebutolol, betaxolol, labetalol and timolol); cardiotonic drugs (e.g., milrinone, aminone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltazem, amiodarone, isosuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chlorprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazepam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole; pentamidine, gentamycin, kanamycin, lineomycin, methacycline, methenamine, minocycline, neomycin, netilmycin, paromomycin, streptomycin, tobramycin, miconazole, and amanfadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, a-2-interferon) anti-estrogens (e.g., tamoxifen), antimetabolites (e.g., fluorouracil, methotrexate, mercaptopurine, thioguanine).

The recognition moiety can also comprise hormones (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, dephenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progestogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful recognition moieties include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine $H_2$ antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

When the recognition moiety is a chelating agent, crown ether or cyclodextrin, host-guest chemistry will dominate the interaction between the recognition moiety and the analyte. The use of host-guest chemistry allows a great degree of recognition-moiety-analyte specificity to be engineered into a device of the invention. The use of these compounds to bind to specific compounds is well known to those of skill in the art. See, for example, Pitt et al. "The Design of Chelating Agents for the Treatment of Iron Overload," In, INORGANIC CHEMISTRY IN BIOLOGY AND MEDICINE; Martell, A. E., Ed.; American Chemical Society, Washington, D.C., 1980, pp. 279-312; Lindoy, L. F., THE CHEMISTRY OF MACROCYCLIC LIGAND COMPLEXES; Cambridge University Press, Cambridge, 1989; Dugas, H., BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, R. E., Whitaker, I. R., Eds., American Chemical Society, Washington, D.C., 1982, pp. 370-387; Kasina et al. *Bioconjugate Chem.* 9:108-117 (1998); Song et al., *Bioconjugate Chem.* 8:249-255 (1997).

In a presently preferred embodiment, the recognition moiety is a polyaminocarboxylate chelating agent such as ethylenediaminetetraacetic acid (EDTA) or diethylenetriaminepentaacetic acid (DTPA). These recognition moieties can be attached to any amine-terminated component of a SAM or a spacer arm, for example, by utilizing the commercially available dianhydride (Aldrich Chemical Co., Milwaukee, Wis.).

In still further preferred embodiments, the recognition moiety is a biomolecule such as a protein, nucleic acid, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments wherein the recognition moiety is a protein or antibody, the protein can be tethered to a SAM component or a spacer arm by any reactive peptide residue available on the surface of the protein. In preferred embodiments, the reactive groups are amines or carboxylates. In particularly preferred embodiments, the reactive groups are the e-amine groups of lysine residues. Furthermore, these molecules can be adsorbed onto the surface of the substrate or SAM by non-specific interactions (e.g., chemisorption, physisorption).

Recognition moieties that are antibodies can be used to recognize analytes which are proteins, peptides, nucleic acids, saccharides or small molecules such as drugs, herbicides, pesticides, industrial chemicals and agents of war. Methods of raising antibodies for specific molecules are well-known to those of skill in the art. See, U.S. Pat. Nos. 5,147, 786; 5,334,528; 5,686,237; 5,573,922; each of which is incorporated herein by reference. Methods for attaching antibodies to surfaces are also art-known (See, Delamarche et al. *Langmuir* 12:1944-1946 (1996)).

Peptides and nucleic acids can be attached to a SAM component or spacer arm. Both naturally-derived and synthetic peptides and nucleic acids are of use in conjunction with the present invention. These molecules can be attached to a SAM component or spacer arm by any available reactive group. For example, peptides can be attached through an amine, carboxyl, sulfhydryl, or hydroxyl group. Such a group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain (See, Chrisey et al. *Nucleic Acids Res.* 24:3031-3039 (1996)).

When the peptide or nucleic acid is a fully or partially synthetic molecule, a reactive group or masked reactive group can be incorporated during the process of the synthesis. Many derivatized monomers appropriate for reactive group incorporation in both peptides and nucleic acids are know to those of skill in the art (See, for example, THE PEPTIDES: ANALYSIS, SYNTHESIS, BIOLOGY, Vol. 2: "Special Methods in Peptide Synthesis," Gross, E. and Melenhofer, J., Eds., Academic Press, New York (1980)). Many useful monomers are commercially available (Bachem, Sigma, etc.). This masked group can then be unmasked following the synthesis, at which time it becomes available for reaction with a SAM component or a spacer arm.

In other preferred embodiments, the peptide is attached directly to the substrate (See, Frey et al. *Anal. Chem.* 68:3187-3193 (1996)). In a particularly preferred embodiment, the peptide is attached to a gold substrate through a sulfhydryl group on a cysteine residue. In another preferred embodiment, the peptide is attached through a thiol to a spacer arm which terminates in, for example, an iodoacetamide, chloroacetamide, benzyl iodide, benzyl bromide, alkyl iodide or alkyl bromide. Similar immobilization techniques are known to those of skill in the art (See, for example, Zull et al. *J. Ind Microbiol.* 13:137-143 (1994)).

In another preferred embodiment, the recognition moiety forms an inclusion complex with the analyte of interest. In a particularly preferred embodiment, the recognition moiety is a cyclodextrin or modified cyclodextrin. Cyclodextrins are a group of cyclic oligosaccharides produced by numerous microorganisms. Cyclodextrins have a ring structure which has a basket-like shape. This shape allows cyclodextrins to include many kinds of molecules into their internal cavity (See, for example, Szejtli, J., CYCLODEXTRINS AND THEIR INCLUSION COMPLEXES; Akademiai Klado, Budapest, 1982; and Bender et al., CYCLODEXTRIN CHEMISTRY, Springer-Verlag, Berlin, 1978).

Cyclodextrins are able to form inclusion complexes with an array of organic molecules including, for example, drugs, pesticides, herbicides and agents of war (See, Tenjarla et al., *J. Pharm. Sci.* 87:425-429 (1998); Zughul et al., *Pharm. Dev. Technol.* 3:43-53 (1998); and Albers et al., *Crit. Rev. Ther. Drug Carrier Syst.* 12:311-337 (1995)). Importantly, cyclodextrins are able to discriminate between enantiomers of compounds in their inclusion complexes. Thus, in one preferred embodiment, the invention provides for the detection of a particular enantiomer in a mixture of enantiomers (See, Koppenhoefer et al. *J. Chromatogr. A* 793:153-164 (1998)).

The cyclodextrin recognition moiety can be attached to a SAM component, through a spacer arm or directly to the substrate (See, Yamamoto et al., *J. Phys. Chem. B* 101:6855-6860 (1997)). Methods to attach cyclodextrins to other molecules are well known to those of skill in the chromatographic and pharmaceutical arts (See, Sreenivasan, *Appl. Polym. Sci.* 60:2245-2249 (1996)).

In other embodiments, the recognition moieties can be nucleic acids (e.g., RNA or DNA) or receptors that are specific for a particular entity (e.g., virus). In some embodiments, the nucleic acids are aptamers. The isolation of aptamers is described in U.S. Pat. Nos. 5,475,096; 5,270,163; and 5,475,096; and in PCT publications WO 97/38134, WO 98/33941, and WO 99/07724, all of which are herein incorporated by reference.

In some embodiments, recognition moieties are incorporated to detect a variety of bacteria and pathogens. Such recognition moieties include, but not limited to, sialic acid to detect HIV (Wies et al., Nature 333: 426 [1988]), influenza (White et al., Cell 56: 725 [1989]), chlamydia (Infect. 1 mm. 57: 2378 [1989]), reovirus, *Streptococcus suis, Salmonella*, Sendai virus, mumps, newcastle, myxovirus, and *Neisseria meningitidis;* 9-OAC sialic acid to detect coronavirus, encephalomyelitis virus, and rotavirus; non-sialic acid glycoproteins to detect cytomegalovirus (Virology 176: 337 [1990]) and measles virus (Virology 172: 386 [1989]); CD4 (Khatzman et al., Nature 312: 763 [1985]), vasoactive intestinal peptide (Sacerdote et al., J. of Neuroscience Research 18: 102 [1987]), and peptide T (Ruff et al., FEBS Letters 211: 17 [1987]) to detect HIV; epidermal growth factor to detect vaccinia (Epstein et al., Nature 318: 663 [1985]); acetylcholine receptor to detect rabies (Lentz et al., Science 215: 182 [1982]); Cd3 complement receptor to detect Epstein-Barr virus (Carel et al., J. Biol. Chem. 265: 12293 [1990]); β-adrenergic receptor to detect rheovirus (Co et al., Proc. Natl. Acad. Sci. 82: 1494 [1985]); ICAM-1 (Marlin et al., Nature 344: 70 [1990]), N-CAM, and myelin-associated glycoprotein MAb (Shephey et al., Proc. Natl. Acad. Sci. 85: 7743 [1988]) to detect rhinovirus; polio virus receptor to detect polio virus (Mendelsohn et al., Cell 56: 855 [1989]); fibroblast growth factor receptor to detect herpesvirus (Kaner et al., Science 248: 1410 [1990]); oligomannose to detect *Escherichia coli*; ganglioside $G_M1$ to detect *Neisseria meningitidis*; and antibodies to detect a broad variety of pathogens (e.g., *Neisseria gonorrhoeae, V. vulnificus, V. parahaemolyticus, V. cholerae, V. alginolyticus*, etc.).

In still further embodiments, the recognition moiety is a ligand that interacts with a binding partner. Examples of ligands include, but are not limited to, small organic molecules such as steroid molecules and small drug molecules, proteins, polypeptides and peptides, metal ions, and nucleic acids. In some embodiments, the ligand is recognized by a binding molecule in a sample. Examples of binding molecules include, but are not limited to, steroids, hormones, proteins, polypeptides, and peptides such immunoglobulin molecules and fragments thereof, nucleic acids, and other organic or non-organic molecules. In some preferred embodiments, the ligand is recognized by a binding molecule in a body fluid of a test subject. For example, the ligand can be a virus envelope protein or some other antigenic molecule from a pathogenic organism (such as those listed above). In preferred embodiments, the antigenic molecule (e.g., a protein) is recognized by an antibody molecule in the body fluid of a test subject that has been exposed to the pathogenic organism. In particularly preferred embodiments, the ligand is protein E from the envelope of West Nile Virus.

In some preferred embodiments, the ligands or recognition moieties are complexed with a lipid. The present invention contemplates complexation of the recognition moiety with a variety of lipids and lipid containing materials, including, but not limited to, fatty acids, phospholipids, mono-, di- and tri-glycerides comprising fatty acids and/or phospholipids, lipid bilayers, and liposomes. The lipid containing material can be provided as multilayers, as well as braided, lamellar, helical, tubular, and fiber-like shapes, and combinations thereof. Standard attachment chemistries are available for attaching a recognition moiety or ligand of interest to lipids and lipids containing materials. These attachment chemistries are described in more detail below with reference to liposomes.

In some preferred embodiments, the present invention utilizes liposomes. A variety of methods are useful for producing liposomes. Such methods are described in detail in numerous articles and have been reviewed in texts such as New (New, Liposomes: A Practical Approach, IRL Press, Oxford, [1989]), and Rosoff (Rosoff, Vesicles, Marcel Dekker, Inc., New York, [1996]) among others. See also, U.S. Pat. Nos. 6,183,772, 6,306,598, 6,180,784, 6,740,643, and 6,706,922, all of which are incorporated herein by reference, for methods of forming liposomes and other lipid containing materials. In some preferred embodiments, the liposomes are prepared using a probe sonication methods. Methods of derivatizing lipids with a diverse range of compounds (e.g., carbohydrates, proteins, nucleic acids, and other chemical groups) are well known in the art. The carboxylic acid on the terminal end of lipids can be easily modified to form esters, phosphate esters, amino groups, ammoniums, hydrazines, polyethylene oxides, amides, and many other compounds. These chemical groups provide linking groups for carbohydrates, proteins, nucleic acids, and other chemical groups (e.g., carboxylic acids can be directly linked to proteins by making the activated ester, followed by reaction to free amine groups on a protein to form an amide linkage). Examples of antibodies attached to Langmuir films are known in the art (See e.g., Tronin et al., Langmuir 11: 385 [1995]; and Vikhohn et al., Langmuir 12: 3276 [1996]). There are numerous other means to couple materials to membranes, or incorporate materials within a membrane, including for example, coupling of proteins or nucleic acids to polymer membranes (See e.g., Bamford et al. Adv. Mat. 6: 550 [1994]); coupling of proteins to self-assembled organic monolayers (See e.g., Willner et al., Adv. Mat. 5: 912 [1993]), and incorporating proteins into membranes (See e.g., Downer et al., Biosensor and Bioelect. 7: 429 [1992]); among others. Ligands (e.g. proteins, nucleic acids, and carbohydrates) can be conveniently attached to the derivatized lipids.

In some embodiments, ligands or recognition moieties are covalently linked to the head groups of lipid monomers. In other embodiments, ligands or recognition moieties are covalently linked to the surface of a lipid containing material (e.g., proteins and antibodies with multiple amine and thiol linkages to the material surface). In still other embodiments, ligands or recognition moieties are non-covalently incorporated into the biopolymeric material (e.g., ganglioside incorporated into the membrane of films and liposomes).

II. Substrates

Substrates that are useful in practicing the present invention can be made of practically any physicochemically stable material. In a preferred embodiment, the substrate material is non-reactive towards the constituents of the mesogenic layer. The substrates can be either rigid or flexible and can be either optically transparent or optically opaque. The substrates can be electrical insulators, conductors or semiconductors. Further, the substrates can be substantially impermeable to liquids, vapors and/or gases or, alternatively, the substrates can be permeable to one or more of these classes of materials. Exemplary substrate materials include, but are not limited to, inorganic crystals, inorganic glasses, inorganic oxides, metals, organic polymers and combinations thereof. In some embodiments, the substrates have microchannels therein for the delivery of sample and/or other reagents to the substrate surface or detection regions thereon. The design and use of microchannels are described, for example, in U.S. Pat. Nos. 6,425,972, 6,418,968, 6,447,727, 6,432,720, 5,976,336, 5,882,465, 5,876,675, 6,186,660, 6,100,541, 6,379,974, 6,267,858, 6,251,343, 6,238,538, 6,182,733, 6,068,752, 6,429,025, 6,413,782, 6,274,089, 6,150,180, 6,046,056, 6,358,387, 6,321,791, 6,326,083, 6,171,067, and 6167910, all of which are incorporated herein by reference.

A. Inorganic Crystal and Glasses

In some embodiments of the present invention, inorganic crystals and inorganic glasses are utilized as substrate materials (e.g., LiF, NaF, NaCl, KBr, KI, $CaF_2$, $MgF_2$, $HgF_2$, BN, $AsS_3$, ZnS, $Si_3N_4$ and the like). The crystals and glasses can be prepared by art standard techniques (See, e.g., Goodman, C. H. L., Crystal Growth Theory and Techniques, Plenum Press, New York 1974). Alternatively, the crystals can be purchased commercially (e.g., Fischer Scientific). The crystals can be the sole component of the substrate or they can be coated with one or more additional substrate components. Thus, it is within the scope of the present invention to utilize crystals coated with, for example one or more metal films or a metal film and an organic polymer. Additionally, a crystal can constitute a portion of a substrate which contacts another portion of the substrate made of a different material, or a different physical form (e.g., a glass) of the same material. Other useful substrate configurations utilizing inorganic crystals and/or glasses will be apparent to those of skill in the art.

B. Inorganic Oxides

In other embodiments of the present invention, inorganic oxides are utilized as the substrate. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. The inorganic oxides can be utilized in a variety of physical forms such as films, supported powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal).

In a presently preferred embodiment, the substrate is a rigid structure that is impermeable to liquids and gases. In this embodiment, the substrate consists of a glass plate onto which a metal, such as gold is layered by evaporative deposition. In a still further preferred embodiment, the substrate is a glass plate ($SiO_2$) onto which a first metal layer such as titanium has been layered. A layer of a second metal such as gold is then layered on top of the first metal layer.

C. Metals

In still further embodiments of the present invention, metals are utilized as substrates. The metal can be used as a crystal, a sheet or a powder. The metal can be deposited onto a backing by any method known to those of skill in the art including, but not limited to, evaporative deposition, sputtering, electroless deposition, electrolytic deposition and adsorption or deposition of preform particles of the metal including metallic nanoparticles.

Any metal that is chemically inert towards the mesogenic layer will be useful as a substrate in the present invention. Metals that are reactive or interactive towards the mesogenic layer will also be useful in the present invention. Metals that are presently preferred as substrates include, but are not limited to, gold, silver, platinum, palladium, nickel and copper. In one embodiment, more than one metal is used. The more than one metal can be present as an alloy or they can be formed into a layered "sandwich" structure, or they can be laterally adjacent to one another. In a preferred embodiment, the metal used for the substrate is gold. In a particularly preferred embodiment the metal used is gold layered on titanium.

The metal layers can be either permeable or impermeable to materials such as liquids, solutions, vapors and gases.

D. Organic Polymers

In still other embodiments of the present invention, organic polymers are utilized as substrate materials. Organic polymers useful as substrates in the present invention include polymers that are permeable to gases, liquids and molecules in solution. Other useful polymers are those that are impermeable to one or more of these same classes of compounds.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyethers and phenolic resins (See, Cognard, J. ALIGNMENT OF NEMATIC LIQUID CRYSTALS AND THEIR MIXTURES, in Mol. Cryst. Liq. Cryst. 1:1-74 (1982)). Presently preferred organic polymers include polydimethylsiloxane, polyethylene, polyacrylonitrile, cellulosic materials, polycarbonates and polyvinyl pyridinium.

In a presently preferred embodiment, the substrate is permeable and it consists of a layer of gold, or gold over titanium, which is deposited on a polymeric membrane, or other material, that is permeable to liquids, vapors and/or gases. The liquids and gases can be pure compounds (e.g., chloroform, carbon monoxide) or they can be compounds which are dispersed in other molecules (e.g., aqueous protein solutions, herbicides in air, alcoholic solutions of small organic molecules). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane and track etched polycarbonate membranes.

In a further preferred embodiment, the layer of gold on the permeable membrane is itself permeable. In a still further preferred embodiment, the permeable gold layer has a thickness of about 70 Angstroms or less.

In those embodiments wherein the permeability of the substrate is not a concern and a layer of a metal film is used, the film can be as thick as is necessary for a particular application. For example, if the film is used as an electrode, the film can be thicker than in an embodiment in which it is necessary for the film to be transparent or semi-transparent to light.

Thus, in a preferred embodiment, the film is of a thickness of from about 0.01 nanometer to about 1 micrometer. In a further preferred embodiment, the film is of a thickness of from about 5 nanometers to about 100 nanometers. In yet a further preferred embodiment, the film is of a thickness of from about 10 nanometers to about 50 nanometers.

E. Formats

The substrates of the present invention are provided in a variety of formats. For examples, the substrates may present planar or curved surfaces or be beads. The bead format is especially useful for the indirect detection methods described below. The bead substrates of the present invention may comprise any of the substrate materials described above. In some preferred embodiments, the beads are commercially available beads such as agarose beads, acrylic beads, or latex beads. In some embodiments, the beads are magnetic. In still other embodiments, the beads are coated with a metal such as silver or gold. In still other embodiments, substrates such column chromatography media may be used to capture analytes. Examples of such substrates include immunoaffinity columns (i.e., columns containing media functionalized with antigen binding proteins), protein-A affinity columns, cation exchange columns such as S-SEPHAROSE, SP-SEPHAROSE, and carboxymethyl cellulose, anion exchange columns such as DEAE Cellulose, QAE SEPHADEX, and FAST Q SEPHAROSE, sizing columns such as ULTRAGEL columns, phsosphocelluse columns, heparin sulfate columns, and the like. Following elution for the columns analytes are detected as described in detail below.

III. Functionalization of Substrates

In some embodiments, the surface of the substrate is functionalized so that a recognition moiety is immobilized on the surface of the substrate. In some embodiments, the immobilized recognition moiety forms a detection region. In some embodiments, a plurality of detection regions are formed on the surface of the substrate. In some embodiments, the same recognition moiety is provided on two or more of the plurality of detection regions, while in other embodiments, at least two different recognition moieties are immobilized on one or more of the plurality of detection regions. In some embodiments, the recognition moieties are arrayed in discreet detection regions on the substrate surfaces by the methods described in more detail below.

A. Self-Assembled Monolayers

In some embodiments, the surface of the substrate is first functionalized by forming a self-assembled monolayer (SAM) on the substrate surface. Self-assembled monolayers are generally depicted as an assembly of organized, closely packed linear molecules. There are two widely-used methods to deposit molecular monolayers on solid substrates: Langmuir-Blodgett transfer and self-assembly. Additional methods include techniques such as depositing a vapor of the monolayer precursor onto a substrate surface and the layer-by-layer deposition of polymers and polyelectrolytes from solution (Ladam et al., Protein Adsorption onto Auto-Assembled Polyelectrolyte Films, Langmuir; 2001; 17(3); 878-882).

The composition of a layer of a SAM useful in the present invention can be varied over a wide range of compound structures and molar ratios. In one embodiment, the SAM is formed from only one compound. In a presently preferred embodiment, the SAM is formed from two or more components. In another preferred embodiment, when two or more components are used, one component is a long-chain hydrocarbon having a chain length of between 10 and 25 carbons and a second component is a short-chain hydrocarbon having a chain length of between 1 and 9 carbon atoms. In particularly preferred embodiments, the SAM is formed from $CH_3(CH_2)_{15}SH$ and $CH_3(CH_2)_4SH$ or $CH_3(CH_2)_{15}SH$ and $CH_3$ $(CH_2)_9SH$. In any of the above described embodiments, the carbon chains can be functionalized at the $\omega$-terminus (e.g., $NH_2$, COOH, OH, CN), at internal positions of the chain (e.g., aza, oxa, thia) or at both the $\omega$-terminus and internal positions of the chain.

A recognition moiety can be attached to the surface of a SAM by any of a large number of art-known attachment methods. In one preferred embodiment, a reactive SAM component is attached to the substrate and the recognition moiety is subsequently bound to the SAM component via the reactive group on the component and a group of complementary reactivity on the recognition moiety (See, e.g., Hegner et al. Biophys. J. 70:2052-2066 (1996)). In another preferred embodiment, the recognition moiety is attached to the SAM component prior to immobilizing the SAM component on the substrate surface: the recognition moiety-SAM component cassette is then attached to the substrate. In a still further preferred embodiment, the recognition moiety is attached to the substrate via a displacement reaction. In this embodiment, the SAM is preformed and then a fraction of the SAM components are displaced by a recognition moiety or a SAM component bearing a virus recognition moiety. In still other embodiments, the polypeptide recognition moieties are adsorbed directly onto hydrophobic monolayers such as $CH_3$ $(CH_2)_{15}SH$. In embodiments where the recognition moiety is an antibody or other molecule that binds to protein A, protein A is first attached to the monolayer followed by the antibody, which is bound by protein A.

B. Functionalized SAMs

The discussion which follows focuses on the attachment of a reactive SAM component to the substrate surface. This focus is for convenience only and one of skill in the art will understand that the discussion is equally applicable to embodiments in which the SAM component-recognition moiety is preformed prior to its attachment to the substrate. As used herein, "reactive SAM components" refers to components that have a functional group available for reaction with a recognition moiety or other species following the attachment of the component to the substrate.

Currently favored classes of reactions available with reactive SAM components are those that proceed under relatively mild conditions. These include, but are not limited to nucleophilic substitutions (e.g., reactions of amines and alcohols with acyl halides), electrophilic substitutions (e.g., enamine reactions) and additions to carbon-carbon and carbon-heteroatom multiple bonds (e.g., Michael reaction, Diels-Alder addition). These and other useful reactions are discussed in March, ADVANCED ORGANIC CHEMISTRY, Third Ed., John Wiley & Sons, New York, 1985.

According to the present invention, a substrate's surface is functionalized with SAM, components and other species by covalently binding a reactive SAM component to the substrate surface in such a way as to derivatize the substrate surface with a plurality of available reactive functional groups. Reactive groups which can be used in practicing the present invention include, for example, amines, hydroxyl groups, carboxylic acids, carboxylic acid derivatives, alkenes, sulfhydryls, siloxanes, etc.

A wide variety of reaction types are available for the functionalization of a substrate surface. For example, substrates constructed of a plastic such as polypropylene, can be surface derivatized by chromic acid oxidation, and subsequently converted to hydroxylated or aminomethylated surfaces. Substrates made from highly crosslinked divinylbenzene can be surface derivatized by chloromethylation and subsequent functional group manipulation. Additionally, functionalized substrates can be made from etched, reduced polytetrafluoroethylene.

When the substrates are constructed of a siliaceous material such as glass, the surface can be derivatized by reacting the surface Si—OH, Si0-H, and/or Si—Si groups with a functionalizing reagent. When the substrate is made of a metal film, the surface can be derivatized with a material displaying avidity for that metal.

In a preferred embodiment, wherein the substrates are made from glass, the covalent bonding of the reactive group to the glass surface is achieved by conversion of groups on the substrate's surface by a silicon modifying reagent such as:

  (1)

where R is an alkyl group, such as methyl or ethyl, $R^1$ is a linking group between silicon and X and X is a reactive group or a protected reactive group. The reactive group can also be a recognition moiety as discussed below. Silane derivatives having halogens or other leaving groups beside the displayed alkoxy groups are also useful in the present invention.

A number of siloxane functionalizing reagents can be used, for example:
1. Hydroxyalkyl siloxanes (Silylate surface, functionalize with diborane, and $H_2O_2$ to oxidize the alcohol)
    a. allyl trichlorosilane→→3-hydroxypropyl
    b. 7-oct-1-enyl trichlorosilane→→8-hydroxyoctyl
2. Diol (dihydroxyalkyl) siloxanes (silylate surface and hydrolyze to diol)
    a. (glycidyl trimethoxysilane→→(2,3-dihydroxypropyloxy)propyl
3. Aminoalkyl siloxanes (amines requiring no intermediate functionalizing step).
    a. 3-aminopropyl trimethoxysilane→aminopropyl
4. Dimeric secondary aminoalkyl siloxanes
    a. bis(3-trimethoxysilylpropyl) amine→bis(silyloxylpropyl)amine.

It will be apparent to those of skill in the art that an array of similarly useful functionalizing chemistries are available when SAM components other than siloxanes are used. Thus, for example similarly functionalized alkyl thiols can be attached to metal films and subsequently reacted to produce the functional groups such as those exemplified above.

In another preferred embodiment, the substrate is at least partially a metal film, such as a gold film, and the reactive group is tethered to the metal surface by an agent displaying avidity for that surface. In a presently preferred embodiment, the substrate is at least partially a gold film and the group which reacts with the metal surface comprises a thiol, sulfide or disulfide such as:

  (2)

$R^2$ is a linking group between sulfur and $X^2$ and $X^2$ is a reactive group or a protected reactive group. $X^2$ can also be a recognition moiety as discussed below. Y is a member selected from the group consisting of H, $R^3$ and $R^3$—S—, wherein $R^2$ and $R^3$ are independently selected. When $R^2$ and $R^3$ are the same, symmetrical sulfides and disulfides result, and when they are different, asymmetrical sulfides and disulfides result.

A large number of functionalized thiols, sulfides and disulfides are commercially available (Aldrich Chemical Co., St. Louis). Additionally, those of skill in the art have available to them a manifold of synthetic routes with which to produce additional such molecules. For example, amine-functionalized thiols can be produced from the corresponding haloamines, halo-carboxylic acids, etc. by reaction of these halo precursors with sodium sulfhydride. See, e.g., Reid, ORGANIC CHEMISTRY of BIVALENT SULFUR, VOL 1, pp. 21-29, 32-35, vol. 5, pp. 27-34, Chemical Publishing Co., New York, 1.958, 1963. Additionally, functionalized sulfides can be prepared via alkylthio-de-halogenation with a mercaptan salt (See, Reid, ORGANIC CHEMISTRY OF BIVALENT SULFUR, vol. 2, pp. 16-21, 24-29, vol. 3, pp. 11-14, Chemical Publishing Co., New York, 1960). Other methods for producing compounds useful in practicing the present invention will be apparent to those of skill in the art.

In another preferred embodiment, the functionalizing reagent provides for more than one reactive group per each reagent molecule. Using reagents such as Compound 3, below, each reactive site on the substrate surface is, in essence, "amplified" to two or more functional groups:

  (3)

where R is an alkyl group, such as methyl, $R^2$ is a linking group between silicon and $X^2$, $X^2$ is a reactive group or a protected reactive group and n is an integer between 2 and 50, and more preferably between 2 and 20.

Similar amplifying molecules are also of use in those embodiments wherein the substrate is at least partially a metal film. In these embodiments the group which reacts with the metal surface comprises a thiol, sulfide or disulfide such as in Formula (4):

  (4)

As discussed above, $R^2$ is a linking group between sulfur and $X^2$ and $X^2$ is a reactive group or a protected reactive group. $X^2$ can also be a recognition moiety. Y is a member selected from the group consisting of H, $R^3$ and $R^3$—S—, wherein $R^2$ and $R^3$ are independently selected.

R groups of use for $R^1$, $R^2$ and $R^3$ in the above described embodiments of the present invention include, but are not limited to, alkyl, substituted alkyl, aryl, arylalkyl, substituted aryl, substituted arylalkyl, acyl, halogen, hydroxy, amino, alkylamino, acylamino, alkoxy, acyloxy, aryloxy, aryloxyalkyl, mercapto, saturated cyclic hydrocarbon, unsaturated cyclic hydrocarbon, heteroaryl, heteroarylalkyl, substituted heteroaryl, substituted heteroarylalkyl, heterocyclic, substituted heterocyclic and heterocyclicalkyl groups.

In each of Formulae 1-4, above, each of $R^1$, $R^2$ and $R^3$ are either stable or they can be cleaved by chemical or photochemical reactions. For example, R groups comprising ester or disulfide bonds can be cleaved by hydrolysis and reduction, respectively. Also within the scope of the present invention is the use of R groups which are cleaved by light such as, for example, nitrobenzyl derivatives, phenacyl groups, benzoin esters, etc. Other such cleaveable groups are well-known to those of skill in the art.

In another preferred embodiment, the organosulfur compound is partially or entirely halogenated. An example of compounds useful in this embodiment include:

  (5)

wherein, $X^1$ is a member selected from the group consisting of H, halogen reactive groups and protected reactive groups. Reactive groups can also be recognition moieties as discussed below. Q, $Q^1$ and $Q^2$ are independently members selected from the group consisting of H and halogen. $Z^1$ is a member selected from the group consisting of —$CQ_2$—, —$CQ^1_2$—, —$CQ^2_2$—, —O—, —S—, $NR^4$—, —C(O)$NR^4$ and $R^4$NC (O0-, in which $R^4$ is a member selected from the group consisting of H, alkyl, substituted alkyl, aryl, substituted aryl, heteroaryl and heterocyclic groups and m and n are independently a number between 0 and 40.

In yet another preferred embodiment, the organic layer comprises a compound according to Formula 5 above, in which Q, $Q^1$ and $Q^2$ are independently members selected from the group consisting of H and fluorine. In a still further preferred embodiment, the organic layer comprises compounds having a structure according to Formulae (6) and (7):

$$CF_3(CF_2)_m Z^1 (CH_2)_n SH \quad (6)$$

$$CF_3(CF_2)_o Z^2 (CH_2)_p SH \quad (7)$$

wherein, $Z^1$ and $Z^2$ are members independently selected from the group consisting of —$CH_2$—, —O—, —S—, $NR^4$, —C(O)$NR^4$ and $R^4$NC(O)— in which $R^4$ is a member selected from the group consisting of H, alkyl, substituted alkyl, aryl, substituted aryl, heteroaryl and heterocyclic groups. In a presently preferred embodiment, the Z groups of adjacent molecules participate in either an attractive (e.g., hydrogen bonding) or repulsive (e.g., van der Waals) interaction.

In Formula 7, m is a number between 0 and 40, n is a number between 0 and 40, o is a number between 0 and 40 and p is a number between 0 and 40.

In a further preferred embodiment, the compounds of Formulae 6 and 7 are used in conjunction with an organosulfur compound, either halogentated or unhalogenated, that bears a recognition moiety.

When the organic layer is formed from a halogenated organosulfur compound, the organic layer can comprise a single halogenated compound or more than one halogenated compound having different structures. Additionally, these layers can comprise a non-halogenated organosulfur compound.

The reactive functional groups ($X^1$ and $X^2$) are, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups which can be converted to disulfides or reacted with acyl halides;

(h) amine or sulfhydryl groups which can be, for example, acylated or alkylated;

(i) alkenes which can undergo, for example, cycloadditions, acylation, Michael addition, etc; and (j) epoxides which can react with, for example, amines and hydroxyl compounds.

The reactive moieties can also be recognition moieties. The nature of these groups is discussed in greater detail below.

The reactive functional groups can be chosen such that they do not participate in, or interfere with, the reaction controlling the attachment of the functionalized SAM component onto the substrate's surface. Alternatively, the reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

In a preferred embodiment, the SAM component bearing the recognition moiety is attached directly and essentially irreversibly via a "stable bond" to the surface of the substrate. A "stable bond", as used herein, is a bond which maintains its chemical integrity over a wide range of conditions (e.g., amide, carbamate, carbon-carbon, ether, etc.). In another preferred embodiment, the SAM component bearing the recognition moiety is attached to the substrate surface by a "cleaveable bond". A "cleaveable bond", as used herein, is a bond that is designed to undergo scission under conditions which do not degrade other bonds in the recognition moiety-analyte complex. Cleaveable bonds include, but are not limited to, disulfide, imine, carbonate and ester bonds.

In certain embodiments, it is advantageous to have the recognition moiety attached to a SAM component having a structure that is different than that of the constituents of the bulk SAM. In this embodiment, the group to which the recognition moiety is bound is referred to as a "spacer arm" or "spacer." Using such spacer arms, the properties of the SAM adjacent to the recognition moiety can be controlled. Properties that are usefully controlled include, for example, hydrophobicity, hydrophilicity, surface-activity and the distance of the recognition moiety from the plane of the substrate and/or the SAM. For example, in a SAM composed of alkanethiols, the recognition moiety can be attached to the substrate or the surface of the SAM via an amine terminated poly(ethyleneglycol). Numerous other combinations of spacer arms and SAMs are accessible to those of skill in the art.

The hydrophilicity of the substrate surface can be enhanced by reaction with polar molecules such as amine-, hydroxyl- and polyhydroxylcontaining molecules. Representative examples include, but are not limited to, polylysine, polyethyleneimine, poly(ethyleneglycol) and poly(propyleneglycol). Suitable functionalization chemistries and strategies for these compounds are known in the art (See, for example, Dunn, R. L., et al., Eds. POLYMERIC DRUGS AND DRUG DELIVERY SYSTEMS, ACS Symposium Series Vol. 469, American Chemical Society, Washington, D.C. 1991).

The hydrophobicity of the substrate surface can be modulated by using a hydrophobic spacer arm such as, for example, long chain diamines, long chain thiols, α, ω-amino acids, etc. Representative hydrophobic spacers include, but are not limited to, 1,6-hexanediamine, 1,8-octanediamine, 6-aminohexanoic acid and 8-aminooctanoic acid.

The substrate surface can also be made surface-active by attaching to the substrate surface a spacer which has surfactant properties. Compounds useful for this purpose include, for example, aminated or hydroxylated detergent molecules such as, for example, 1-aminododecanoic acid.

In another embodiment, the spacer serves to distance the virus recognition moiety from the substrate or SAM. Spacers with this characteristic have several uses. For example, a recognition moiety held too closely to the substrate or SAM surface may not react with incoming analyte, or it may react unacceptably slowly. When an analyte is itself sterically demanding, the reaction leading to recognition moiety-analyte complex formation can be undesirably slowed, or not occur at all, due to the monolithic substrate hindering the approach of the two components.

In another embodiment, the physicochemical characteristics (e.g., hydrophobicity, hydrophilicity, surface activity, conformation) of the substrate surface and/or SAM are altered by attaching a monovalent moiety which is different in composition than the constituents of the bulk SAM and which does not bear a recognition moiety. As used herein, "monovalent moiety" refers to organic molecules with only one reactive functional group. This functional group attaches the molecule to the substrate. "Monovalent moieties" are to be contrasted with the bifunctional "spacer" groups described above. Such monovalent groups are used to modify the hydrophilicity, hydrophobicity, binding characteristics, etc. of the substrate surface. Examples of groups useful for this purpose include long chain alcohols, amines, fatty acids, fatty acid derivatives, poly(ethyleneglycol) monomethyl ethers, etc.

When two or more structurally distinct moieties are used as components of the SAMs, the components can be contacted with the substrate as a mixture of SAM components or, alternatively, the components can be added individually. In those embodiments in which the SAM components are added as a mixture, the mole ratio of a mixture of the components in solution results in the same ratio in the mixed SAM. Depending on the manner in which the SAM is assembled, the two components do not phase segregate into islands (See, Bain and Whitesides, *J. Am. Chem. Soc.* 111:7164 (1989)). This feature of SAMs can be used to immobilize recognition moieties or bulky modifying groups in such a manner that certain interactions, such as steric hindrance, between these molecules is minimized.

The individual components of the SAMs can also be bound to the substrate in a sequential manner. Thus, in one embodiment, a first SAM component is attached to the substrate's surface by "underlabeling" the surface functional groups with less than a stoichiometric equivalent of the first component. The first component can be a SAM component liked to a terminal reactive group or recognition group, a spacer arm or a monovalent moiety. Subsequently, the second component is contacted with the substrate. This second component can either be added in stoichiometric equivalence, stoichiometric excess or can again be used to underlabel to leave sites open for a third component.

C. Polyimides

In some embodiments, the substrates are coated with polyimide layer. It is contemplated that polyimide coated substrates are especially useful because in some instances, the surfaces homeotropically orient a liquid crystal, while in other instances the surfaces can be rubbed to provide an anisotropic surface for orient a liquid crystal. In preferred embodiments, a substrate such as a silicon wafer is coated with a polyimide. In preferred embodiment, the substrate is spin coated with the polyimide. A variety of polyimides find use with the present invention, including, but not limited to Nissan 7210, Nissan 3510, Nissan 410, Nissan 3140, Nissan 5291, and Japan Synthetic Rubber JALS 146-R19 for planar alignment of liquid crystals and Nissan 7511L and SE 1211 for homeotropic orientation of liquid crystals. Surprising, it has been found that the ability of rubbed polyimide surfaces to orient liquid crystals is maintained when a recognition moiety is displayed on the rubbed surface, and then masked when an analyte binds the recognition moiety. Thus, areas where an analyte is bound have a non-ordered liquid crystal and appear white or bright when viewed through cross polars and areas where analyte is not bound remain ordered and appear dark when viewed through cross polars. Surprising, it has also been found that polyimide surfaces that homeotropically orient liquid crystals can be used to report non-specific binding to the surface. In these embodiments, areas where an analyte is bound have a disordered liquid crystal appear white or bright when viewed through cross polars and areas where no analyte is bound maintain the homeotropic orientation and appear dark. These different polyimides provide different anchoring properties and different binding affinity to different proteins which can be used to probe and report the binding events between the proteins. Likewise, different liquid crystals show different response to the specific binding event. Therefore, it is possible to tune the assays by using different liquid crystalline materials such as, 5CB, BL093, TL 216, ZLI 5800, MLC 6613, and (p-methoxybenzylidene)-p-butylaniline (MBBA) with different optical and dielectric properties.

D. Direct Adsorption

In some embodiments, the recognition moiety is immobilized on a substrate by direct adsorption. For example, an antibody can be immobilized onto a thin film of polyurethane spin coated onto a gold substrate surface.

E. Arrays

In some embodiments where the virus recognition moiety is a polynucleotide or polypeptide, a plurality of virus recognition moieties are arrayed on the substrates using photo activated chemistry, microcontact printing, and ink-jet printing. In particularly preferred embodiments, photolithography is utilized (See e.g., U.S. Pat. Nos. 6,045,996; 5,925,525; and 5,858,659; each of which is herein incorporated by reference). Using a series of photolithographic masks to define substrate exposure sites, followed by specific chemical synthesis steps, the process constructs high-density arrays of oligonucleotides, with each probe in a predefined position in the array. Multiple probe arrays are synthesized simultaneously on, for example, a large glass wafer. The wafers are then diced, and individual probe arrays are packaged in injection-molded plastic cartridges, which protect them from the environment and serve as chambers for hybridization.

In other embodiments, nucleic acid virus recognition moieties are electronically captured on a suitable substrate (See e.g., U.S. Pat. Nos. 6,017,696; 6,068,818; and 6,051,380; each of which are herein incorporated by reference). Through the use of microelectronics, this technology enables the active movement and concentration of charged molecules to and from designated test sites on its semiconductor microchip. DNA capture probes unique to a given target are electronically placed at, or "addressed" to, specific sites on the microchip. Since DNA has a strong negative charge, it can be electronically moved to an area of positive charge.

In still further embodiments, virus recognition moieties are arrayed on a suitable substrate by utilizing differences in surface tension (See e.g., U.S. Pat. Nos. 6,001,311; 5,985,551; and 5,474,796; each of which is herein incorporated by reference). This technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a X/Y translation stage under a set of four piezoelectric nozzles, one for each of the four standard DNA bases. The translation stage moves along each of the rows of the array and the appropriate reagent is delivered to each of the reaction site. For example, the A amidite is delivered only to the sites where amidite A is to be coupled during that synthesis step and so on. Common reagents and washes are delivered by flooding the entire surface and then removing them by spinning.

In still further embodiments, virus recognition moieties are spotted onto a suitable substrate. Such spotting can be done by hand with a capillary tube or micropipette, or by an automated spotting apparatus such as those available from Affymetrix and Gilson (See e.g., U.S. Pat. Nos. 5,601,980; 6,242,266; 6,040,193; and 5,700,637; each of which is incorporated herein by reference).

E. Blocking

In some embodiments, following immobilization of the recognition moiety on the surface of the substrate, the remainder of the substrate is blocked to guard against non-specific binding to the substrate surface. Examples of suitable blocking agents, include, but are not limited to, serum albumins, zwitterionic polymers, adsorbed lipid layers, dextran and other sugars, cross-linked lipids, polyethylene oxide, polyoxazolines, hydrogels, and milk. In preferred embodiments, the blocking agent bovine serum albumin, human serum albumin or equine serum albumin.

IV. Mesogens

Any compound or mixture of compounds which forms a mesogenic layer can be used in conjunction with the present invention. The mesogens can form thermotropic or lyotropic liquid crystals. Both the thermotropic and lyotropic liquid crystals can exist in a number of forms including nematic, chiral nematic, smectic, polar smectic, chiral smectic, frustrated phases and discotic phases.

TABLE 1

Molecular structure of mesogens suitable for use in Liquid Crystal Assay Devices

| Mesogen | Structure |
|---|---|
| Anisaldazine | $CH_3-O-\text{\textlangle}\bigcirc\text{\textrangle}-CH=N-N=CH-\text{\textlangle}\bigcirc\text{\textrangle}-O-CH_3$ |
| NCB | $C_nH_{2n+1}-\text{\textlangle}\bigcirc\text{\textrangle}-\text{\textlangle}\bigcirc\text{\textrangle}-CN$ |
| CBOOA | $C_9H_{19}-O-\text{\textlangle}\bigcirc\text{\textrangle}-N=CH-\text{\textlangle}\bigcirc\text{\textrangle}-CN$ |
| Comp A | $C_7H_{15}-\text{\textlangle}\bigcirc\text{\textrangle}-\text{\textlangle}\bigcirc\text{\textrangle}-COO-\text{\textlangle}\bigcirc\text{\textrangle}-NCS$ |
| Comp B | $C_8H_{17}-O-\text{\textlangle}\bigcirc\text{\textrangle}-O-CO-\text{\textlangle}\bigcirc\text{\textrangle}-O-CH_2-\text{\textlangle}\bigcirc\text{\textrangle}-CN$ |
| $DB_7NO_2$ | $C_7H_{15}-\text{\textlangle}\bigcirc\text{\textrangle}-O-CO-\text{\textlangle}\bigcirc\text{\textrangle}-O-CO-\text{\textlangle}\bigcirc\text{\textrangle}-NO_2$ |
| DOBAMBC | $C_{10}H_{21}-O-\text{\textlangle}\bigcirc\text{\textrangle}-CH=N-\text{\textlangle}\bigcirc\text{\textrangle}-CH=CH-COO-CH_2-CH(CH_3)(C_2H_5)$ |
| nOm<br>n = 1, m = 4: MBBA<br>n = 2, m = 4: EBBA | $C_nH_{2n+1}-O-\text{\textlangle}\bigcirc\text{\textrangle}-CH=N-\text{\textlangle}\bigcirc\text{\textrangle}-C_mH_{2m+1}$ |
| nOBA<br>n = 8: OOBA<br>n = 9: NOBA | $C_nH_{2n+1}-O-\text{\textlangle}\bigcirc\text{\textrangle}-COOH$ |
| nmOBC | $C_nH_{2n+1}-O-CO-\text{\textlangle}\bigcirc\text{\textrangle}-\text{\textlangle}\bigcirc\text{\textrangle}-O-C_mH_{2m+1}$ |
| nOCB | $C_nH_{2n+1}-O-\text{\textlangle}\bigcirc\text{\textrangle}-\text{\textlangle}\bigcirc\text{\textrangle}-CN$ |
| nOSI | $C_nH_{2n+1}-O-\text{\textlangle}\bigcirc\text{\textrangle}-\text{\textlangle}\bigcirc\text{\textrangle}-COO-\text{\textlangle}\bigcirc\text{\textrangle}-CH_2-CH(CH_3)(C_2H_5)$ |

TABLE 1-continued

Molecular structure of mesogens suitable for use in Liquid Crystal Assay Devices

| Mesogen | Structure |
|---|---|
| 98P | $C_3H_7$—[$CH_2(CH_3)$]$_5$—O—⟨phenyl⟩—⟨pyrimidine⟩—$C_8H_{17}$ |
| PAA | $CH_3$—O—⟨phenyl⟩—N=N(O)—⟨phenyl⟩—O—$CH_3$ |
| PYP906 | $C_9H_{19}$—⟨pyrimidine⟩—⟨phenyl⟩—O—$C_6H_{13}$ |
| $\overline{n}$Sm | $C_nH_{2n+1}$—O—⟨phenyl⟩—CO—S—⟨phenyl⟩—$C_mH_{2m+1}$ |

Presently preferred mesogens are displayed in Table 1. In a particularly preferred embodiment, the mesogen is a member selected from the group consisting of 4-cyano-4'-pentylbiphenyl, N-(4-methoxybenzylidene)-4-butlyaniline and combinations thereof.

The mesogenic layer can be a substantially pure compound, or it can contain other compounds which enhance or alter characteristics of the mesogen. Thus, in one preferred embodiment, the mesogenic layer further comprises a second compound, for example and alkane, which expands the temperature range over which the nematic and isotropic phases exist. Use of devices having mesogenic layers of this composition allows for detection of the analyte recognition moiety interaction over a greater temperature range.

In some preferred embodiments, the mesogenic layer further comprises a dichroic dye or fluorescent compound. Examples of dichroic dyes and fluorescent compounds useful in the present invention include, but are not limited to, azobenzene, BTBP, polyazo compounds, anthraquinone, perylene dyes, and the like. In particularly preferred embodiments, a dichroic dye of fluorescent compound is selected that complements the orientation dependence of the liquid crystal so that polarized light is not required to read the assay. In some preferred embodiments, if the absorbance of the liquid crystal is in the visible range, then changes in orientation can be observed using ambient light without crossed polars. In other preferred embodiments, the dichroic dye or fluorescent compound is used in combination with a fluorimeter and the changes in fluorescence are used to detect changes in orientation of the liquid crystal.

V. Direct Detection of Entities with Lipid Membranes

The present invention provides methods and devices for the direct detection of entities having a biological membrane, including viruses and bacteria that are pathogens. The systems and devices of the present invention can be of any configuration that allows for the contact of a mesogenic layer with an organic layer or inorganic layer (e.g., metal, metal salt or metal oxide). The only limitations on size and shape are those that arise from the situation in which the device is used or the purpose for which it is intended. The device can be planar or non-planar. Thus, it is within the scope of the present invention to use any number of polarizers, lenses, filters lights, and the like to practice the present invention.

The systems and devices of the present invention find use in the detection of variety of viruses and entities having lipid membranes. Examples of such entities having lipid membranes include, but are not limited to, viruses, bacteria, liposomes, cells, mycoplasmas, protozoans, fungi and the like.

The present invention is not limited to the detection of any particular type of virus. Indeed, the present invention contemplates the detection of a variety of viruses, including viruses from the following families: Adenoviridae, Arenaviridae, Astroviridae, Birnaviridae, Bunyaviridae, Caliciviridae, Circoviridae, Coronaviridae, Filoviridae, Flaviviridae, Hepadnaviridae, Herpesviridae, Iridoviridae, Filoviridae, Orthomyxoviridae, Papovaviridae, Paramyxoviridae, Parvoviridae, Picornaviridae, Poxyiridae, Reoviridae, Retroviridae, Rhabdoviridae, Togaviridae, Badnavirus, Bromoviridae, Comoviridae, Geminiviridae, Partitiviridae, Potyviridae, Sequiviridae, and Tombusviridae; the following genera: Mastadenovirus, Aviadenovirus, African swine fever-like viruses, Arenavirus, Arterivirus, Astrovirus, Aquabimavirus, Avibirnavirus, Bunyavirus, Hantavirus, Nairovirus, Phlebovirus, Calicivirus, Circovirus, Coronavirus, Torovirus, Deltavirus, Filovirus, Flavivirus, Japanese Encephalitis Virus group, Pestivirus, Hepatitis C -like viruses, Orthohepadnavirus, Avihepadnavirus, Simplexvirus, Varicellovirus, Cytomegalovirus, Muromegalovirus, Roseolovirus, Lymphocryptovirus, Rhadinovirus, Ranavirus, Lymphocystivirus, Goldfish virus-like viruses, Influenzavirus A, B, Influenzavirus C, Thogoto-Like viruses, Polyomavirus, Papillomavirus, Paramyxovirus, Morbillivirus, Rubulavirus, Pneumovirus, Parvovirus, Erythrovirus, Dependovirus, Enterovirus, Rhinovirus, Hepatovirus, Cardiovirus, Aphthovirus, Orthopoxvirus, Parapoxvirus, Avipoxvirus, Capripoxvirus, Leporipoxvirus, Suipoxvirus, Molluscipoxvirus, Yatapoxvirus, Orthoreovirus, Orbivirus, Rotavirus, Coltivirus, Aquareovirus, mammalian type B retroviruses, mammalian type C retroviruses, avian type C retroviruses, type D retroviruses, blv-htlv retroviruses, Lentivirus, Spumavirus, Vesiculovirus, Lyssavirus, Ephemerovirus, Alphavirus, Rubivirus, Badnavirus, Alfamovirus, Ilarvirus, Bromovirus, Cucumovirus, Tospovirus, Capillovirus, Carlavirus, Caulimovirus, Closterovirus, Comovirus, Fabavirus, Nepovirus, Dianthovirus, Enamovirus, Furovirus, Subgroup I Geminivirus, Subgroup II Geminivirus, Subgroup III Geminivirus, Hordeivirus, Idaeovirus, Luteovirus, Machlomovirus, Marafivirus, Necrovirus, Partitiviridae, Alphacryptovirus, Betacryptovirus, Potexvirus, Potyvirus, Rymovirus, Bymovirus, Fijivirus, Phytoreovirus, Oryzavirus, Nucleorhabdovirus, Sequivirus, Waikavirus, Sobemovirus, Tenuivirus, Tobamovirus, Tobravirus, Carmovirus, Tombusvirus, Trichovirus, Tymovirus, Umbravirus; and the following species: human adenovirus 2, fowl adenovirus 1, African swine fever virus, lymphocytic choriomeningitis virus, equine arteritis virus, human astrovirus 1, infectious pancreatic necrosis virus, infectious bursal disease virus, Bunyamwera virus, Hantaan virus, Nairobi sheep disease virus, sandfly fever Sicilian virus, vesicular exanthema of swine virus, chicken anemia virus, avian infectious bronchitis virus, Berne virus, hepatitis delta virus, Marburg virus, yellow fever virus, west Nile virus, bovine diarrhea virus, hepatitis C virus, hepatitis B virus, duck hepatitis B virus, human herpesvirus 1, human herpesvirus 3, human herpesvirus 5, human cytomegalovirus, mouse cytomegalovirus 1, human herpesvirus 6, human herpesvirus 4, ateline herpesvirus 2, frog virus 3, flounder virus, goldfish virus 1, influenza A virus, influenza B virus, influenza C virus, Thogoto virus, murine polyomavirus, cottontail rabbit papillomavirus (Shope), Paramyxovirus, human parainfluenza virus 1, measles virus, mumps virus, human respiratory syncytial virus, mice minute virus, B19 virus, adeno-associated virus 2, poliovirus 1, human rhinovirus 1A, porcine rhinovirus, hepatitis A virus, encephalomyocarditis virus, St. Louis encephalomyocarditis virus, foot-and-mouth disease virus O, vaccinia virus, orf virus, fowlpox virus, sheeppox virus, monkey pox virus, myxoma virus, swinepox virus, Molluscum contagiosum virus, Yaba monkey tumor virus, reovirus 3, bluetongue virus 1, simian rotavirus SA11, Colorado tick fever virus, golden shiner virus, mouse mammary tumor virus, murine leukemia virus, avian leukosis virus, Mason-Pfizer monkey virus, bovine leukemia virus, human immunodeficiency virus 1, human spumavirus, vesicular stomatitis Indiana virus, rabies virus, bovine ephemeral fever virus, Sindbis virus, rubella virus, commelina yellow mottle virus, alfalfa mosaic virus, tobacco streak virus, brome mosaic virus, cucumber mosaic virus, tomato spotted wilt virus, apple stem grooving virus, carnation latent virus, cauliflower mosaic virus, beet yellows virus, cowpea mosaic virus, broad bean wilt virus 1, tobacco ringspot virus, carnation ringspot virus, pea enation mosaic virus, soil-borne wheat mosaic virus, maize streak virus, beet curly top virus, bean golden mosaic virus, barley stripe mosaic virus, raspberry bushy dwarf virus, barley yellow dwarf virus, maize chlorotic mottle virus, maize rayado fino virus, tobacco necrosis virus, white clover cryptic virus 1, white clover cryptic virus 2, potato virus X, potato virus Y, ryegrass mosaic virus, barley yellow mosaic virus, Fiji disease virus, wound tumor virus, rice ragged stunt virus, potato yellow dwarf virus, tobacco necrosis satellite, parsnip yellow fleck virus, rice tungro spherical virus, Southern bean mosaic virus, rice stripe virus, tobacco mosaic virus, tobacco rattle virus, carnation mottle virus, tomato bushy stunt virus, apple chlorotic leaf spot virus, turnip yellow mosaic virus, carrot mottle virus.

The present invention is not limited to the detection of any particular type of bacteria. Indeed, the detection of variety of bacteria is contemplated, including, but not limited to Gram-positive cocci such as *Staphylococcus aureus, Streptococcus pyogenes* (group A), *Streptococcus* spp. (viridans group), *Streptococcus agalactiae* (group B), *S. bovis, Streptococcus* (anaerobic species), *Streptococcus pneumoniae*, and *Enterococcus* spp.; Gram-negative cocci such as *Neisseria gonorrhoeae, Neisseria meningitidis*, and *Branhamella catarrhalis*; Gram-positive bacilli such as *Bacillus anthracis, Bacillus subtilis, Corynebacterium diphtheriae* and *Corynebacterium* species which are diptheroids (aerobic and anerobic), *Listeria monocytogenes, Clostridium tetani, Clostridium difficile, Escherichia coli, Enterobacter* species, *Proteus mirabilis* and other spp., *Pseudomonas aeruginosa, Klebsiella pneumoniae, Campylobacter jejuni, Legionella peomophilia, Mycobacterium tuberculosis, Clostridium tetani, Hemophilus influenzae, Neisseria gonorrhoeae, Treponema pallidum, Bacillus anthracis, Vibrio cholerae, Borrelia burgdorferi, Cornebacterium diphtheria, Staphylococcus aureus, Bacillus anthracis*, and other members of the following genera: *Vibrio, Salmonella, Shigella, Pseudomonas, Actinomyces, Aeromonas, Bacillus, Bacteroides, Bordetella, Brucella, Campylobacter, Capnbocylophaga, Clamydia, Clostridium, Corynebacterium, Eikenella, Erysipelothriz, Escherichia, Fusobacterium, Hemophilus, Klebsiella, Legionella, Leptospira, Listeria, Mycobacterium, Mycoplasma, Neisseria, Nocardia, Pasteurella, Proteus, Pseudomonas, Rickettsia, Salmonella, Selenomonas, Shigelia, Staphylococcus, Streptococcus, Treponema, Bibro*, and *Yersinia*. Bacterial infections result in diseases such as bacteremia, pneumonia, meningitis, osteomyelitis, endocarditis, sinusitis, arthritis, urinary tract infections, tetanus, gangrene, colitis, acute gastroenteritis, bronchitis, and a variety of abscesses, nosocomial infections, and opportunistic infections.

The present invention is not limited to the detection of any particular fungi. Examples of fungi include, but are not limited to, dermatophytes (e.g., *Microsporum canis* and other M. spp.; and *Trichophyton* spp. such as *T. rubrum*, and *T. mentagrophytes*), yeasts (e.g., *Candida albicans, C. Tropicalis*, or other *Candida* species), *Saccharomyces cerevisiae, Torulopsis glabrata, Epidermophyton floccosum, Malassezia furfur* (*Pityropsporon orbiculare*, or *P. ovale*), *Cryptococcus neoformans, Aspergillus fumigatus, Aspergillus nidulans*, and other *Aspergillus* spp., Zygomycetes (e.g., *Rhizopus, Mucor*), *Paracoccidioides brasiliensis, Blastomyces dermatitides, Histoplasma capsulatum, Coccidioides immitis*, and *Sporothrix schenckii*. Fungal infections (mycoses) may be cutaneous, subcutaneous, or systemic. Superficial mycoses include tinea capitis, tinea corporis, tinea pedis, onychomoycosis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis (phycomycosis), paracoccidioidomycosis, North American blastomycosis, histoplasmosis, coccidioidomycosis, and sporotrichosis. Fungal infections also contribute to meningitis and pulmonary or respiratory tract diseases. Opportunistic fungal infections have proliferated, particularly in immunocompromised patients such as those with AIDS. Preferred organisms include *Escherichia coli, Streptococcus pneumoniae, Staphylococcus aureus, Saccharomyces cerevisiae, Aspergillus fumigatus*, and *Aspergillus nidulans*. See Goodman and Gilman's Pharmacological Basis of Therapeutics, (8th ed., 1990) Table 44-1, page 1024-1033, for additional microbial pathogens, diseases, and current therapeutic agents. The above-described cells are generally available, for example, from the American Type Culture Collection.

The present invention is not limited to the detection of any particular types of cells. Examples of such cells include, but are not limited to, Chinese hamster ovary cells (CHO-K1, ATCC CC1-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci., 383:44-68 [1982]); MRC 5 cells; FS4 cells; rat fibroblasts (208F cells); MDBK cells (bovine kidney cells); human hepatoma line (Hep G2), and, for example, the following cancerous cells or cells isolated from the following carcinomas: fibrosarcoma, myxosarcoma, liposarcoma, chondrosarcoma, osteogenic sarcoma, chordoma, angiosarcoma, endotheliosarcoma, lymphangiosarcoma, Ewing's tumor, lymphangioendotheliosarcoma, synovioma, mesothelioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrbm's macroglobulinemia, and heavy chain disease.

Accordingly, in some embodiments, the present invention provides substrates comprising at least one detection region comprising a recognition moiety that binds to or otherwise interacts with a virus or a biological entity having a lipid membrane. In preferred embodiments, the detection regions are discreet and created by arraying at least one recognition moiety on the surface of the substrate. As described above, the inventors have made the surprising discovery that viral particles bound to a virus recognition moiety on a substrate surface provide for the homeotropic orientation of mesogens in a liquid crystal independent of the presence of any other homeotropic director (e.g., surface topography that causes homeotropic orientation) in the detection region. Also, the inventors have surprisingly found that entities with lipid membranes (e.g., cells) also provide for the homeotropic orientation of mesogens independent of the presence of other homeotropic directors. Accordingly, in some preferred embodiments, the detection region does not include structures which homeotropically orient mesogens in a liquid crystal in the absence of virus or entity with a lipid membrane bound to or otherwise interacting with the detection region. In preferred embodiments, the recognition moiety is immobilized on the substrate as described in detail above. In some embodiments, a plurality of recognition moieties are arrayed on the surface of the substrate so that multiplexed assays for a variety of viruses and/or entities having a lipid membrane can be performed simultaneously. In other embodiments, the control regions are included on the substrate that comprise control species immobilized on the surface of the substrate or which provide a site to contact with a control sample containing a known amount of the entity that is being detected.

The present invention is not limited to any particular method of detection a change in the orientation of the mesogens in the device. Thus, it is within the scope of the present invention to use lights, microscopes, spectrometry, electrical techniques and the like to aid in the detection of a change in the mesogenic layer. In those embodiments utilizing light in the visible region of the spectrum, the light can be used to simply illuminate details of the mesogenic layer to provide for visual detection. Alternatively, the light can be passed through the mesogenic layer and the amount of light transmitted, absorbed or reflected can be measured. The device can utilize a backlighting device such as that described in U.S. Pat. No. 5,739,879. Light in the ultraviolet and infrared regions is also of use in the present invention. Microscopic techniques can utilize simple light microscopy, confocal microscopy, polarized light microscopy, atomic force microscopy (Hu et al., Langmuir 13:5114-5119 (1997)), scanning tunneling microscopy (Evoy et al., J. Vac. Sci. Technol A 15:1438-1441, Part 2 (1997)), and the like. Spectroscopic techniques of use in practicing the present invention include, for example, infrared spectroscopy (Zhao et al., Langmuir 13:2359-2362 (1997)), raman spectroscopy (Zhu et al., Chem. Phys. Lett. 265:334-340 (1997)), X-ray photoelectron spectroscopy (Jiang et al., Bioelectroch. Bioener. 42:15-23 (1997)) and the like. Visible and ultraviolet spectroscopies are also of use in the present invention. Other useful techniques include, for example, surface plasmon resonance (Evans et al., J. Phys. Chem. B 101:2143-2148 (1997), ellipsometry (Harke et al., Thin Solid Films 285:412-416 (1996)), electrical methods (such as impedometric methods (Rickert et al., Biosens. Bioelectron. 11:757:768 (1996)), and the like.

Figure 7:
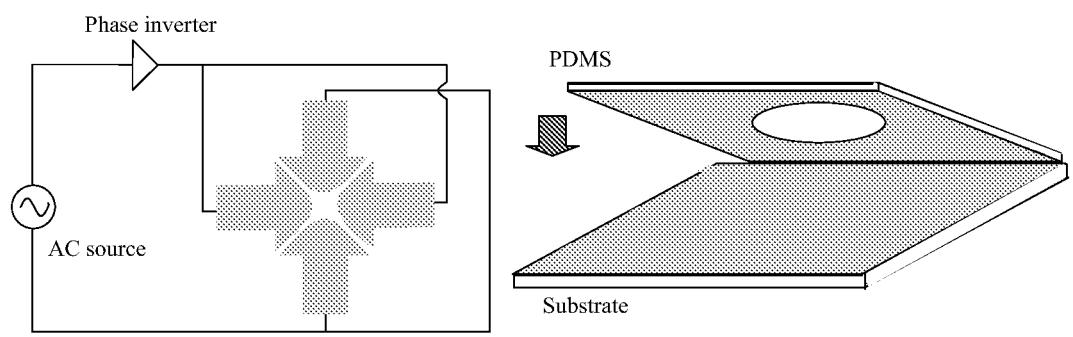
FIG. 7 shows a schematic of an device configured for dielectrophoresis.

In some embodiments, the devices of the present invention further comprise an electrode or series of electrodes. In some preferred embodiments, at least two electrodes are provided in a plane on one of the surfaces of the device substrate. A variety of electrodes may be utilized, including, but not limited to, interdigitated, hyperbolic, triangular and rectangular electrodes. In some particularly preferred embodiments, the device comprises interdigitated electrodes. FIGS. 3a and 3b provide a schematic depiction of a device and preferred electrodes of the present invention. FIG. 3a depicts liquid crystal molecules supported on a nanostructured surface coated with a recognition moiety (in this embodiment an antibody). In the absence of bound analyte, the mesogens assume a planar orientation. Upon binding of an analyte (in this embodiment, virus particles) on to the surface the molecules align perpendicular to the surface inducing a change in the capacitance between two electrodes. FIG. 3b present a schematic of interdigitated electrodes. In this embodiment, the size of the arrows is on the order of 500 µm. FIG. 7 presents a schematic depiction of a substrate configured for dielectrophoresis. The electrode is formed on the surface of the substrate by methods known in the art (e.g., photolithography, printing, etc.). The electrode includes a circuit that interfaces with power source (e.g., an alternating current source) and a phase inverter. In some embodiments, a mask (e.g., formed from PDMS) is used to contain the sample on the substrate during dielectrophoresis.

In preferred embodiments, the electrodes are utilized to transfer viral or other particles to a surface of the assay device, preferably to a surface comprising recognition moieties. The electrodes are also utilized to measure changes in dielectric capacitance of the device (described in more detail below and in the examples).

A challenge that confronts the realization of rapid surface-based detection systems is the efficient capture of viruses present in the liquid sample by the assay surface. Most approaches rely on diffusion of virus to the surface and on enhancement of this process by either mechanical approaches to increase fluid motion or by increases in temperature. These are satisfactory approaches when sufficient numbers of virus particles are present in a reasonably large volume of sample, and the contact of sample with the surface occurs over reasonably long periods of time (hours) such as in virus neutralization, plaque reduction neutralization assays or ELISAs.

In some preferred embodiments, the methods of the present invention utilize dielectrophoresis (DEP) to capture and concentrate virus particles from biological samples directly onto functionalized assay surfaces. DEP is the transport of polarizable particles by a non-uniform time-dependent electric field. The present invention is not limited to any mechanism of action. Indeed, an understanding of the mechanism of action is not necessary to practice the present invention. The DEP force is generated by the interaction of an induced dipole and a non-uniform field; the strength and magnitude of that field being related to the dielectric properties of the analyte (e.g., viruses) and the ionic strength of the medium in which the analyte suspended.

Early work on the effects of DEP on biological particles showed that the dielectrophoretic behavior of two viruses, herpes simplex (HSV) and tobacco mosaic virus (TMV) depended on the frequency of the electric field and the dielectric properties of the virus. At a frequency of 6 MHz in a solution with electrolyte conductivity of 10 mSm$^{-1}$, TMV experienced positive DEP (movement to regions of the highest electric fields). In contrast, under the same conditions, HSV experienced negative DEP (movement to regions of the lowest electric field). In 1999, Morgan et al., Separation of submicron bioparticles by dielectrophoresis. Biophysical Journal 77: 516-525 (1999), demonstrated that dielectrophoresis could be used to separate heterogeneous mixtures of viruses. Using microfabricated polynomial electrodes, they successfully separated a mixture of TMV and HSV. Studies have also shown that the dielectric properties of a virus are affected by changes in the physical or biochemical makeup of the virus particle, such as mechanical damage to the envelope or enzymatic stripping of surface proteins (Hughes et al., Measuring the dielectric properties of herpes simplex virus type 1 virions with dielectrophoresis. Biochimica et Biophysica Acta 1571: 1-8 (2002). Using vaccinia virus labeled with lipophilic carbocyanin dyes and nucleophilic Hoechst dyes, Akin et al. Real-time virus trapping and fluorescent imaging in microfluidic devices, Nano Letters 4: 257-259 (2003) have demonstrated real-time imaging of the capture and trapping of virus particles by dielectrophoretic filters within a microfluidic biochip. In a step towards the development of a rapid diagnostic for food-borne pathogens, Suchiro et al. Selective detection of specific bacteria using dielectrophoretic impedance measurement method combined with an antigen-antibody reaction, Journal of Electrostatics 58: 229-246 (2003) combined measurement of DEP impedance with antibody agglutination to detect bacteria in suspension.

Forces arising from DEP can be used to rapidly concentrate, manipulate, and even separate viruses from small sample volumes. The experiments described above, however, were conducted using model systems of very high concentration, purified virus (up to 10$^{12}$ pfu/mL) suspended in media of very low ionic strength. For practical application to viral diagnostics, DEP must be utilized under conditions of physiological ionic strength (600 mSm$^{-1}$ or greater) and must effectively.

The methods of the present invention contemplate dielectrophoretic forces on viruses to be of the order of 1 pN. This force, when acting on a virus, generates velocities of ~100 μms$^{-1}$. Thus, in preferred embodiments, the time taken for the particle to travel a 100 μm distance is on the order of 1 s. In contrast, Brownian forces acting on virus particles give rise of diffusion coefficients of ~10$^{-12}$ m$^2$s$^{-1}$. Thus the time taken by the virus particle to diffuse through the same distance of 100 μm in absence of dielectrophoretic force is 1.4 hrs. It is thus contemplated that in preferred embodiments, dielectrophoretic forces can accelerate the transport of viruses to surfaces by 3 orders of magnitude.

In further preferred embodiments, the present of analyte in a sample is determined by measuring the dielectric capacitance of the device. The present invention is not limited to a particular mechanism of action. Indeed, an understanding of the mechanism of action is not necessary to practice the present invention. Nevertheless, it is contemplated that liquid crystals have large, anisotropic electrical properties that are reflected in changes in electrical capacitance related to orientation within an electrical field. The method of the present invention, based on dielectric transduction, relies on the principle of change in capacitance between two electrodes when dielectric properties of the medium between them changes. Thus, in some embodiments of the present invention, DEP is utilized to force an analyte (e.g., virus) to the analytic surface. When the analyte binds to the surface, it induces a change in the dielectric property of the medium between the electrodes. When this occurs, it is contemplated that only a very small fraction of the electric field distribution between electrodes will be affected and the change in capacitance between the electrodes will be negligibly small. However, in preferred embodiments, where a film of liquid crystal is placed over the bound virus, the orientational transition of the liquid crystals in response to the virus is propagated throughout the entire layer of liquid crystals affecting almost the entire electric field distribution and the change in capacitance is large and measurable with commercially available devices. It is contemplated the methods of the present invention can be utilized to detect fewer than about 10,000 analyte particles (e.g., viruses) in a sample, preferably fewer than about 1,000 analyte particles in a sample, more preferably fewer than about 100 analyte particles in a sample, and most preferably fewer than about 10 analyte particles in a sample.

Figure 14:
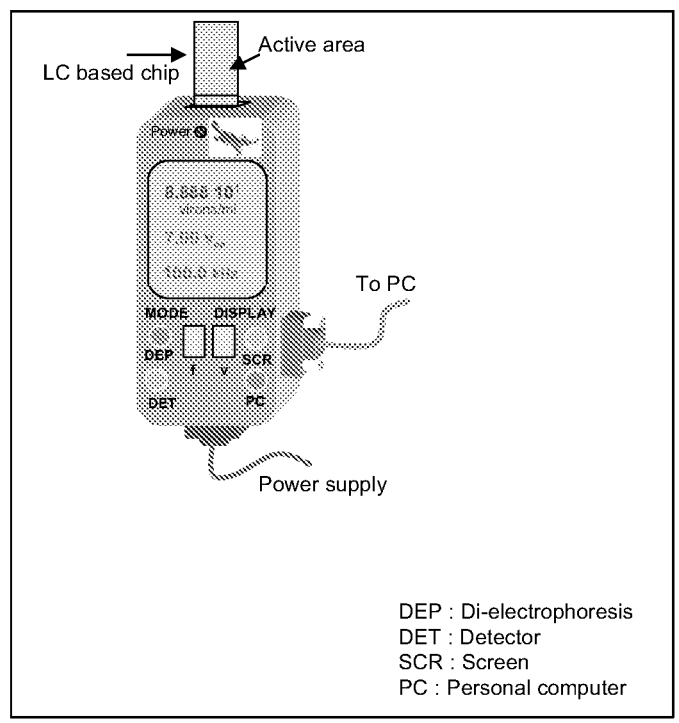
FIG. 14 is a schematic depiction of a readout device of the present invention.

In still further embodiments, the present invention provides devices for detecting the change in dielectric capacitance. FIG. 14 provides a schematic depiction of such a device. The detection device preferably comprises a housing configured to receive an assay device. In preferred embodiments, the housing has an opening therein into which the assay device is inserted. In further embodiments, insertion of the assay device into the detection device causes the electrodes on the device to contact an oscillator circuit. In some preferred embodiments, a microprocessor (such as DS1086 ECONOSCILLATOR, MAXIM Integrated Products Inc.) based oscillator circuit is utilized to generate an AC voltage with the desired amplitude and frequency output. In preferred embodiments, the frequency of the applied electric fields ranges from between about 100 Hz to about 50 MHz. In further preferred embodiments, in order to maintain a small form factor, the input DC voltage is supplied from a battery source. The oscillator circuits provide variable output voltage and frequency by adjusting the parameters, such as capacitance/resistance of the oscillator circuit. In still further embodiments, the devices comprise a liquid crystal display to provide an easy read-out for the output parameters of the oscillator circuit. In some embodiments, a battery charger is integrated into the device to recharge the battery. In still other preferred embodiments, the detection devices comprise a microprocessor that measures the differential capacitance between the electrodes. In some preferred embodiments, the microprocessor is a MS3110 chip. This chip yields the difference between the capacitance in the form of output voltage.

The devices of the present invention can be used to detect the presence of wide variety of biological entities in a sample, including, but not limited to those described above. Likewise, the devices of the present invention can be used to detect biological entities in a variety of samples. In some embodiments, the biological sample is a biological fluid, tissue homogenate, feces, vesicular fluid, swab of an orifice or tissue, or media in which virus has been cultured or prepared. In some embodiments, the biological fluid is cerebral-spinal fluid, urine, serum, plasma, nasal secretion, sputum, semen or saliva.

Biological samples may be collected by a variety of techniques. In some embodiments, whole blood is collected by one of many routes (e.g., venipuncture or fingerstick) into a tube containing an anticoagulant such as heparin or sodium citrate. The blood is mixed and then a sample is removed and placed into contact with a sensing surface. In some embodiments, serum is obtained by permitting blood collected as described to form a clot in the tube. The tube is subjected to centrifugation or is permitted to sit for one or more hours so that the serum component separates from the cellular component. A sample of the serum is placed in contact with the sensing surface. In some embodiments, tissue homogenates are utilized. Pieces of organs (e.g., kidney, spleen, heart, brain, liver, lymph nodes) are either minced by scissors or blades or are placed into a container with fluid (PBS, other buffers, media, water, etc) and homogenized using a plastic pestle or by insertion of a mechanical homogenizer into the container until there are no large pieces of tissue visible. The preparation is centrifuged at low speed (<20,000 rpm for 5-60 minutes) to remove the particulate material remaining. The supernatant is placed in contact with the device substrate surface. In some embodiments, spinal fluid is collected from the spinal cord by a needle. The fluid is inserted into a sterile tube. A sample of the spinal fluid is placed into contact with the device substrate surface. In some embodiments, a sample of nasal secretions is collected onto a cotton or synthetic applicator swab and the swab is placed into a fluid (PBS, water, media, other buffers etc). An aliquot of the sample is placed in contact with the device substrate surface. In some embodiments, a nasopharyngeal aspirate sample is collected by insertion of the swab into the nasopharynx. The swab is placed into a tube containing fluid (PBS, media, water, buffers) and a sample of the fluid is placed in contact with the device substrate surface. In some embodiments, the biological sample is obtained from an intermediate host animal (e.g., a mosquito in the case of West Nile Virus). One or more than one mosquito is suspended in liquid such as phosphate buffered saline or other buffers or media used to grow cells in culture or water. The mosquitoes are homogenized by use of a disposable plastic pestle or by insertion of a mechanical homogenizer into the container. The mosquitoes are homogenizes until no intact insects are visible. The homogenate is subjected to a low speed centrifugation (e.g., 2,000 rpm for 5 minutes) and the supernatant is collected. The supernatant is placed into contact with a device substrate surface. In any of the foregoing embodiments, the sample may require additional centrifugation if particulate matter is visible.

In some embodiments, a second substrate is provided which is configured opposite the first substrate so that cell is formed. In some embodiments, the second substrate is also arrayed with recognition moieties, while in other embodiments, the second substrate is free of recognition moieties. In some embodiments, the second substrate is blocked to prevent non-specific binding or resists non-specific binding.

In some embodiments, samples suspected of containing a virus or entity having a lipid membrane are allowed to contact a detection region(s) on the first substrate. The sample is allowed to contact the substrate for a period of time (e.g., for about 0.5-24 hours, preferably about 2 to 10 hours, and most preferably about 1.5 to 5 hours). In some embodiments, the substrate is rocked during the incubation period. In some embodiments, flowing incubation, the substrate is washed with a suitable buffer (e.g., PBS). The preceding steps can be performed in the presence or absence of the second substrate. For example, in some embodiments, the sample is applies to the substrate and the incubation and wash steps are performed without assembling a cell. In other embodiments, the cell is assembled and the incubation and wash steps are performed in the cell.

Following the wash step, the cell is constructed if necessary. In some embodiments, mesogens are then added to the cell so that a liquid crystal is formed in the cell. The cell is then incubated for a period of time to allow for a change to occur in the liquid crystal. In some embodiments, the change in the liquid crystal occurs immediately. The present assays operate a variable temperature range. In some embodiments, the incubation is conducted at about 15 to 50 degrees C., preferably from about 22 to 35 degrees C.

Following incubation with the liquid crystal, the cell is assayed for whether a change in the liquid crystal has occurred over one or more of the detection regions. Although many changes in the mesogenic layer can be detected by visual observation under ambient light, any means for detecting the change in the mesogenic layer can be incorporated into, or used in conjunction with, the device. Thus, it is within the scope of the present invention to use lights, microscopes, spectrometry, electrical techniques and the like to aid in the detection of a change in the mesogenic layer. In some embodiments, binding of virus to the virus recognition moiety is detected by a change in the color and texture of the liquid crystal. The present invention is not limited to any particular mechanism of action. Indeed, an understanding of the mechanism of action is not necessary to practice the invention. Nevertheless, it is believed that the change in color and texture is due tilting of the mesogens in the liquid crystal prior to assumption of a homeotropic orientation.

Accordingly, in those embodiments utilizing light in the visible region of the spectrum, the light can be used to simply illuminate details of the mesogenic layer. Alternatively, the light can be passed through the mesogenic layer and the amount of light transmitted, absorbed or reflected can be measured. The device can utilize a backlighting device such as that described in U.S. Pat. No. 5,739,879, incorporated herein by reference. Light in the ultraviolet and infrared regions is also of use in the present invention.

In some embodiments, the cell is placed in between cross polar lenses and light is passed though the lenses and the cell. Areas of homeotropic orientation appear black, while areas of planar orientation appear bright. Thus, the presence of bound virus is indicated by a black field while areas where no virus is bound are indicated by a bright field.

In some embodiments, the present invention utilizes plate readers to detect changes in the orientation of mesogens upon binding of an analyte. In particular, the present invention includes methods and processes for the quantification of light transmission through films of liquid crystals based on quantification of transmitted or reflected light.

The present invention is not limited to any particular mechanism of action. Indeed, an understanding of the mechanism of action is not required to practice the present invention. Nevertheless, it is contemplated that ordered nanostructured substrates impart order to thin films of liquid crystal placed onto their surface. These ordered films of liquid crystal preserve the plane of polarized light passed through them. If the liquid crystal possesses a well-defined distortion—such as a 90 degree twist distortion-then the liquid crystal will change the polarization of the transmitted light in a well-defined and predictable manner. It is further contemplated that ordered films (e.g., areas of homeotropic orientation) of liquid crystal differentially absorb (relative to randomly ordered films of liquid crystal) specific wavelengths of light.

Accordingly, the present invention contemplates the use of plate readers to detect light transmission through an LC assay device when viewed through cross polars, the transmission of light through an LC assay device illuminated with a suitable wavelength of light, or reflection of light (i.e., polarized light or non-polarized light of specific wavelengths) from the surface of an LC assay device. In particularly preferred embodiments, plate readers are provided that are designed to be used in conjunction with LC assays. Other embodiments of the present invention provide modified commercially available readers such as ELISA readers and fluorometric readers adapted to read LC assays.

Non-limiting examples of the plate readers useful in conjunction with the present invention are provided in U.S. patent application Ser. No. 10/227,974, incorporated herein by reference. In some embodiments, two polarizing filters are placed in the optical pathway of the plate reader in a crossed or parallel polar configuration. One filter is placed on the emission side of the light path prior to passing through the sample while a second polarizing filter is placed on the analyzing side of the light path after light has passed through the sample but before it is collected by a sensing devise such as a photodiode or a CCD. An ordered liquid crystal in the LC assay device preserves the plane of polarization and the amount of light reaching the light gathering and sensing device is markedly attenuated when viewed through cross polars or markedly accentuated when viewed through parallel polars. Random organization of the liquid crystal of the LC assay device does not preserve the plane of polarization and the amount of light, passing through crossed polars, reaching the light collecting and sensing device is relatively unaffected. Accordingly, in preferred embodiments, the binding of target molecules by the recognition moieties in an LC assay device introduces disorder into the overlying thin film of LC that increases with the amount of bound target molecule. In other embodiments, specific bandpass filters are placed on the excitation side of the light path before light encounters the sample as well as on the emission side of the light path (after light has passed through or is reflected by the sample but before reaching the light collecting and sensing device (e.g., photodiode or CCD). This configuration is useful for quantifying both reflected and transmitted light The present invention also provides LC assay devices configured for use in the plate reader. In preferred embodiments, the LC assay device is formatted or arrayed according to the dimensions of standard commercially available plates (e.g., 24, 96, 384 and 1536 well plates). In some embodiments, the LC assay device comprises a surface (e.g., a substrate with recognition moieties attached) that is of proper external dimensions to be accurately fit into a given commercial reader.

It will also be recognized that the present invention provides an assay system comprising a plate reading device and an LC assay device, wherein the plate reading device and LC assay device are configured so that light provided from the plate reading device which is passed through or reflected from at least one surface of the LC assay device is detected by a detection unit of the plate reading device. Suitable detecting units include CCDs and photomultiplier tubes.

Commercially available plate readers that may be modified according to the present invention include, but are not limited, to those available from Nalge Nunc International Corporation (Rochester, N.Y.), Greiner America, Inc. (Lake Mary, Fla.), Akers Laboratories Inc., (Thorofare, N.J.), Alpha Diagnostic International, Inc. (San Antonio, Tex.), and Qiagen Inc. (Valencia, Calif.).

VI. Non-Specific Detection Following Specific Capture

In some embodiments, the assays of the present find use for the non-specific detection of an analyte following specific capture. In these embodiments, the analyte is captured by a capture substrate (e.g., a PDMS stamp or bead) displaying a recognition moiety that interacts with the analyte. The analyte is then transferred to a detection substrate to which the analyte non-specifically binds. The presence of the analyte on the second substrate is detected by contacting the second substrate with a liquid crystal. Areas of disorder or order within the liquid crystal are indicative of the presence of analyte. As above, a variety of methods are useful for determining whether there is a changes in the orientation of the mesogens of the device. In some embodiments, the assay devices are configured with electrodes as described above so that the analyte can be transferred to a surface of the assay device by use of an electric current (e.g., by dielectrophoresis). The electrodes are also used to measured changes in electrical properties of the device (e.g., dielectric capacitance) as a result of changes in liquid crystal orientation.

In some preferred embodiments, the assays of the present invention are used for the detection of multiple species or genera of animals to a pathogenic organism. As a non-limiting example, antibodies specific West Nile Virus have been detected in samples collected from horses, mallard ducks, pigeons, rabbits, and mice. It will be recognized that these assays find use for testing samples from avian species such as crow, blue jay, eagles, sparrows and the more than 150 species of birds present in the US that are known to be infected with West Nile Viral, horses, humans, small mammals such as dogs and cats and other companion animals, rodents such as mice and rats, etc., and other wildlife such as raccoons, skunks, felines, canids, etc.

In some embodiments, surfaces of the detection substrate as described above are functionalized for protein binding using the chemistries described above. In some preferred embodiments, the detection substrates are substrates onto which a metal (e.g., gold) has been obliquely deposited and functionalized with 4-Aminothiophenol (ATP). In preferred embodiments, it is preferred that the compound used to functionalize the surface of the detection substrate displays a stronger affinity for the ligand (e.g., an antibody) than the ligand displays for its binding partner (e.g., the envelope protein E of West Nile Virus).

In some embodiments, a stamp substrate surface is prepared that displays at least one recognition moiety. A stamp substrate is any substrate that can be used to transfer an entity that is covalently or non-covalently bound to the surface of the stamp substrate to another surface. Examples of suitable stamp substrates include, but are not limited to, PDMS and other elastomeric materials. In some embodiments, different concentrations of the same recognition moiety are arrayed in different areas of the stamp substrate. In other embodiments, a variety of different recognition moieties (e.g., envelope proteins from different enveloped viruses) are arrayed on the stamp substrate surface. In some embodiments, multiple recognition moieties in multiple concentrations are arrayed on the stamp substrate surface. In other embodiments, a control area is included on the stamp substrate surface. The recognition moiety (or recognition moieties) is then introduced to the stamp substrate surface, preferably in an array.

In some embodiments, the stamp substrate surface is a functionalized surface so that a covalent chemical bond is formed with the recognition moiety. In some preferred embodiments, a PDMS substrate is functionalized with disuccinimidyl suberate (DSS). In general, it is preferred that the compound used to functionalize the surface of the stamp substrate displays a stronger affinity for the recognition moiety (e.g., an envelope protein from a virus) than the recognition moiety displays for its associated analyte (e.g., an antibody to the recognition moiety, in this case an antigen, present in serum). Examples of other suitable functionalizing agents includes those that are listed above.

In some embodiments, the stamp substrate is then exposed to a test sample under conditions such that an analyte (e.g., binding partner of the recognition moiety) suspected of being contained in the test sample is captured by the recognition moiety on the stamp substrate. In preferred embodiments, the test sample comprises a body fluid from a test subject. After a period incubation (e.g., 10 minutes to about 10 hours), the stamp substrate is washed. In some embodiments, the detection substrate is then contacted with the stamp substrate under conditions such that the analyte (e.g., an antibody) is transferred from the stamp substrate surface to the detection substrate. In preferred embodiments, the compound used to functionalize the surface of the detection substrate displays a stronger affinity for the analyte than does the recognition moiety so that the analyte is detached from the recognition moiety and transferred to the detection substrate.

In still further embodiments, the analyte is captured on a bead that displays a recognition moiety. As described above, the beads may be formed from latex, polymers, agarose, or other materials and in some preferred embodiments are magnetic. In some embodiments, the analyte is then transferred to the detection substrate. The transfer may be accomplished in a variety of ways. In some embodiments, the analyte is eluted from the beads either directly onto the detection substrate or eluted and the transferred to the detection substrate by a method such as spotting. In other embodiments, the beads exposed to analyte are contacted with the detection substrate so that the analyte is transferred to the detection substrate. As described above, in some embodiments, the detection substrate surface is functionalized with a moiety with a stronger affinity for the analyte than the recognition moiety on the bead so that the analyte is transferred to the detection substrate. In some embodiments, the signal from the analyte is amplified by binding one or more additional molecules to the analyte prior to elution. For example, if the analyte used is an antibody, a secondary anti-species antibody (e.g., and anti-Fc antibody for a particular species or rabbit-anti-human antibody, mouse-anti-human antibody, mouse-anti-rabbit antibody, etc.). Enzyme-antibody conjugates, analyte specific second antibodies, gold sol particles and other molecules and molecule systems may also be utilized. Where nucleic acids are being detected, the analyte detection assays outlined herein may follow an amplification method such as PCR.

A variety of detection substrates find use in the assays of the present invention, including the functionalized substrates described in detail above. In some preferred embodiments, the detection substrate comprises a rubbed polyimide or a polyimide that homeotropically orients a liquid crystal.

In some embodiments, after transfer of the analyte to the detection substrate, a liquid crystal is applied to the detection substrate so that the presence of the binding partner on the detection substrate can be detected. A variety of liquid crystal-forming substances can be used, including those listed above. In some preferred embodiments, 5CB is used. In some embodiments, the detection substrate is used to form an optical cell with another substrate and the liquid crystal is applied to a chamber formed by the two substrates.

As can be seen, the foregoing methods can be adapted to detect of variety of analyte-recognition moiety combinations, including protein-protein, protein-nucleic acid, nucleic acid-nucleic-acid, and other molecular interactions. The detection is label free. Thus, it is contemplated that this system is especially useful for multiplexed assays. As will be appreciated, the capture substrate can be functionalized with a variety of recognition moieties in an array that corresponds to a series of discreet detection regions on the detection substrate. Positive signals on the detection substrate can thus be correlated with the particular ligand on the stamp substrate. Thus, a first detection area on the detection substrate can be specific for a first analyte (e.g., an antibody specific for a particular pathogen), a second detection area on the detection substrate can be specific for a second analyte (e.g., an antibody specific for a second pathogen or a different antibody specific for the first pathogen to provide confirmatory results), and so on.

The label free detection possible with the present system provides advantages over currently used processes such as ELISA. The present system does not require a secondary antibody to detect ligand or antigen specific antibodies from a test subject. This is important because the present system can be utilized to detect antigen/ligand specific antibodies from different species in a single assay because separate secondary antibodies specific for each species are not required. This aspect greatly increases the flexibility of the assays and time needed to respond outbreaks of a disease in a wide or previously unstudied population of subjects. Furthermore, the present system does not require a labeling systems such as radioactive, fluorescent, or enzymatic system. These systems are often relatively unstable or have short shelf lives and require specialized equipment (scintillation counters, film) that is not readily adaptable to field use.

VII. Detection with Lipid Tags

In some embodiments, the ability of lipids such as liposomes to orient liquid crystals is utilized to detect an analyte. As described above, the present invention comtemplates the use of recognition moieties or ligands that are complexed with lipids. In some embodiments, these lipid complexes (e.g., liposomes) are utilized to detect the presence of an analyte in a sample or on substrate. For example, as described above, lipids and lipid containing entities such liposomes can be derivatized to display a recognition moiety such as a protein or nucleic acid. A sample or substrate onto which a sample has been applied can then be contacted with the lipid-recognition moiety complex so that the recognition moiety binds to otherwise becomes associated with the analyte. The resulting analyte-recognition moiety-lipid complex can then be detected by transferring the complex to a substrate if necessary and then contacting the substrate with a liquid crystal. The present invention is not limited to any particular mechanism of action. Indeed, an understanding of the mechanism of action is not necessary to practice the present invention. Nevertheless, it is contemplated that the lipid portion of the complex provides homeotropic orientation to the portion of the liquid crystal in contact with the lipid. The homeotropic orientation can be detected by the methods described above. It will be recognized that it is not necessary that the substrate itself orient the liquid crystal. Thus, these assays can utilize low-cost simple substrates that do not provide an anisotropic surface or surface that is otherwise derivatized with an organic layer. Of course, the substrates have anisotropic surfaces or derivatized surfaces as described above if desired.

In other embodiments, the lipid-recognition moiety complexes are used as secondary binding agents to detect an analyte-recognition moiety complex. For example, an analyte may first be contacted with a first recognition moiety. In some embodiments, the first recognition moiety is a ligand for a second recognition moiety complexed with a lipid. The analyte-first recognition moiety complex is then contacted with the second recognition moiety-lipid complex so that the second recognition moiety binds to the first recognition moiety, thus labeling the analyte-first recognition moiety complex with the lipid. The presence of the lipid can then be detected as described above. In some preferred embodiments, the first recognition moiety is fused to either avidin or biotin so that a lipid complex comprising either avidin or biotin can be used as the secondary binding agent. In other embodiments, if the first recognition moiety is an antibody, the second recognition moiety can be protein A or an antibody that binds to the first antibody, for example, to the Fc region.

VIII. Kits

In some embodiments, the present invention provides kits for the detection of analytes. In preferred embodiments, the kits comprise one or more substrates as described in detail above. In some embodiments, the kits comprise capture and detection substrates. In some preferred embodiments, the capture substrates are beads or stamps. In further embodiments, the kits comprise a substrate that can be used in conjunction with the detection substrate to assemble a liquid crystal cell. In some embodiments, the kits comprise a vial containing mesogens. In still other embodiments, the kits comprise at least one vial containing a control analyte or analytes. In still other embodiments, the kit comprises instructions for using the reagents contained in the kit for the detection of at least one type of analyte. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); gmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); C (degrees Centigrade); U (units), mU (milliunits); min. (minutes); sec. (seconds); % (percent); kb (kilobase); bp (base pair); PCR (polymerase chain reaction); BSA (bovine serum albumin).

Example 1

Immobilization of Antibodies on Substrates

This example describes different methods for immobilizing antibodies on substrate. Five different immobilization strategies were evaluated:

1) HEXA: adsorption of Protein A, then the West Nile Virus monoclonal antibodies (WNV Mabs) onto a hydrophobic monolayer formed from $CH_3(CH_2)_{15}SH$ (HEXA) on the surface of a gold film. The surface was blocked with BSA after immobilization of the antibody.

2) SPDP: covalent attachment of WNV Mabs to a monolayer formed from 2-mercaptoethylamine (2-MEA) on a gold film by using the sulfhydryl-reactive (protein) and amine-reactive (monolayer) heterobifunctional cross-linker N-succinimidyl 3-(2-pyridyldithio)propionate (SPDP). The surface was blocked with BSA after immobilization of the antibody.

3) PMPI: covalent attachment of Ras polyclonal antibodies (Ras Pabs) to a monolayer formed from 11-mercaptoundecanol (11-MU) on a gold film by using a sulfhydryl-reactive (protein) and hydroxyl-reactive (monolayer) heterobifunctional cross-linker N-(p-maleimidophenyl)isocyanate (PMPI). The surface was blocked with BSA after immobilization of the antibody.

4) DSS: covalent attachment of Ras Pabs to a monolayer formed from 2-MEA on a gold film by using an amino-reactive homobifunctional cross-linker disuccinimidyl suberate (DSS). The surface was blocked with BSA after immobilization of the antibody.

5) Adsp.: direct adsorption of WNV Mabs onto a thin film of polyurethane spin coated on the surface of gold. The surface was blocked with BSA after immobilization of the antibody.

The ellipsometric thicknesses of antibodies immobilized by these five methods was analyzed. All five methods resulted in immobilization of antibodies on surfaces. The three strategies for the covalent immobilization of antibodies to the surfaces (SPDP, PMPI and DSS) led to approximately the same level of immobilization of antibodies (an ellipsometric thickness of 3 nm). Passive adsorption of antibodies (Adsp) on polyurethane surfaces led to capture of an ellipsometric thickness of 8 nm of antibody, and the Protein A mediated attachment of antibodies (HEXA) lead to the immobilization of an ellipsometric thickness of ~4 nm of IgG. The direct adsorption approach (Adsp) and protein A-mediated adsorption lead to the highest levels of antibody immobilization.

Example 2

Detection of West Nile Virus

The detection of viruses with liquid crystal assays in which the detection region comprises topographical features has been described in WO 01/61357. These types of surfaces in combination with liquid crystals were successfully used to report the presence of West Nile Virus (WNV) captured on the surface of such substrates. Surprisingly, however, it has now been found that the reporting mechanism does not require the topography on the surface. This unexpected outcome substantially simplifies the fabrication of substrates for detection of viruses using liquid crystals. As described below, it has been demonstrated that this reporting mechanism can be applied to different viruses.

Antibodies to WNV were deposited onto the surface of molded polyurethane replicas. The micromolded replicas had a pitch of 400 nm and a depth of 54 nm. A drop of aqueous solution containing WNV was deposited onto the surface of the polymeric replica. The solutions contained $10^{8.4}$ pfu/0.2 ml of WNV and the incubation was performed for 4.5 hours. Following incubation of the droplet containing WNV on the surface, the surface was rinsed with PBS and then imaged by using liquid crystal. Surprisingly, regions of the surface that were contacted with the solution containing WNV caused homeotropic anchoring of the liquid crystal. In particular, the homeotropic region was seen both on the areas of the replica that possess topography as well as the nominally smooth areas. Because the fabrication of substrates that do not possess a controlled topography is simple and straightforward to perform, the possibility of using surfaces without topography as the basis of assays for viruses using liquid crystals was investigated. As described below, the homeotropic response to WNV is unique to the presence of specifically captured virus on the surface.

Next, it was necessary to confirm that the observed response in the topography-free region was a response to specifically captured WNV on the surface. Antibodies to SLE, Dengue, LACV and WNV were deposited on the same planar substrate. WNV stock was rocked across the four regions for 17 hours at 35° C. The cell was then observed through crossed polar lenses. The Dengue and LaCV antibody regions displayed brightly colored and disordered LC, indicating no binding of the WNV to non-specific antibodies. The WNV antibody region displayed a complete homeotropic circle, indicating bound virus. In the SLE antibody region, there was a small area of homeotropic alignment, signifying a slight cross-reaction of the WNV to the SLE antibodies.

Several observations were made. First, the homeotropic response of the liquid crystal to WNV is striking and unambiguous. The entire region of the surface that was exposed to the droplet containing WNV assumed a homeotropic orientation. Second, in contrast to the region of the surface presenting antibodies to WNV, the regions presenting antibodies to SLE, Dengue and LACV did not cause a homeotropic orientation of the liquid crystal. It is noted that a small area of the surface presenting the antibodies to SLE did cause homeotropic alignment, however, it is very small as compared to the area presenting antibodies to WNV, and it was clearly distinguishable from the area presenting antibodies to WNV. In summary, these results clearly demonstrate that the homeotropic response of the liquid crystal to WNV is a response to virus that is specifically captured on the regions of the surface presenting antibodies to WNV.

These results were obtained using an optical cell that comprised a second surface of glass treated with OTS. Because the liquid crystal orients homeotropically on the OTS-treated glass surface, the possibility that the homeotropic response of the liquid crystal to bound virus was caused by the OTS-treated glass slide in combination with a lack of orienting influence of a virus-decorated surface was considered. To address this possibility, an optical cell was prepared from two polyurethane surfaces decorated with virus. Homeotropic anchoring of the liquid crystal was observed when virus was captured by the antibodies on the polyurethane surface. From this result it can be concluded that the homeotropic orientation of the liquid crystal on the virus-decorated surfaces is a response to WNV and not caused by the OTS-coated glass slide. Additionally, a planar gold substrate was functionalized with $C_{16}SH$, then WNV monoclonal antibodies and then treated with WNV. The planar gold substrate was then paired with an OTS slide to create an optical cell. It was observed that homeotropic orientation of the liquid crystal can be obtained when the antibodies to the WNV are immobilized on gold films made hydrophobic with hexadecanethiol.

Example 3

Optimization of Antibody Immobilization

Different methods of immobilizing the antibody were investigated to determine the procedure which would give the best results. Briefly, polyurethane substrates were functionalized with (a) 1 uM WNV monoclonal antibodies, (b) 5 uM WNV monoclonal antibodies, and (c) 1 mg/ml Protein A first, then 1 uM WNV monoclonal antibodies. All functionalized substrates were then incubated with the WNV stock. The results showed that substantially the same homeotropic response is observed when the polyurethane is functionalized with 1 uM or 5 uM antibody, and also when the substrate is first incubated with Protein A (molecule which correctly orients the antibody), and then functionalized with 1 uM antibody. These results indicate that a strong homeotropic response can be obtained with a lower concentration of antibody, with or without Protein A. The current method involves coating the entire substrate with 1 mg/ml Protein A, and subsequently immobilizing antibodies in specific detection regions on the substrate.

Example 4

Optimization of Delivery of Virus

The results described above were obtained by incubation of the surfaces with the virus solution for up to 20 hrs. Next, ways of optimize virus delivery to the surface-immobilized WNV monoclonal antibodies and thus minimize the binding times were investigated. The following three parameters were investigated: a) the temperature of the incubation; b) rocking of the sample back-and-forth to generate convection; and (c) the influence of the antibody spot size.

First, increasing the incubation temperature to 35 degrees from room temperature (approximately 22 degrees C.) decreased the required binding time. Next, by delivering an approximately 20 µl drop to the antibody functionalized surface, it was possible to shorten the time needed for a 100% homeotropic alignment response from overnight (16-20 hrs) to 3 hrs. To reduce the binding time even further, a 'rocking' method was introduced into the procedure. Instead of incubating the WNV as a stationary 20 µl drop on the substrate, a PDMS "pool" was used to contain a larger volume (300 µl) of WNV on top of the substrate. The WNV was then rocked continuously using a bi-directional rotator. This change in procedure led to a reduction of binding time from 3 hours to 2 hours. To determine the effect of reducing the spot size of the antibody, the antibody volume (to be immobilized) was decreased from 20 µl to 5 µl. By combining these three methods, increasing temperature, rocking, and reducing the surface area of immobilized antibody, the binding time was decreased from 2 hours to 1.5 hours. It should be emphasized that this is the only incubation time required for the assay. Once the virus and antibody have interacted, the liquid crystals are added and they assume their preferred orientation within seconds. Read out is immediate. The orientation is stable and the assay need not be read immediately. This does not represent a fixed time requirement. These end points were set as 100% homeotropic alignment. Partial alignment has been noted before the 1.5 hr point. These results provide unambiguous evidence that liquid crystals can be used to detect WNV bound to a substrate coated with antibodies to WNV via the homeotropic response of the liquid crystal.

Example 5

Demonstration of Detection of St. Louis Encephalitis Virus (SLE)

To assess the generality of the method of reporting viruses other than WNV via the homeotropic response of the liquid crystal, an experiment was performed to determine if SLE could be detected via the response of liquid crystal to SLE captured on a surface presenting antibodies to SLE. Assays for SLE were performed essentially as described above for WNV. In each case when SLE virus was tested in the assay, areas of homeotropic alignment were observed on the edge of the slide, outside of the diagnostic zone but in the direction of the PBS wash. It appears as though the antigen-antibody complexes that formed on the diagnostic surface were washed away during the PBS rinse and only some residual remained near the edge of the slide to be visualized by the homeotropic alignment of the liquid crystals. This did not happen with the WNV assay. These areas indicate that SLE can be detected via the homeotropic response of the liquid crystal. This result is important, because it suggests that the homeotropic response of liquid crystal is not restricted to WNV but can be exploited for detection of viruses other than WNV. It would be valuable in times such as this when outbreaks of WNV, SLE and EEE are occurring simultaneously to have a rapid multi-plexed assay available.

Example 6

Assays With Multiple Detection Regions

A useful format for assays for viruses is a multi-array with antibodies to several viruses patterned spatially on the same surface. To demonstrate the feasibility of patterning antibodies on surfaces, and detecting the binding of virus to them, an experiment was performed in which antibodies to WNV were patterned on three regions of a surface. Briefly, a polyurethane substrate was functionalized with WNV monoclonal antibodies in a lane format. WNV was rocked over the substrate for 2 hours at 35° C. Three homeotropic lanes were observed, indicating the location of the bound virus.

Example 7

Detection of WNV from Tissue of Birds

This example describes the detection of WNV from the tissue of birds. Polyurethane substrates were prepared by incubation of the surface with 1 mg/ml Protein A. Next, 4 droplets containing 1 uM WNV monoclonal antibodies were immobilized within each of several sample areas. Crow samples comprising kidney/spleen tissue suspensions were obtained from NWHC's Diagnostic Virology lab. These samples were determined to be positive or negative by real time RT-PCR, or by tissue culture isolation, respectively. Tissue suspensions were centrifuged for 10 min at 2,000 rpm, and the supernatant was applied directly to the sample areas. The WNV stock used in these experiments $10^{7.7}$ pfu/0.2 ml. Incubation was overnight at 35° C. The polyurethane substrate which was functionalized with WNV monoclonal antibodies was treated with positive or negative American crow tissue suspensions, culture media, and WNV stock as a positive control. The positive crow and the WNV sample regions displayed homeotropic alignment, indicating the presence of bound West Nile virus. The negative crow and culture media sample regions displayed disordered and brightly colored LC, indicating the lack of bound virus. We note that the positive control and negative controls yielded the correct response of the liquid crystal.

Additional control experiments were performed using whole blood from birds and horses. Chicken blood (with either heparin or citrate as an anti-coagulant) and horse blood was applied directly to the substrate which was functionalized with WNV antibodies. Incubation was overnight at 35° C. The results clearly demonstrated that there is no cross-reaction or non-specific binding with normal avian or equine whole blood samples. Additional results were obtained with negative sera from chicken/horse/mallard/or with culture media. Additionally, six mosquito homogenates from the NY State Dept of Health were that have previously shown to be negative for WNV by Taqman PCR were obtained and tested. These homogenates also tested negative with the LC assay and did not show any evidence of non-specific binding to the surface. This experiment demonstrates the ability to use concentrated biological samples with little processing in the assays of the present invention.

Example 8

Homeotropic Orientation by Cells

This example demonstrates homeotropic orientation by tissue culture cells. Tissue culture cells are allowed to attach to the surface of a glass slide. The surface is washed and mesogens are placed on the surface. Areas of the surface occupied by cells appear uniformly dark. Areas not occupied by cells regions display disordered and brightly colored LC.

Example 9

Detection by Stamp Transfer

This example describes the detection of antibodies transferred from a stamp substrate comprising a ligand to a detection substrate. To form the stamp substrate, 10 parts elastomer to 1 part curing agent from the Sylgard 184 Elastomer Kit (Dow Corning) is mixed together, degassed in a vacuum desiccator, and cured into PDMS at ~65° C. for 1 hour. The PDMS stamps are cut out from the PDMS cured to a Fisher's Finest Glass Microscope Slide. The PDMS stamps are then rinsed with ethanol and dried with nitrogen to clean them. The PDMS stamps are then plasma ashed in an oxygen plasma (200 mTorr $O_2$ backfill pressure) at 275 Watts for 4 minutes to oxidize the surface of the PDMS producing a surface similar to glass. The PDMS stamps are then submerged in a 2% APES/98% dry acetone solution for 2 minutes with constant stirring. PDMS stamps are then transferred into acetone for 5 minutes with constant stirring. The PDMS stamps are removed from the acetone, rinsed with acetone, and dried with nitrogen. The PMDS stamps are then placed in an oven uncovered for 30 minutes at 100° C. The PDMS stamps are removed from the oven and cooled to room temperature before placing them into a 1 mM DSS (Pierce) solution made from dissolving 74 mg of DSS in 2 ml of DMSO which is mixed with 198 ml of dry methanol. Stamps are kept in 20 ml of the DSS chemistry for 1 hour with constant stirring. The PDMS stamps are then removed from the DSS and rinsed with methanol followed by a nitrogen stream to dry them. Twenty μL drops of 0.25 μM protein E ($L^2$ Diagnostics, LLC) are then incubated on the individual stamps overnight at 4° C. and for 1.5 hours at room temperature.

Figure 5:
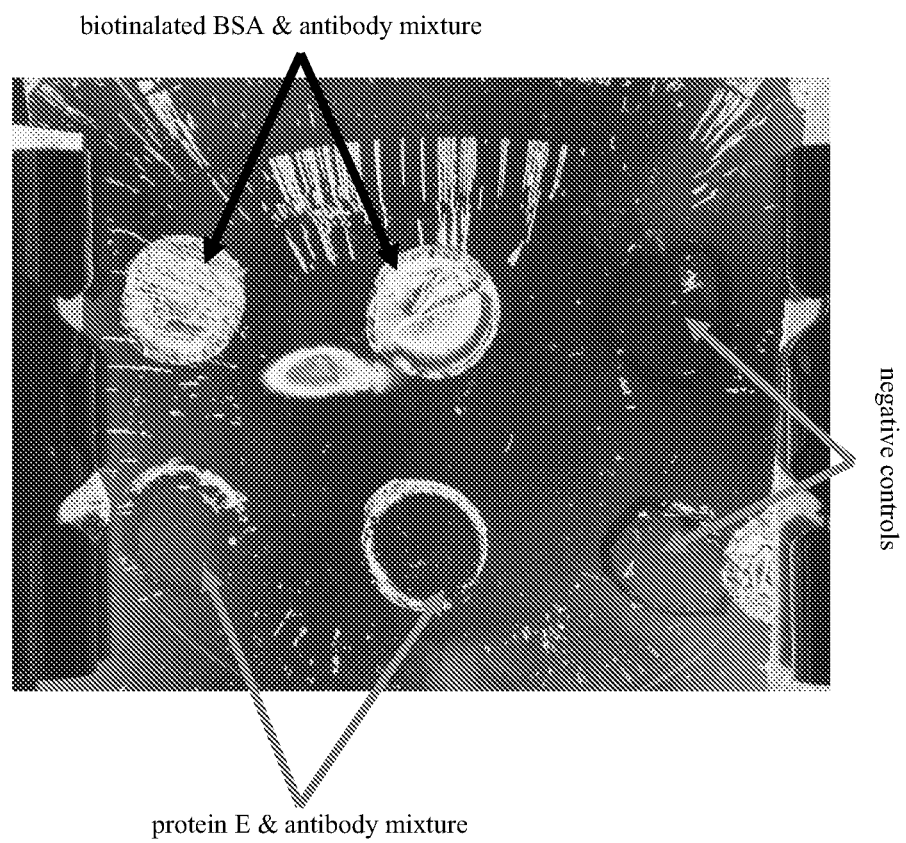
FIG. 5 is an image of an assay conducted with an assay device of the present invention.

An obliquely (35°) deposited 30 Å Ti/300 Å Au Corning 1737 microscope slide is placed in 11 mM ATP (4-aminothiophebol, Aldrich) overnight. The droplets of protein E are then rinsed off of the stamps with milli-Q water from a squirt bottle for approximately 15 seconds followed by a nitrogen stream to dry the stamps. Twenty μL drops of 20 mg/ml (total protein concentration) anti-E rabbit polyclonals ($L^2$ Diagnostics, LLC), 20 mg/ml negative rabbit serum (Pierce), 1:2 dilution positive horse serum (Cornell university), and 1:2 dilution negative horse serum (Cornell University) are placed on their individual stamps where the protein E was incubated (dilutions done in PBS). The sera are incubated at room temperature for 6 hours. The sera are rinsed off the PDMS stamps with 0.5 ml. of 0.01% Triton in PBS followed by a milli-Q water rinse for 15 seconds from a squirt bottle. The stamps are then dried with nitrogen. The oblique gold-coated slide is removed from the ATP, rinsed with ethanol, dried with nitrogen, dipped into the 0.1N HCl, dried with nitrogen, dipped again into the 0.1N HCl, and dried with nitrogen.

The PDMS stamps are then gently placed into contact with the ATP treated oblique gold slide for 1 minute with gentle pressure for 5 seconds at the beginning and end of contact. The stamps are removed from the surface. Optical cells are constructed by separating the stamped oblique gold/ATP surface from a Fisher slide that had been vacuum deposited with OTS ((Tridecafluoro-1,1,2,2-tetrahydrooctyl)trimethoxysilane, Gelest), with 25 μm Mylar. The optical cells are held together with binder clips. 5CB liquid crystal (4-cyano-4'pentyl-1-1'-biphenyl, EM Science) is then introduced into the optical cells in its isotropic phase at ~40° C. Optical cells are then heated at 37° C. until (usually overnight) the liquid crystal is aligned homeotropically everywhere, unless there is disruption in a circular form from transferred biological agents.

The results are presented in FIG. 2. In this procedure, protein E is covalently bound to the DSS chemistry on the PDMS stamp. The protein E in turn captures WNV antibodies if present in the serum incubation droplet. Even if there are no WNV antibodies in the serum (in this case the negative serums or controls on the right of FIG. 2) there is assumed to be some non-specific absorption to the PDMS stamp surface, thus the need for using the Triton rinse to remove non-specific absorbed entities. When the PDMS stamp is brought into contact with the ATP treated gold surface the protein E stays covalently bound to the DSS chemistry on the stamp and the captured WNV antibodies, if present, transfer to the ATP chemistry due to the physics of a stronger bond. Referring to the pictures in FIG. 2, the two optical cells on the left, as viewed through crossed-polarizers, were stamped with PDMS that had sera positive for the WNV antibodies incubated on them. The two pictures on the right of FIG. 2 show the control optical cells, as viewed through crossed-polarizers, that were stamped with PDMS that had sera negative for WNV antibodies incubated on them. When WNV antibodies are present, the stamps that captured WNV antibodies on them transfer to the ATP treated gold causing a circular (from the shape of the incubation droplet) disruption pattern in the liquid crystal optical cell, see pictures on the left. The control stamps that have not captured antibody demonstrate homeotropically aligned liquid crystal in the optical cell (see pictures on the right of FIG. 2).

Example 10

Affinity Contact Printing (αCP) to Report a Specific Antibody from a Population

This experiment demonstrates the capture of a specific antibody from a mixture of two antibodies in solution. A six button PDMS stamp, see FIG. 4, was plasma ashed in an $O_2$ cloud for 8 minutes to oxidize the surface of the PDMS. The stamp was then placed in a 2% APES in dry acetone solution for 2 minutes while stirring. The stamp was then placed in acetone for 5 minutes while stirring. The stamp was then rinsed with acetone, dried with nitrogen, and placed in a 100° C. oven for 30 minutes. The stamp was then placed in a 1 mM DSS solution for 1 hour while stirring. The stamp was removed from the DSS, rinsed with methanol, and dried with nitrogen. On three of the buttons on the six button PDMS α-stamp, 20 μl drops of 0.25 μM protein E were incubated overnight at 4° C. The remaining three buttons had 20 μl drops of 0.25 μM biotinalated BSA incubated on them overnight at 4° C. The proteins were rinsed off with water and the α-stamp was dried with nitrogen. Two of the three protein E functionalized buttons and two of the three biotinalated BSA functionalized buttons had 20 μl drops of a 0.25 μM mixture of anti-biotin and anti-E incubated on them for 6 hours at room temperature. The third protein E functionalized button had a 20 μl droplet of 0.25 μM anti-biotin incubated on it for six hours at room temperature as a negative control. The third biotinalated BSA functionalized button had a 20 μl droplet of 0.25 μM anti-E incubated on it for six hours at room temperature as a negative control. Each of the six individual buttons were first rinsed with ~5 drops of 0.01% Triton in PBS followed by a 15 second rinse with milli-Q water and then dried with nitrogen. The six button α-stamp was then put into contact with a 1 mM ATP treated 35° obliquely deposited Au slide for ~1 minute with a few seconds of gentle pressure at the beginning to insure contact. The α-stamp was then peeled off and the optical cell was put together with an OTS slide and 5CB liquid crystal. The optical cell was then incubated at 40° C. for two days to turn the background LC homeotropic. The results are provided in the image in FIG. 5.

Analysis of this data reveals two strong positives from the biotinalated BSA pulling out its specific antibody, anti-biotin, from a mixture and reporting it in the LC optical cell seen via αCP. Both of the protein E buttons that had the antibody mixture incubated on them show a positive result around the rim of the printing area from the anti-E transferring, but not as strong of a signal as the anti-biotin readouts. Both negative controls were blank, which would imply that the four positive controls pulled out their specific antibodies from the antibody mixture and reported them via αCP. The anti-E signals could not be as strong as the anti-biotin signals for several reasons: too long of an incubation while waiting for the optical cell background to turn homeotropic causing some of the disruption to wash away, and/or uneven pressure of the α-stamp during printing.

Example 11

Polyimide Surfaces can Host Molecular Interactions

A silicon wafer was scrubbed with 1-Methyl-2-Pyrrolidinone (NMP). The scrubbed wafer was spin cleaned with NMP at 1700 rpm and the wafer was spin coated with 1.0% solids SE-7210 polyimide at 1700 rpm. The wafers were pre-cured at 85 C for 10 minutes, followed by a final cure at 180 C for 15 minutes. Polyimide surfaces were rubbed by machine with the following settings:
  wheel speed 343 rpm,
  table speed: 3 cm/sec
  non-load wheel current: 0.065 amps
  loaded wheel current: 0.055 amps
  left height readout: 2.530
  right height readout: 2.530
The following materials were deposited in sequence from droplet onto the wafer. A two hour incubation period was used for each addition:
  Protein A: 1 mg/ml
  Bovine serum albumin: 0.1 mg/ml
  Mouse IgG: 1 microMolar
The surface thickness of the wafer, calculated from ellipsometric readings following each binding step, are listed below:

| | |
|---|---|
| Polyimide coated wafer | 21.0, 21.1 |
| Protein A | 23.4, 22.9, 22.9 |
| BSA | 22.3, 21.8, 22.2 |
| Mouse Antibody | 24.9, 24.2 |

These readings demonstrate the binding of Protein A to the polyimide surface and the subsequent binding of Mouse antibody to the Protein A.

Example 12

Detection of molecular interactions on polyimide surfaces by liquid crystals

Glass slides were scrubbed with 1-Methyl-2-Pyrrolidinone (NMP), spin cleaned with NMP at 1700 rpm and spin coated with 1.0% solids polyimide SE-7210 at 1700 rpm. The slides were pre-cured at 85 C for 10 min and subjected to a final cure at 180 C for 15 minutes. The following materials were added by droplet incubation in the order listed:
  Protein A: 1 mg/ml
  BSA 0.1 mg/ml
  Mouse antibody 1 microMolar
Slides were washed with phosphate buffered saline in between incubations. They were dried with a stream of nitrogen and formed into a cell by the addition of a top slide. Liquid crystal ZLI-1221 was added to the space between the glass slides.

The binding of mouse antibody to the immobilized protein A present on the polyimide surface was reported by a change in orientation of the liquid crystals. Areas with only Protein A or with Protein A plus BSA appeared dark to the naked eye when visualized through cross polars, as did the areas of the polyimide surface which were not functionalized with Protein A. The areas that were functionalized with Protein A and had been exposed to the mouse antibody, appeared white when viewed through a polarizing film. The contrast of areas that bound mouse antibody with non-functionalized or non-antibody exposed areas was strong.

This experiment has been conducted with liquid crystals ZL1-15700-000, 5CB, and MLC-6710-080 with similar results to that described above. These experiments demonstrate that liquid crystals can report binding events hosted on functionalized polyimide surfaces.

Example 13

Demonstration of the Specificity of Binding on Polyimide Surfaces

Polyimide surfaces (SE-7210) in combination with liquid crystals can be used to specifically detect target molecules. In this experiment we demonstrate the detection of mouse IgG and the lack of detection of rat IgG on surfaces treated with Protein A. Protein A is known to bind mouse IgG strongly while it shows a weak to no binding affinity for rat IgG.

Glass slides were scrubbed with NMP, spin cleaned with NMP at 1700 rpm and spin coated with 1.0% solids polyimide SE-7210 at 1700 rpm. The slides were pre-cured at 85 C for 10 min and subjected to a final cure at 180 C for 15 minutes. The polyimide surface was rubbed at either a high pressure (2.43) or a normal pressure (2.53), or a low pressure (2.63) under standard rubbing conditions described above.

The following materials were added by droplet incubation in the order listed:
  Protein A: 1 mg/ml
  BSA 0.1 mg/ml
  Mouse IgG 2a 1 microMolar
  Rat IgG 1 microMolar
Slides were washed with phosphate buffered saline in between incubations. They were dried with a stream of nitrogen and formed into a cell by the addition of a top slide. Liquid crystal ZL1-1221 was added to the space between the glass slides.

All three rubbing pressures yielded similar results. There was very limited disruption (the test areas appeared dark under cross polars) on control samples with Protein A, Protein A+BSA or Protein A+BSA+Rat antibody. There was near total disruption on samples with Protein A+BSA+Mouse antibody. The area appeared white under cross polars. There was no significant binding of the rat antibody to the Protein A. this indicates specificity of binding on a polyimide surface.

Example 14

Polyimide Surfaces can Specifically Detect Target Molecules Using a "Sandwich" Technique and the Sensitivity of the System can be Adjusted by Controlling the Amount of Receptor Present on the Surface Glass slides were coated with polyimide and rubbed using the standard protocol described above. The slides were functionalized with the following reagents, using a 30 minute incubation period for each reagent. A series of dilutions of Protein A in the blocking agent fish gelatin of 1:99, 10:90, 25:75, and 50:50 were made to control the sensitivity of the surface to the target molecule
Protein A 1.0 mg/ml
Fish Gelatin 0.1% dilution of a 30% stock solution.
Anti-biotin 100 micrograms/ml
Biotin (100 micrograms/ml) was added to each functionalized area. The secondary anti-biotin antibody (100 micrograms/ml) was applied. Control regions were included that were processed as follows:
1. Protein A+fish gelatin
2. Protein A+fish gelatin+antibody 1
3. Protein A+fish gelatin+antibody 1+biotin Controls 1 and 2 appeared dark when viewed between cross polars, indicating that liquid crystals were uniformly aligned on the surface. Control 3 showed a minimum of disruption, but appeared mostly dark between cross polars, indicating uniform alignment of the liquid crystals. The degree of disruption did appear to increase as the ratio of Protein A to fish gelatin increased, indicating an increase in sensitivity of the surface. The regions exposed to the complete sandwich, Protein A+fish gelatin+antibody 1+biotin+ antibody 2, appeared white when viewed between cross polars, indicating disruption of liquid crystal alignment and therefore the binding of the target molecule, biotin. All ratios of Protein A to fish gelatin yielded similar results in the complete sandwich indicating that concentrations lower than the 1:99 ration could be used to tune the assay.

Example 15

Reduction of Incubation Time and Use of E7 LCF

Polyimide surfaces were prepared identically to those described in Examples 12 and 13. The reagents applied to the surface were also identical to the above experiments. In this instance, the incubation times for each step were reduced from 2 hrs to 10 minutes. Liquid Crystal E7 was used.

A very slight increase in disruption of the liquid crystal film in the sample field was seen in comparison to the minimal disruption in the liquid crystal film over the control areas. The use of E7 significantly reduced the response of the LC to the binding of the mouse IgG. The nature of the disruption was very different by visual observation than the appearance of the disrupted liquid crystals using 5CB or ZL1-1221.

Example 16

Reduction in Incubation Time to 10 Minutes and Variation in Protein Concentration Polyimide surfaces were prepared as described in Examples 12 and 13. A ten minute incubation time was used for each reagent. LC ZL1-1221 was used. The concentration of the target protein (mouse antibody was varied (0.1 microMolar, 0.01 microMolar and 1.0 microMolar) Rat antibody was used as the negative control.

Strong disruption of the liquid crystal film was observed in areas exposed to the 1.0 microMolar concentration of mouse antibody. Moderate disruption was seen in areas exposed to the 0.1 microMolar concentration of mouse antibody. No disruption in the liquid crystal film was observed in areas exposed to the lowest concentration (0.01 microMolar) of mouse antibody. It is possible that a ten minute incubation time under these rubbing conditions is not sufficient for sensitivity at the 0.01 microMolar range.

Example 17

Variation in Protein Concentration with a 2 hr Incubation Time for Antibody

Polyimide surfaces were prepared as described in Examples 12 and 13. All reagents are the same as used in those examples. Rat antibody is used as a negative control. LC ZL1-1221 was used. A ten minute incubation time was used for the Protein A and BSA exposures, but a 2 hr incubation was used for the antibody exposures.

Areas incubated with 1.0 microMolar or 0.1 microMolar mouse antibody showed significant disruption in the liquid crystal film. The area incubated with 0.01 microMolar mouse antibody did not cause disruption in the liquid crystal film. The rat antibody did not cause disruption. The number of antibodies bound to the surface area for the 0.01 microMolar assay may be below the threshold needed to cause disruption in the liquid crystal film. Sensitivity may be increased by decreasing the functionalized surface area.

Example 18

Use of Fish Gelatin to Minimize Protein A binding sites

Four polyimide coated and rubbed slides were blotted with the materials listed below. The slides were blotted using a 30 minute incubation time for each of the materials. A dilution series was created using 1:99, 10:90, 25:75 and 50:50 ratios of Protein A and the diluted Fish Gelatin. Each slide was blotted with one of the four mixed Protein A/Fish gelatin dilution samples. Subsequent additions of primary antibody (anti-biotin), biotin, and secondary antibody (anti-biotin) were added to the specified areas. The coating of slides and the rubbing procedures were identical to those used in the examples above. Reagents:
Protein A: 1.0 mg/ml
Fish Gelatin: 0.1% dilution of 30% stock
Anti-biotin: 100 micrograms/ml
Biotin antigen: 100 micrograms/ml
ZL1-1221

Slight disruption was seen when the primary antibody binds to Protein A for 50:50 and for 25:75 samples. For 10:90 ratios, the disruption is less than above and for 1:99, it is even less.

By diluting the Protein A with fish gelatin it is possible to limit the amount of primary antibody. This is an approach to limit the sensitivity of the system. This allows the rubbed polyimide to be used for systems in which the goal is to create an assay for the detection of an antigen as well as systems for the detection of antibody. Based on these results, it appears that a concentration even lower that 1:99 could be used and may result in even less disruption with the primary antibody and antigen, while still giving good disruption in response to the binding of the secondary antibody.

Example 19

Detection of VSV-1

General Materials:

Virus: vesicular stomatitis virus-Indiana strain (VSV-I) obtained from the American Type Culture Collection (ATCC), Chantilly, Va., will be propagated on BHK-21 cells. Aliquots of the initial stock will be stored at −80° C. to provide for the preparation of working stock virus. Virus titers will be calculated by plaque formation on BHK cells. Virus will be diluted in growth medium with 10% fetal bovine serum for testing.

Antibodies: Antibodies to VSV-I will be obtained from the National Veterinary Diagnostic Laboratory, Ames Iowa and the ATCC, Chantilly, Va.

Polyurethane: Norland Optical Adhesive 61 (Norland Products, Cranbury, N.J. Liquid crystals: 5 CB, E7, ZLI 1221, MLC 1400-100, MLC10000-100 (EMD Chemicals)

Polyimide alignment layers: SE 7210, SE 7511L (Nissan Chemicals)

Glass slides: aluminosilicate, Corning 1737 F

Design of Electrode Geometry and Fabrication of Microelectrodes

Available software such as Coulomb 3D is used to simulate the electric field and to calculate the capacitance between in-plane electrodes. Based on the simulation results, appropriate electrode geometry (triangular, hyperbolic, interdigitated, etc.) and parameters (thickness, width, separation) will be identified so that the capacitance between the electrodes falls within an easily detectable range, typically in the pF range.

An order of magnitude estimate of the sensitivity of the electrical detection system was performed. The capacitance was calculated between interdigitated electrodes as shown in FIG. 3b with 5 μm width and 5 μm spacing between them. Using a semi-infinite strip approximation, the capacitance between electrodes with 50 fingers, each of length 500 μm, is $C=0.4 \in_{\mathit{eff}}$ pF, where $\in_{\mathit{eff}}$ is relative permittivity of the medium covering the electrodes. When a homogeneously aligned layer of LC undergoes orientational transition from planar to homeotropic configuration, the effective dielectric constant changes from $\in_{\mathit{planar}}=38$ to $\in_{\mathit{homeo}}=8$ (as calculated for the liquid crystal MLC10000-100) which corresponds to a capacitance change from 3.2 pF to 15 pF. A change in capacitance in the pF range can be detected by using a commercially available LCR meter in the laboratory setting or by measuring differential capacitance using an off-the-shelf chip (e.g., MS3110 Universal Capacitive Readout from MicroSensors Inc, Costa Mesa Calif.).

The sensitivity of the detection system depends on the resolution of the device used for measurement of the capacitance. Both commercially available LCR meters and off-the-shelf differential capacitance measurement chips have a resolution on the order of 0.1 fF in 10 pF level. An order of magnitude estimate of 0.1 fF resolution for interdigitated electrodes described above corresponds to a total of 10 virons on a 500 μm×500 μm area. This result predicts that by using an electrical detection system it is possible to detect 10 viron particles bound to the surface.

Arrays of interdigitated co-planar electrodes are designed based on the calculations described above. In preferred embodiments, electrodes are in the micrometer range and fabrication of these electrodes will be performed by using standard photolithographic methods of patterning followed by a lift off process. These electrode arrays are fabricated on commercially available glass substrates.

Estimation of the Change in Capacitance Between Planar and Homeotropic Orientation of Liquid Crystals Using electrodes fabricated as described above, experimental measurements are preformed to measure the capacitance of the liquid crystal anchored on the electrodes in known orientations. These measurements are performed by coating the electrodes with LC alignment films that give rise to known orientations of LCs. A thin (20 nm-thick) LC alignment layer (Nissan SE 7210) is coated onto two glass substrates (one with optimized electrodes and the other without electrodes) and buffed to create anisotropy in the surface morphology that aligns the LC material in a predetermined azimuthal direction perpendicular to the electrode fingers. An approximately 25 μm thick optical cell is fabricated by clamping these two substrates, separated by a Mylar film at each end, together. The liquid crystal 4-cyano-4'-pentylbiphenyl (5CB) is injected in to the gap between the substrates in isotropic phase (40° C.) and cooled down to room temperature. The capacitance is measured between the electrodes using a precision LCR meter (HP 42841, Agilent Technologies).

A similar cell is prepared using the homeotropic alignment layer (Nissan SE 7511L) and the capacitance between the electrodes is measured. A comparison between these two measurements provides an estimate of change in capacitance when LC undergoes orientational transition upon binding of virus to the surface.

Preparation of the Analytic Surface

In order to provide a chemically homogeneous surface onto which to immobilize the antibodies (for capture of virus), the co-planar electrode arrays are coated with a thin polymeric layer. The examples above established that antibodies immobilized on polyurethane films have a sufficient binding capacity for detection of WNV, therefore, a thin layer of polyurethane is spin coated onto the electrode arrays. In particular, a thin layer of polyurethane NOA 61 is spin coated onto the surface and degassed in a vacuum dessicator. A planar piece of polydimethylsiloxane (PDMS) is placed onto the NOA 61-coated glass slide, compressed and degassed. The sandwich is cross linked for 30 min in 365 nm ultraviolet light. The PDMS is peeled from the surface yielding a thin 40 μm layer of polyurethane on the substrate. If the PU film is too thick to see any changes due to liquid crystal re-orientation, thinner layers may be produced by dilution of the NOA 61 with acetone before spin coating onto the surface. The capacitance between the fingers of the electrodes is measured for reference.

Functionalization of the Analytic Surface and Optical Confirmation of Virus Binding Two procedures for immobilization of the antibodies are utilized. Both were found to permit detection of VSV in the examples above. The first approach uses the passive adsorption of antibodies onto the polyurethane surface. The second approach employs protein A to achieve the oriented immobilization of antibodies. The antibodies (monoclonal or rabbit polyclonal) are allowed to adsorb to the surface from a 20 μl droplet. The VSV-binding ability of these surfaces is validated by exposing the functionalized areas to solutions of VSV-I at 35° C. with rocking for 1.5 hours. The sample is rinsed with PBS, and 20 μm thick Mylar spacers placed at each end of the slide. A tridecafluoro-1,1,2,2-tetrahydrooctyl-1-trichlorosilane-coated slide is placed on top, and clamped to the bottom slide to form an optical cell. Fifteen μl of 5CB is added to the cell. The surface is then viewed between crossed (90°) polarizing filters. A dark field of view verifies the homeotropic alignment of LCs.

Example 20

Use of Capacitance Measurements in Combination with Liquid Crystals to Achieve Electrical Detection of Virus The measurement of capacitance Using surfaces and electrode geometries validated as described in Example 19, a high precision LCR meter is used to measure the change in capacitance between electrodes supporting a film of liquid crystal on a surface without bound virus and a film of liquid crystal upon a surface with bound virus. In order to determine the change in capacitance induced by the orientational transition, five optical cells are constructed:
1) untreated polyurethane(PU) surface;
2) PU surface treated with antibody to VSV-I;
3) PU surface treated with antibody to VSV-I and a non-specific virus such as herpes simplex;
4) PU surface treated with antibody to VSV-I, and VSV-I virus; and
5) PU surface treated with a non-specific antibody (e.g., anti-biotin IgG) and VSV-I virus.

A comparison of capacitance between two electrodes in all five types of cells provides a quantitative measure of the change in capacitance upon specific binding of VSV-1 to the surface. When implemented in the final device used for assay measurements, we will employ a differential capacitive measurement system similar to MS3110 Universal Capacitive Readout (MicroSensors Inc. CA) for measurements of capacitance. A system like the MS3110 permits facile measurement of the change in the differential capacitance between the electrodes treated with antibody targeted to VSV and the control surfaces (e.g. the surfaces presenting non-specific antibody). The output voltage of such a system is a linear function of the change in the differential capacitance between two inputs fed to it. A series of virus concentrations are tested to establish the relationship between the concentration of bound virus and the change in capacitance of the liquid crystal film.

Selection of Optimal Liquid Crystalline Materials

It is contemplated that the sensitivity of an assay based on LCs depend upon the ability of the LCs to undergo the orientational transition from a planar to a homeotropic configuration upon binding of the virus. This tendency to undergo the orientational transition depends on the detailed molecular level interaction between LC molecules and the virus particles. We will evaluate different LC materials, including 5CB, E7, MLC 1400-100, MLC10000-100, TL-205, for their applicability and effectiveness to undergo orientational transitions. In preliminary studies, 14 species of liquid crystals have been examined for their response to lipids and have identified those that assume a homeotropic orientation in response to lipids (Table 1). The change in capacitance between two electrodes also depends on dielectric anisotropy of the LC material, which is up to 30 for commercially available LC material. However, some reports have suggested that addition of small amounts of polar material could significantly increase the dielectric anisotropy of LC materials. Accordingly, devices are constructed that include known ferroelectric materials, such as $Sn_2P_2S_6$ (Ouskova et al, Dielectric relaxation spectroscopy of a nematic liquid crystal doped with ferroelectric $Sn_2P_2S_6$ nanoparticles. Liquid Crystals 30:1-5 (2003)), as dopants for enhancement of the dielectric anisotropy of LC that will ultimately increase the sensitivity of the assays.

Example 21

Dielectrophoretic Enhancement of Mass Transport of Virus

The presence of the electrodes utilized for capacitance measurement provides the opportunity to address a fundamental challenge that confronts all surface-based analytical methods. That is, the transport of the analyte from the sample matrix to the analytical surfaces is generally the rate-limiting step in surface-based analyses (often requiring prolonged incubation times for sufficient binding to occur). Certain methods of the present invention exploit the electrodes present on the analytical surfaces to accelerate the transport of virus to the surface via dielectrophoresis. Thus the electrodes in the device are multifunctional—they both increase the rate of transport of virus to the surface (via dielectrophoresis, as described below) and form the basis of a sensitive method to report the presence of the bound virus (as described in the preceding examples).

Dielectrophoresis is a phenomenon in which a polarizable particle in a non-uniform alternating current (AC) electric field experiences a net force and moves toward the region of high or low electric field strength. If the particle is more polarizable than the suspending medium, it moves toward the region of strong electric field and if the particle is less polarizable than the medium, it moves toward the region of low electric field. The magnitude of dielectrophoretic force depends also on, besides the dielectric properties of the particles and the medium, the gradient of the electric field and the size of the particle. For a particle of radius $r_p$ in an electric field with gradient $\Lambda/E_{rms}|^2$, the average dielectrophoretic force is given by, $$F_{DEP}=2\pi r_p^3 \in_m Re[K_E] \Lambda |E_{rms}|^2$$

where $\in_m$ is the permittivity of the medium, $E_{rms}$ is the root mean square electric field intensity and $Re[K_E]$ is the real part of Claussius-Mossoti factor given as, $$K_E = \frac{(\varepsilon_p^* - \varepsilon_m^*)}{(\varepsilon_p^* + 2\varepsilon_m^*)}$$

where $\in^*_p$ and $\in^*_m$ are effective dielectric permittivity of the particle and the medium, respectively. The direction of the dielectrophoretic force is determined by the relative sign of $Re[K_E]$ which depends on the relative conductivity and permittivity of the particle and the medium. For example, for a spherical virus particle suspended in a physiological medium such as TSE with $\sigma_m=600$ mSm$^{-1}$, and $\in_m=80\in_0$, the single shell model yields $Re[K_E]=-0.46$ at 10 MHz. This result indicates that the virus particle will move toward the region of lower electric field at 10 MHz. This is termed "negative dielectrophoresis". The dieletrophoretic force exerted on a virus particle of radius 250 nm, in a field gradient defined by hyperbolic electrodes separated by 10 μm with AC field of strength 5 $V_{pp}$ between them, located at the edge of the electrode is approximately 3 pN. For comparison, the force associated with Brownian motion of the particle in a medium is of the order of $F_B=K_BT/(2 r_p)$, where $K_B$ is the Boltzmann constant and T is the absolute temperature. Thus at room temperature, the force experienced by the virus particle is on the order of $10^{-2}$ pN. These results clearly indicate that the dieletrophoretic force is at least two orders of magnitude stronger than the thermal force exerted on the particle, which is responsible for the diffusive transport of the virus particles. Neglecting Brownian and buoyancy forces exerted on the particle, the equation of motion of the particle is determined by dielectrophoretic force and viscous drag acting on it. Using 3 pN for the dielectrophoretic force, the velocity of the virus particle is estimated to be 700 $\mu ms^{-1}$. Thus the time taken for the particle to travel a 100 µm distance is on the order of 0.1 s. The diffusion coefficient of the particle suspended in water can be estimated by using the Stokes-Einstein's equation; $D=K_BT/(6\pi\eta r_p)$ where $\eta$ is the coefficient of viscosity of medium. The diffusion coefficient is estimated to be $10^{-12}$ $m^2s^{-1}$. The time taken by the virus particle to diffuse through the same distance of 100 µm in absence of dielectrophoretic force is 1.4 hrs. This simple order of magnitude estimate shows that the dielectrophoretic force exerted on the virus particle suspended in a medium drives the virus particle at least four orders of magnitude faster than by the diffusion process alone. These results clearly indicate that application of the dielectrophoretic force significantly enhances the mass transport of the virus particles on to the surface, thus providing a basis for real time virus detection.

Optimization of Electrode Geometry for Dielectrophoresis of Virus

Figure 6:
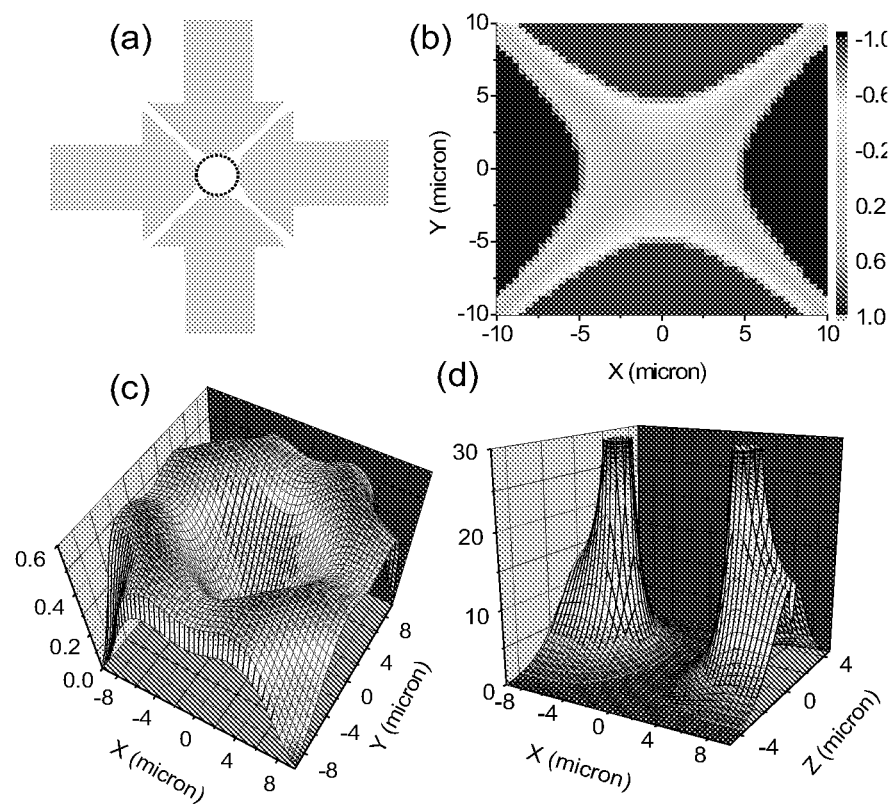
FIG. 6 shows the results from a simulation of hyperbolic electrodes.

The DEP force exerted on a virus particle depends strongly on a gradient of the electric field between two electrodes. In this task, different geometries of electrodes, such as interdigitated, hyperbolic, rectangular, and triangular will be investigated for their ability to produce the largest field gradient in the regions between the electrodes. This investigation will be guided by computer modeling of electric fields generated by different electrode arrays. This modeling will use commercially available software such as Coulomb 3D. FIG. 6 shows the results from a simulation of hyperbolic electrodes. These results show that the field gradient exhibits a local minimum at the center of the electrodes which will be the virus collection area for negative dielectrophoresis.

Dielectrophoretic Transport of Virus to a Surface

Results by Morgan et al. Separation of submicron bioparticles by dielectrophoresis. Biophysical Journal 77: 516-525 (1999) indicate that viruses exhibit both positive and negative dielectrophoresis as a function of electric field frequency and this behavior is dependent on the dielectric properties of the suspending medium. This cross-over effect in the frequency domain is investigated by using different suspension media for the virus particles. Buffers, such as Tris-saline EDTA, phosphate buffered saline, growth media such as Minimum Essential media with 10% fetal calf sera as well as various animal and human sera and standard viral transport media will be examined for their dielectric properties and their effects on the dielectrophoretic force exerted on the virus. Combinations of variables such as strength and frequency of the applied AC field, and ionic strength of the suspending medium, that yield the maximum response in the least amount of time and with the least amount of sample will be identified. To monitor these events in real time the virus particles are labeled. A method recently published by Akin et al., Real-time virus trapping and fluorescent imaging in microfluidic devices, Nano Letters 4: 257-259 (2004) is utilized which used a lipophilic carbocyanin dyes to label the envelope of vaccinia virus. The dyes (DiOC63 and DIL, Molecular Probes, Calif.) label the lipid membrane and capsid proteins of the virus and permitted visualization of surface bound vaccinia by digital epifluorescence microscopy at 400× magnification.

Antibody functionalized surfaces with integrated microelectrodes (FIG. 3) fabricated as described above are exposed to a 20 µL droplet of labeled VSV-1. An AC electric field is applied across the electrodes to induce dielectrophoretic motion of the virus particles to the surface in the region between the electrodes. VSV-1 binds to the antibodies on the surface. The field is turned off and the unbound virus is washed from the surface. These events are monitored in real time using a Zeiss-Axiovert 200 M microscope.

The optimal parameters for the dielectrophoresis of VSV-1 are identified by observation of the intensity of fluorescence seen within the center region of the electric field. The intensity of the fluorescence is correlated with the known concentrations of virus in the applied sample. The strength and frequency of the applied field that permit detection of the least amount of virus in under 5 minutes are chosen for testing against various suspension media of physiologic ionic strength. Such media include typical clinical materials such as serum, nasal swab fluid, and viral transport media to determine how the strength and frequency required for viral transport will be affected by these common sample fluids.

Example 22

Use of Beads for Capture of an Analyte Followed by Non-Specific Detection

Preparation of beads. Sera-Mag beads (0.8M in diameter) were functionalized with either 0.4 mg/mL EDC (Aldrich) or 1.1 mg/mL Sulfo-NHS (Pierce). First, 27 µl of 5% Sera-Mag beads were diluted in 1 mL of the functionalizing agent. Reactions were carried out 15 minutes and then quenched with 2-mercaptoethanol. The beads were washed 3 times with 25 mM MES and 37.5 mM NaCl. The washed beads were centrifuged at 11,300 rpm for 5 minutes. Removal of buffer was followed by the addition of fresh buffer. Next, 0.06 µM aF1pAb (100 µg/mL) was added for 1.5-2 hours during which the beads were rotated and mixed. The beads were quenched for amine by adding a final concentration of 10 mM D-glucosamine. The beads were then washed in PBS+D-glucusoamine (10 mM) for 20 minutes. The beads were transferred to regular microfuge tubes blocked with BSA to prevent non-specific binding of non-target molecules to the beads.

Detection of F1 antigen from *Yersinia pestis*. Magnetic beads were functionalized with anti-F1 polyclonal antibody as described above. A binding solution was prepared from PBS, Tween 0.05%, Heparin 50 µg/mL, and 100 mM additional NaCl. Wash solutions were prepared from PBS/Tween 0.05% and PBS/Tween 0.05%+200 mM additional NaCl. The beads were functionalized and stored in PBS at 0.135% w/v, the same concentration at which the beads were utilized. In the experiment, 1 mL of bead solution was utilized and bound up to 5 µg/ml of F1 at over 99.0%. An ELISA on F1 samples applied before and after capture on the on the beads was carried out. The F1 samples were placed on ELISA strip wells measured for levels of F1 protein using anti-F1 polyclonal antibody. The two conditions, start material and depleted material, were then graphed against absorbance 450 nm as result of ELISA colorimetric assay. This allowed to estimation of % of F1 captured by the functionalized beads. The data showed that almost all the F1 was absorbed to the beads. The F1 antigen was then eluted to a detection substrate surface comprising polyimide. The polyimide surface is prepared as follows: Undiluted polyimide 7511 liquid is applied to a slide, spin coated, pre-cured at 80° C. for 15 minutes, cured at 180° C. for one hour and stored at RT. Further, in the last step of the protocol, 10 uL 0.1M pH 2.4 glycine is mixed with the particle beads, and the tubes are then vortexed in a microfuge and placed on a magnetic stand to obtain separation of beads from supernatant. The low pH glycine serves to elute bound F1 and its antibody complex from the bead surface. 10 uL of the eluent is applied to the polyimide surface for the LC assay. Following elution, an optical cell was formed by adding a second substrate separated from the detection substrate by a thin mylar film. Mesogens (5CB) were then introduced into the optical cell.

Figure 8:
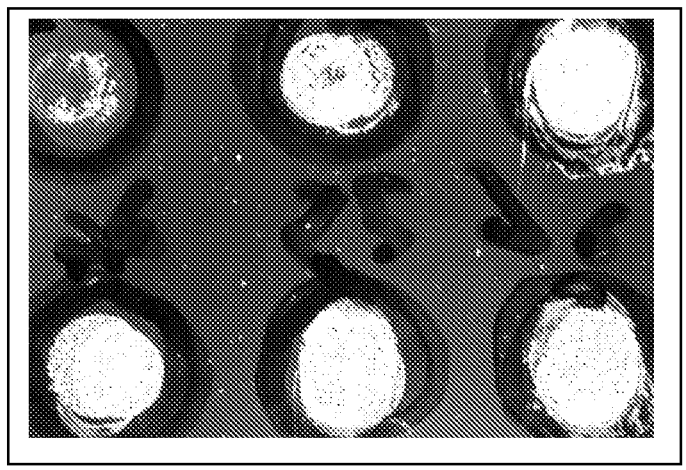
FIG. 8 is an image of an assay using a polyimide coated substrate to non-specifically detect an analyte.

Surfaces functionalized with polyimide 7511L orient liquid crystals in a homeotropic alignment in the absence of bound analyte. When analyte is present, the homeotropic orientation is disrupted. When viewed through cross polar lenses, homeotropic orientation is indicated by a dark field, while disrupted orientation is indicated by a bright field, as shown in FIG. 8. A digitized image taken with two Polaroid filters at cross polar configuration at 0°. Polyimide 7511L slides were prepared from 40% undiluted stock. These slides, in absence of protein, assume homeotropic alignment as shown in dark background. Upon protein binding, homeotropic alignment is disrupted and shown in white background. In the top row, from left to right, are elution samples from aF1pAb beads initially blocked with RNase A treated with BSA 400 ng/mL, F1 500 pg/mL and 2.5 ng/mL. The bottom row is 25, 100, and 400 ng/mL concentrations of F1. After initial protein binding in binding solution PBS/T/H/N, aF1pAb beads were washed in PBS/Tween 0.05%, 200 mM additional NaCl (PBS/T/N) wash solution.

Figure 9:
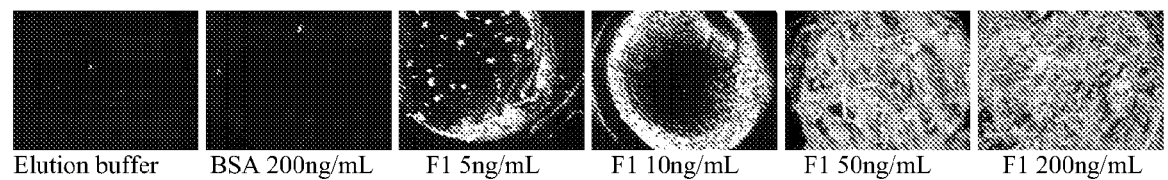
FIG. 9 is an image of an assay using a polyimide coated substrate to non-specifically detect an analyte.
Figure 10:
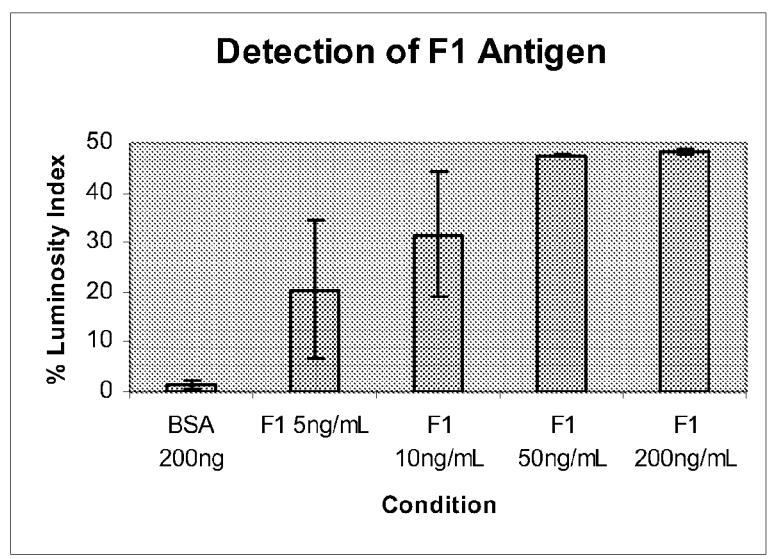
FIG. 10 is a graphic representation of luminosity index for the experiment depicted in FIG. 9.
Figure 11:
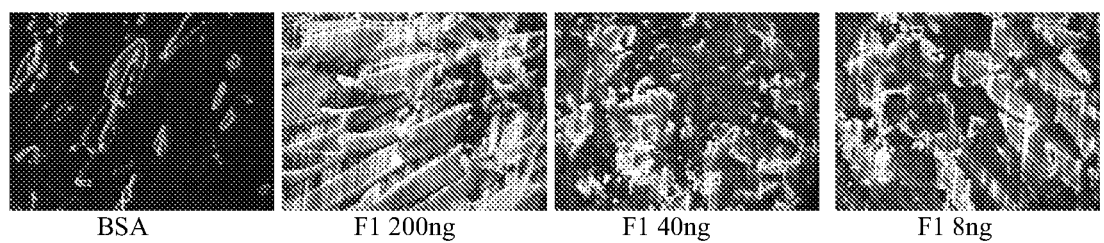
FIG. 11 is an image of an assay using a polyimide coated substrate to non-specifically detect an analyte.
Figure 12:
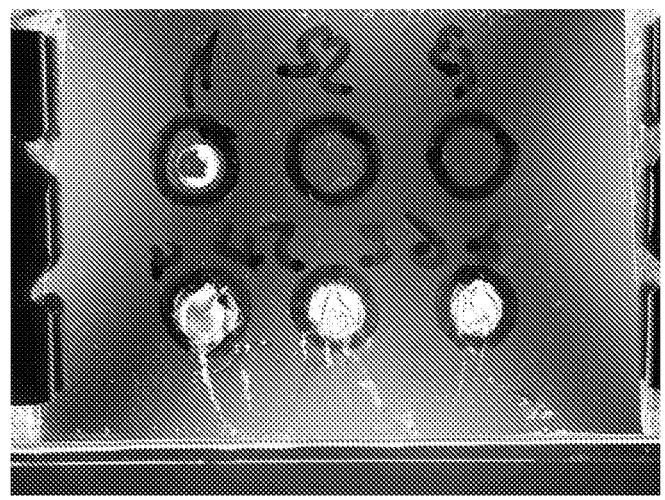
FIG. 12 is an image of the results of the detection of F1 in chicken serum.
Figure 13:
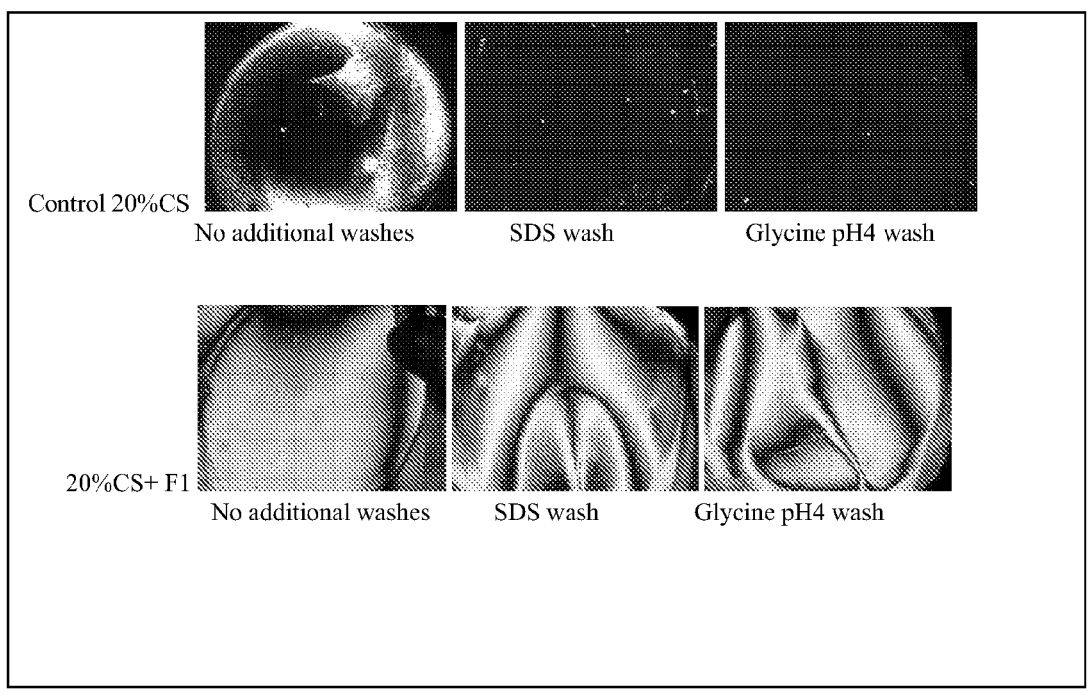
FIG. 13 is an image of the results of the same experiment as FIG. 12 taken with a polarized microscope.

An additional example demonstrates how this approach one can determine presence and quantity of the target molecule. FIG. 9 below demonstrates that with increasing F1 concentration, the disruption of homeotropic alignment increases as indicated by increased white signal against aligned LC black background on homeotropic aligning polyimide surfaces. This type of assay can be used to quantify levels of the F1 antigen.

In FIG. 9, the digitized figures were taken by polarized microscope with cross polar filters (0°). Polyimide 7511L slides were prepared from 40% undiluted stock. In absence of protein, these slides assume homeotropic alignment as shown in by the dark background. Upon protein binding homeotropic alignment is disrupted (indicated by a white background). The following samples were analyzed: elution buffer, BSA (200 ng/mL), and F1 elutions of beads exposed to 5, 10, 50 and 200 ng/mL concentrations of F1. The conditions were as described above. These experiments were carried in triplicate and FIG. 9 had intermediate levels of signal with respect to two other replicates (not shown). As can be seen, it was possible to detect 5 ng/mL analyte.

FIG. 10 is a graphic representation of luminosity index for the experiment depicted in FIG. 9. These experiments were carried in triplicate and figure chosen above have intermediate levels of signal with respect to two other replicates. Elution buffer was also applied to one area and used as reference for Luminosity index shown in the graph below.

In further experiments, a rubbed polyimide surface was utilized. FIG. 11 shows a digitized image taken with a polarized microscope with cross polar filters (0 degrees). Polyimide SE 7210 1.5% slides were rubbed at 2.55 ml/m setting at 4.0 cm/s table speed with a wheel speed of 343 rpm. FIG. 11 shows the results of elutions to the polyimide surface from functionalized aF1pAb beads that were treated with various concentrations of F1 or BSA as control. After washing, the beads were treated by the addition of rabbit anti-mouse IgG (5 μg/mL) and anti-mouse FC IgG (6 μg/mL). The complex was eluted off of the beads with 10 μl acid elution of 0.1 M glycine pH 2.3. Elution samples were neutralized by addition of 1 μl 1 M Tris pH 7.5. The samples were contacted with the polyimide substrate and an optical cell was constructed by placing a mylar spacer on the substrate clamping another substrate onto the first with bulldog clamp. 5CB was applied in liquid phase and after cooling the digitized image was acquired.

FIG. 12 provides the results of further experiments demonstrating the detection of an analyte (F1) from a complex medium (chicken serum). In these experiments, chicken serum (CS) was diluted to 20% with the binding solution PBS/T/H/N. BSA blocked beads functionalized as above were used. Six 0.5 mL suspensions of aF1pAb beads (0.135% concentration) were contacted with the diluted CS. After binding, all tubes were washed with PBS/Tween buffer. The beads were then washed a second time with 100 μL 0.5× PBS+2 mM SDS or 100 μL 0.1Mglycine pH 4.0. After mixing, the wash buffers were removed by pelleting the beads in PBS/Tween 0.05%. The beads were then washed with PBS/Tween/NaCl (additional 200 mM). aF1mAb at 3 μg/mL was then added to the beads in 0.5 ml tubes. The reactions were mixed and the supernatant was removed. Next, 0.75 mL of 5 μg/ml of both RAM and anti-mouse FC IgG were added for 5 minutes. The beads were washed with PBS/Tween/NaCl and then with PBS. Elution buffer (10 μL) was added to each tube mixed by vortexing for 3-4 minutes. The elution buffer (2 μL aliquots) was the applied to a 7511L homeotropic polyimide slide. The slides were placed on a heated plate for 2-3 minutes until droplets have evaporated. The slides were then washed with $dH_2O$ and dried with gas nitrogen. An optical cell was constructed by using a bulldog clamp to clamp together the treated substrate and an another substrate with a mylar spacer in between. 5CB in nematic phase was applied at room temperature. After 5 minutes, the homeotropic liquid crystal was observed.

FIG. 12 is a digitized image taken with cross polar filters (0 degrees). In top row are elutions from beads treated contacted with 20% CS with no additional wash, SDS wash, and a 0.1M glycine pH 4.0 wash. In the lower row are elutions from beads contacted with 20% CS+F1 50 ng/mL with no additional wash, SDS wash, or a 0.1M glycine pH 4.0 wash. FIG. 13 presents the results of the same experiments as analyzed with a polarized microscope. The digitized images were taken by polarized microscope where the polaroid filters are cross polar at 0°. The order of the treatments is the same as for FIG. 12.

The SDS and 0.1M Glycine washes were conducted to remove the BSA blocker from the functionalized beads so that there be no BSA signal interfering with F1 detection. As can be seen in FIG. 12 and FIG. 13 (polarized microscope image), both the SDS and Glycine washes eliminated the signal from the control top row second and third spots (20% Chicken Serum). Since the functionalized beads were blocked with BSA, it is most likely the BSA blocker that creates the signal seen in the first spot.

Example 23

Homeotropic Orientation of Liquid Crystals by Cells

Tables 2 and 3 present the results of experiments in which different liquid crystals were surveyed for their ability to be homeotropically oriented by cultured cells. Many liquid crystals align homeotropically in response to phospholipids and cholesterol. Phospholipids (2 ul; 0.01 M in chloroform) were applied to discrete marked areas on glass slides. The phospholipids had dioleoyl alkyl chains and the following headgroups: phosphatidylserine (DOPS), phosphatidylglycerol (DOPG), phosphatidylethanolamine (DOPE), phosphatidylserine (DOPS), phosphatidic acid (DOPA), and

TABLE 2

Survey of liquid crystals for alignment by cells and by slide exposed to medium.

| Liquid Crystal | FBS/DMEM | 3T3 cells |
|---|---|---|
| 4OCB | Disrupted | Homeotropic |
| 5CB | Disrupted | Homeotropic |
| 6CHBT | Planar, with defects | Homeotropic |
| E7 | Disrupted | Homeotropic |
| ZLI-1221 | Planar, streaky | Disrupted |
| ZLI-1557 | Planar with streaky defects | Homeotropic |
| ZLI-2222 | Planar, minor defects | Homeotropic |
| ZLI-3225 | Planar with streaky defects | Homeotropic (tilt) |
| ZLI-3497 | Planar with streaky defects | Homeotropic (tilt) |
| ZLI-4431 | Planar with streaky defects | Homeotropic (tilt) |
| ZLI-4446 | Planar, with defects | Homeotropic |
| ZLI-5070 | Planar with streaky defects | Homeotropic (tilt) |
| MLC-6080 | Planar with squiggly defects | Homeotropic |
| MLC-6466 | Planar with streaky defects | Homeotropic |
| MLC-6710-080 | Planar with streaky defects | Homeotropic |
| MLC-15700-000 | Planar, streaky | Homeotropic |
| TL205 | Somewhat planar | Homeotropic | lysophosphatidylcholine (DOLPC). After the solvent dried, optical cells were assembled with liquid crystals applied nematically and heated to isotropy. Homeotropic alignment was confirmed by conoscopic analysis. Chol=cholesterol; C=cholesteric alignment; Bkg=background alignment; U=unaligned; H=homeotropically aligned; ND indicates not done due to background. 4OCB, 4'-octyl-4-biphenyl-carbonitrile (Aldrich); 6CHBT, 1-(trans-4-hexylcyclohexyl)-4-isothiocyanato-benzene. All other liquid crystals are from EM Industries/Merck.

TABLE 3

Investigation of phospholipid influence on liquid crystal alignment.

| Liquid Crystal | Bkg | DOPS | DOPG | DOPC | DOPE | DOPA | DOLPC | Chol |
|---|---|---|---|---|---|---|---|---|
| 4OCB | H | ND | ND | ND | ND | ND | ND | ND |
| 5CB | | U | H | H | H | Planar | H | U |
| 6CHBT | | U | H | H | H | H | H | U |
| E7 | | Twisted planar | H | H | H | Twisted planar | H | H |
| ZLI-1221 | | H | H | H | H | H | H | H |
| ZLI-1557 | | H | H | H | H | H | H | H |
| ZLI-2222 | | H | H | H | H | H | H | H |
| ZLI-3225 | | U | H | H | H | H | H | H |
| ZLI-3497 | H | ND | ND | ND | ND | ND | ND | ND |
| ZLI-4431 | Chol | U | U | U | U | U | U | U |
| ZLI-4446 | H | ND | ND | ND | ND | ND | ND | ND |
| ZLI-5070 | | Twisted planar | H | H | H | H | H | H |
| MLC-6080 | | U | H | H | H | H | H | H |
| MLC-6466 | | U | H | H | H | H | H | H |
| MLC-6710-080 | | U | H | H | H | H | H | H |
| MLC-15700-000 | | H | H | H | U | H | H | U |
| TL205 | | U | H | H | H | H | H | H |

APES (3-Aminopropyltriethoxysilane; Pierce) in dry acetone for 2 min. Slides were transferred to pure acetone and stirred for 5 min and rinsed with acetone to remove excess of silane. Slides were dried with nitrogen and kept at 110° C. oven for 45 min. Slides were removed from oven and after they reached room temperature areas were marked on one side of slide. 1 mg/ml BS3 (Bis (Sulfosuccinimidyl) suberate; Pierce) cross-linker was applied as 10 ul drops on marked areas and incubated for 15 min at room temperature. After rinsing excess cross-linker with water surfaces were dried with nitrogen gas. 100 ug/ml and 20 ug/ml anti-biotin antibody (Sigma; Anti-Biotin Developed in Goat) was applied on BS3 treated surfaces and incubated for 2 hrs at room temperature or 1 hr at room temperature and later transferred to 4° C. overnight. Antibody immobilized surfaces were rinsed with milliQ water to remove unbound protein and dried with N2. Liposome labeled with biotin (17.84 micromol phospholipid/ml) and unlabeled liposome (18.7 micromol phospholipid/ml) were diluted 100fold with PBS buffer, and 10 ul of liposome was applied on anti-biotin treated surface. PBS buffer was added on one area as buffer control. After 1:30 hrs incubation at room temperature, surfaces was rinsed with water and N2 dried. Two protein treated surfaces were kept apart by inserting 20 μm mylar spacer at two sides and two surfaces were aligned in anti-parallel direction. Two surfaces were held together by using bulldog clips placed along the mylar placed sides. The cells were heated to ~40° C. by placing them on hot plate. I also used hot air to warm the air around the cells. 5CB was heated into its isotropic phase within a glass syringe. A drop of 5CB was drawn into the cavity between two surfaces by capillary force. Once filled with 5CB, the cell was removed form hot plate. After reaching room temperature, isotropic phase of 5CB transformed to the nematic state.

Example 24

Detection of Analyte with Tagged Lipids

This experiment describes the detection of binding of liposomes labeled with biotin to the immobilized anti-biotin antibody using liquid crystals. Anti-biotin immobilized glass substrates were prepared as follows. PrecisionCT slides (Bioslide Technologies; Cat# BSP-SC02-C) cleaned in plasma asher (20 min, 275 watts, 200 millitor) were immersed in 2%

Optical images were taken at crossed polar position using polarizing microscope. The above experiment was done in triplicates. The data from one experiment is presented in FIG. 15.

Binding of biotin labeled liposome to the immobilized anti-biotin antibody changes disrupted surface to homeotropic (black) where as no change was noticed with unlabeled liposome. This experiment demonstrates the use of liposomes labeled with target molecule to study receptor-ligand interactions.

The biotin labeled liposomes were prepared from 100 micromol (75 mg) egg phosphatidylcholine; 1 micromol (1.28 mg) phosphatidylethanolamine-N-(lissamine rhodamine B; sulfonyl) ammonium salt; 1 micromol (1.05 mg) 1,2-dipalmitoyl-snglycero-3-phosphoethanolamine-N-(cap Biotinyl) sodium salt. The control liposomes were prepared from 100 micromol (75 mg) egg phosphatidylcholine; 1 micromol (1.28 mg); phosphatidylethanolamine-N-(lissamine rhodamine B sulfonyl) ammonium salt The lipid mixtures were prepared by combining the desired quantities of the components in chloroform solution. Each solution was then divided in two for liposome preparation. For each batch The solution was dried down in a B24/40 boiling tube on a rotary evaporator. The resultant film was suspended in 5 ml. of hydrated isopropylether. To the lipid solution was added 2 ml of buffer. At this stage the buffer does not mix with the ether phase. The tube was stoppered, and the mixture was sonicated in a bath type sonicator (Laboratory Supply company, Hicksville N.Y.) at 55 C to give a water-in-ether emulsion. The ether was then evaporated from the emulsion using a rotary evaporator, bath temperature 55 C. After ether removal, the mixture formed a viscous gel, which on agitation, broke down to give a liposome suspension. After liposome formation, the two 50 micromol batches for sample and control liposomes respectively were combined for the next step.

The size of the liposomes was then reduced to a smaller and more uniform diameter by a process known as extrusion, wherein they were passed through a series of polycarbonate membranes of defined pore size. The extrusion chamber was heated to 6° C., and the liposomes were passed five times through a 0.4 micron pore size polycarbonate membrane, and then five times through a 0.1 micron pore size polycarbonate membrane. The process of extrusion noticeably reduces the turbidity of the suspension.

The liposomes were then dialysed overnight at 4 C against 1 liter of the suspension buffer so as to eliminate any residual traces of isopropylether. The liposomes were analyzed for their phospholipid content using the phosphorus assay of Bartlett, and were found to contain:

Sample (biotin) liposomes: 17.84 micromol phospholipid/ml

Control liposomes: 18.7 micromol phospholipid/ml

The liposomes were analyzed for their size using a Nicomp 380 particle sizer. The volume-weighted gaussian mean diameters were:

Sample (biotin) liposomes: 134 nanometer

Control liposomes: 157 nanometer.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in organic chemistry, materials science, chemical engineering, virology, biology, genetics, or related fields are intended to be within the scope of the following claims.

What is claimed is:

1. A method for detecting a biological entity containing a lipid membrane comprising:
   a) providing:
      i) a sample suspected of containing a biological entity containing a lipid membrane;
      ii) a detection device comprising a substrate comprising at least one detection region;
      iii) mesogens;
   b) contacting said detection region with said sample;
   c) contacting said sample with said mesogens, and
   d) detecting the presence of said biological entity containing a lipid membrane by observation of a change in said mesogens due to contact with said lipid membrane.

2. The method of claim 1, wherein said change in said mesogens is selected from the group consisting of a change in color, a change in texture, a change in tilt, and change in orientation.

3. The method of claim 1, wherein said change in mesogens is detected by a method selected from the group consisting of visual detection, optical detection, spectroscopic detection, light transmission, and electrical detection.

4. The method of claim 1, wherein said biological entity containing a lipid membrane is an entity selected from the group consisting of a eukaryotic cell, a bacterium, a Mycoplasma, a virus, and a liposome or combinations thereof.

5. The method of claim 4, wherein said liposome further displays a ligand.

6. The method of claim 1, wherein said substrate is selected from the group consisting of metal films, glass, silicon, diamond and polymeric materials.

7. The method of claim 6, wherein said polymeric materials are selected from the group consisting of polyurethane, PDMS, polyimide, polystyrene, polycarbonate and polyisocyanoacrylate.

8. The method of claim 1, wherein said mesogen is selected from the group consisting of 4-cyano-4'-pentylbiphenyl, N-(4methoxybenzylidene)-4-butlyaniline and combinations thereof.

9. The method of claim 1, wherein said detection region further comprises a recognition moiety that recognizes said biological entity.

10. The method of claim 1, wherein said substrate comprises a plurality of detection regions.

11. The method of claim 1, wherein said change in said mesogens is detected by viewing said detection device between cross polar lenses.

12. The method of claim 1, wherein said sample is selected from the group consisting of biological fluids, tissue homogenates, feces, vesicular fluids, tissue swabs, and media in which a biological agents have been cultured or prepared.

13. The method of claim 12, wherein said biological fluid is selected from the group consisting of cerebral-spinal fluid, urine, serum, plasma, nasal secretions, sputum, semen and saliva.

14. A method for detecting an analyte comprising:
   a) providing:
      i. a sample suspected of containing an analyte
      ii. a recognition moiety that is complexed with a biological entity comprising a lipid membrane,
      iii. mesogens
   b) contacting said sample with said recognition moiety-lipid membrane complex wherein said recognition moiety interacts with said analyte, to form an analyte-recognition moiety-lipid membrane complex;
   c) contacting said analyte-recognition moiety-lipid complex with said mesogens, and d) detecting the presence of said analyte by observation of homeotropic orientation of said liquid crystal caused by contact with said lipid membrane in said analyte-recognition moiety-lipid-membrane complex.

15. The method of claim 14, wherein said change of said mesogens is detected by a method selected from the group consisting of visual detection, optical detection, spectroscopic detection, light transmission, and electrical detection.

16. The method of claim 14, wherein said sample is selected from the group consisting of biological fluids, tissue homogenates, feces, vesicular fluids, tissue swabs, and media in which biological agents have been cultured or prepared.

17. The method of claim 16, wherein said biological fluid is selected from the group consisting of cerebral-spinal fluid, urine, serum, plasma, nasal secretions, sputum, semen and saliva.

18. The method of claim 14, wherein said sample is applied to a substrate.

19. The method of claim 18, wherein said substrate is selected from the group consisting of metal films, glass, silicon, diamond and polymeric materials.

20. The method of claim 18, wherein said substrate further comprises at least one detection region.

21. The method of claim 20, wherein said detection region further comprises a ligand that recognizes said analyte.

22. The method of claim 14, wherein said recognition moiety-lipid complex is immobilized on said substrate.

23. The method of claim 22, wherein said recognition moiety is an enzymatic substrate.

24. The method of claim 14 wherein said analyte is an enzyme.

25. The method of claim 18, wherein said substrate comprises a plurality of detection regions.

26. The method of claim 19, wherein said polymeric materials are selected from the group consisting of polyurethane, PDMS, polyimide, polystyrene, polycarbonate and polyisocyanoacrylate.

27. The method of claim 14, wherein said mesogen is selected from the group consisting of 4-cyano-4'-pentylbiphenyl, N-(4methoxybenzylidene)-4-butlyaniline and combinations thereof.

28. The method of claim 1, wherein said biological entity comprising a lipid membrane is selected from the group consisting of a membrane fragment, individual lipid molecules, and lipid-based material.

* * * * *